US006733990B1

(12) United States Patent
Hodge et al.

(10) Patent No.: US 6,733,990 B1
(45) Date of Patent: May 11, 2004

(54) NUCLEIC ACID ENCODING 15571, A GPCR-LIKE MOLECULE OF THE SECRETIN-LIKE FAMILY

(75) Inventors: Martin R. Hodge, Arlington, MA (US); Clare Lloyd, London (GB); Nadine S. Weich, Brookline, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 97 days.

(21) Appl. No.: 09/631,603

(22) Filed: Aug. 3, 2000

Related U.S. Application Data

(63) Continuation-in-part of application No. 09/515,781, filed on Feb. 29, 2000, now abandoned.
(60) Provisional application No. 60/146,916, filed on Aug. 3, 1999.

(51) Int. Cl.[7] .......................... C12N 15/12; C12N 5/10; C12N 15/63

(52) U.S. Cl. .................... 435/69.1; 435/71.1; 435/71.2; 435/252.3; 435/254.11; 435/325; 435/471; 435/320.1; 536/23.5; 530/350

(58) Field of Search ............................... 536/23.1, 23.5; 530/350; 435/69.1, 71.1, 71.2, 325, 320.1, 471, 252.3, 254.11

(56) References Cited

U.S. PATENT DOCUMENTS

| | | | |
|---|---|---|---|
| 5,576,296 | A | 11/1996 | Bartfai et al. |
| 5,756,460 | A | 5/1998 | Evans et al. |

FOREIGN PATENT DOCUMENTS

| | | |
|---|---|---|
| EP | 0 787 797 A1 | 8/1997 |
| WO | WO 94/01548 | 1/1994 |
| WO | WO 96/39442 | 12/1996 |
| WO | WO 98/02553 | 1/1998 |
| WO | WO 98/11218 | 3/1998 |
| WO | WO 98/15570 | 4/1998 |
| WO | WO 98/34948 | 8/1998 |
| WO | WO 98/45436 A2 | 10/1998 |
| WO | WO 98/45467 | 10/1998 |
| WO | WO 98/48016 | 10/1998 |
| WO | WO 98/50549 | 11/1998 |
| WO | WO 98/53062 | 11/1998 |
| WO | WO 99/29849 | 6/1999 |
| WO | WO 99/33982 | 7/1999 |
| WO | WO 99/35106 | 7/1999 |
| WO | WO 99/38972 | 8/1999 |
| WO | WO 99/40100 | 8/1999 |
| WO | WO 99/42582 | 8/1999 |
| WO | WO 99/46378 | 9/1999 |
| WO | WO 99/54461 | 10/1999 |
| WO | WO 99/55733 | 11/1999 |
| WO | WO 99/57270 | 11/1999 |

OTHER PUBLICATIONS

Robertson et al. (1994) "Isolation of Novel and Known Genes from a Human Fetal Cochlea cDNA Library Using Subtractive Hybridization and Differential Screening," *Genomics* 23:42–50.

Database GENCORE on STN. PIR Accession No. T14774, Poustka et al., Sep. 20, 1999.

Database GENCORE on STN. PIR Accession No. V89895, Agostino et al., Feb. 15, 1999.

Akbar et al., "Molecular Cloning of a Novel P2 Purinoceptor from Human Erythroleukemia Cells," *J. Biol. Chem.* (Aug. 2, 1996), pp. 18363–18367, vol. 271, No. 31.

An et al., "Molecular Cloning of the Human Edg2 Protein and Its Identification as a Functional Cellular Receptor for Lysophosphatidic Acid," *Biochemical and Biophysical Research Communications* (Feb. 24, 1997), pp. 619–622, vol. 231, No. 3.

An et al., "Identification of cDNAs Encoding Two G Protein–Coupled Receptors for Lysosphingolipids," *FEBS Lett.* (1997), pp. 279–282, vol. 417, No. 3.

An et al., "Characterization of a Novel Subtype of Human G Protein–coupled Receptor for Lysophosphatidic Acid," *J. Biol. Chem.* (Apr. 3, 1998), pp. 7906–7910, vol. 273, No. 14.

Blackshaw et al., "Encephalopsin: A Novel Mammalian Extraretinal Opsin Discretely Localized in the Brain," *Journal of Neuroscience*, May 15, 1999, pp. 3681–3690, vol. 19(10).

Bowles, et al., "Gene Mapping of Familial Autosomal Dominant Dilated Cardiomyopathy to Chromosome 10q21–23," *J. Clin. Invest.* (Sep. 1996), pp. 1355–1360, vol. 98, No. 6.

Eva et al., "Molecular Cloning of a Novel G Protein–Coupled Receptor That May Belong to the Neuropeptide Receptor Family,", *FEBS Lett.* (Oct. 1990), pp. 81–84, vol.271, Nos. 1,2.

Fukushima et al., "A Single Receptor Encoded by vzg–1/$lp_{A1}$/edg–2 Couples to G Proteins and Mediates Multiple Cellular Responses to Lysophosphatidic Acid," *Proc. Natl. Acad. Sci. USA* (May 1998), pp. 6151–6156, vol. 95, No. 11.

Gerard et al., "The Chemotactic Receptor for Human C5a Anaphylatoxin," *Nature* (Feb. 14, 1991), pp. 614–617, vol. 349.

(List continued on next page.)

*Primary Examiner*—Prema Mertz
(74) *Attorney, Agent, or Firm*—Millennium Pharmaceuticals, Inc.

(57) ABSTRACT

Novel GPCR-like polypeptides, proteins, and nucleic acid molecules are disclosed. In addition to isolated, full-length GPCR-like proteins, the invention further provides isolated GPCR-like fusion proteins, antigenic peptides, and anti-GPCR-like antibodies. The invention also provides GPCR-like nucleic acid molecules, recombinant expression vectors containing a nucleic acid molecule of the invention, host cells into which the expression vectors have been introduced, and nonhuman transgenic animals in which a GPCR-like gene has been introduced or disrupted. Diagnostic, screening, and therapeutic methods utilizing compositions of the invention are also provided.

12 Claims, 28 Drawing Sheets

OTHER PUBLICATIONS

Guo et al., "Molecular Cloning of a High–Affinity Receptor for the Growth Factor–Like Lipid Mediator Lysophosphatidic Acid from *Xenopus* Oocytes," *Proc. Natl. Acad. Sci. USA* (Dec. 1996), pp. 14367–14372, vol. 93, No. 25.

Hla et al., "An Abundant Transcript Induced in Differentiating Human Endothelial Cells Encodes a Polypeptide with Structural Similarities to G–Protein–Coupled Receptors," *J. Biol. Chem.* (Jun. 5, 1990), pp. 9308–9313, vol. 265, No. 16.

Ishihara et al., "Protease–Activated Receptor 3 is a Second Thrombin Receptor in Humans," *Nature* (Apr. 3, 1997), pp. 502–506, vol. 386.

Lee et al., "Lysophosphatidic Acid Stimulates the G–Protein–Coupled Receptor EDG–1 as a Low Affinity Agonist," *J. Biol. Chem.* (Aug. 21, 1998), pp. 22105–22112, vol. 273, No. 34.

Lee et al., "Molecular Biology of G–Protein–Coupled Receptors," *Trends in Biomedical Research* (Sep. 1993), pp. 488–497, vol. 6, No. 7.

Libert et al., "Selective Amplification and Cloning of four New Members of the G Protein–Coupled Receptor Family," *Science* (May 5, 1989), pp. 569–572, vol. 244.

Meyerhof et al., "Molecular Cloning of a Novel Putative G–Protein Coupled Receptor Expressed During Rat Spermiogenesis," *FEBS Lett.* (Jun. 1991), pp. 155–160, vol. 284, No. 2.

Mills et al., "Orphan Seven Transmembrane Domain Receptors: Reversing Pharmacology," *Trends in Biotechnology* (Feb. 1994), pp. 47–49, vol. 12.

O'Dowd et al., "Cloning and Chromosomal Mapping of Four Putative Novel Human G–Protein–Coupled Receptor Genes," *Gene*, Mar. 10, 1997, pp. 75–81, vol. 187 (1).

O'Dowd et al., "Discovery of Three Novel G–Protein–Coupled Receptor Genes, " *Genomics* (1998), pp. 310–313, vol. 47.

Oliveira et al., "A Common Motif in G–Protein–Coupled Seven Transmembrane Helix Receptors," *Journal of Computer–Aided Molecular Design* (1993), pp. 649–658, vol. 7.

Ross et al., "RTA, a Candidate G Protein–Coupled Receptor: Cloning, Sequencing, and Tissue Distribution," *Proc. Natl. Acad. Sci. USA* (Apr. 1990), pp. 3052–3056, vol. 87, No. 8.

Scott et al., "Searching for Peptide Ligands with an Epitope Library," *Science* (Jul. 27, 1990), pp. 386–390, vol. 249.

Stadel et al., "Orphan G Protein–Coupled Receptors: A Neglected Opportunity for Pioneer Drug Discovery," *TiPS* (Nov. 1997), pp. 430–437, vol. 18.

Takada et al., "Cloning of cDNAs Encoding G Protein–Coupled Receptor Expressed in Human Endothelial Cells Exposed to Fluid Shear Stress," *Biochem. Biophys. Res. Commun.* (Nov. 26, 1997), pp. 737–741, vol. 240, No. 3.

Vu et al., "Molecular Cloning of a Functional Thrombin Receptor Reveals a Novel Proteolytic Mechanism of Receptor Activation," *Cell* (Mar. 22, 1991), pp. 1057–1068, vol. 64.

Yokomizo et al., "A G–Protein–Coupled Receptor for Leukotriene $B_4$ That Mediates Chemotaxis," *Nature* (Jun. 5, 1997), pp. 620–624, vol. 287.

Zondag et al., "Sphingosine 1–Phosphate Signalling Through the G–Protein–Coupled Receptor Edg–1," *Biochem. J.* (1998), pp. 605–609, vol. 330, Part 2.

```
GGAGTCGACCCACGCGTCCGCGGCGCGATCCGCTAGGTCCCAGCCCAGCGCCCAGCGAGCAGGCGACGCGGAGGGGCCG

GGCCTCCAGTGTCCCGAGGGCCGCGCGCTGAGACTCCGGCCGCGCAGCTGGGAGCTGCCCGCGCTGCGCTGACAGCCGC

GCCGACGTCCTCCCCGCCGGGGCGCTCGCAGGACATGCCCCCGGGGCGCGGCGGCGGGGACCCCGGGGCTCGCCTCCGC

CCAGGGCCCCCCTCCACGCCCTCGGGAGCCCCGGGCCCCCGCTGAGCACTCCTCCCGCACGCCTGGGTCCCTCCGGCCG

                                                 M   G   A   G   G   R   R      7
GCGCGCAGCCCGGCCCCAGCGCTGTGGGTCCCCGCGGGGCGATGGGTTG ATG GGC GCC GGG GGA CGC AGG    21

 M   R   G   A   P   A   R   L   L   L   P   L   L   P   W   L   L   L   L   L    27
ATG CGG GGG GCG CCC GCG CGC CTG CTG CTG CCG CTG CTG CCG TGG CTC CTG CTG CTC CTG   81

 A   P   E   A   R   G   A   P   G   C   P   L   S   I   R   S   C   K   C   S    47
GCG CCC GAG GCT CGG GGC GCG CCC GGC TGC CCG CTA TCC ATC CGC AGC TGC AAG TGC TCG  141

 G   E   R   P   K   G   L   S   G   G   V   P   G   P   A   R   R   R   V   V    67
GGG GAG CGG CCC AAG GGG CTG AGC GGC GGC GTC CCT GGC CCG GCT CGG CGG AGG GTG GTG  201
```

FIG. 1A-1

```
C   S   G   G   D   L   P   E   P   P   E   P   G   L   L   P   N   G   T   V    87
TGC AGC GGC GGG GAC CTC CTC GAG CCT CCC GAG CCC GGC CTT CTG CCT AAC GGC ACC GTT  261

T   L   L   L   S   N   N   K   I   T   G   L   R   N   G   S   F   L   G   L   107
ACC CTG CTC TTG AGC AAT AAC AAG ATC ACG CCC CTC GCG AAT GGC TCC TTC CTG GGA CTG  321

S   L   L   E   K   L   D   L   R   N   N   I   I   S   T   V   Q   P   G   A   127
TCA CTG CTG GAG AAG CTG GAC CTG AGG AAC AAC ATC ATC AGC ACA GTG CAG CCG GGC GCC  381

F   L   G   L   G   E   L   K   R   L   D   L   S   N   N   R   I   G   C   L   147
TTC CTG GGC GTG GGG GAG CTG AAG CGT TTA GAT CTC TCC AAC AAC CGG ATT GGC TGT CTC  441

T   S   E   T   F   Q   G   L   P   R   L   L   R   L   N   I   S   G   N   I   167
ACC TCC GAG ACC TTC GAG GGC CTC CCC AGG CTT CTC CGA CTA AAC ATA TCT GGA AAC ATC  501

F   S   S   L   Q   P   G   V   F   D   E   L   P   A   L   K   V   V   D   L   187
TTC TCC AGT CTG CAA CCT GGG GTC TTT GAT GAG CTG CCA GCC CTT AAG GTT GTG GAC TTG  561

G   T   E   F   L   T   C   D   C   H   L   R   W   L   L   P   W   A   Q   N   207
GGC ACC GAG TTC CTG ACC TGT GAC TGC CAC CTG CGC TGG CTG CTG CCC TGG GCC CAG AAT  621
```

FIG. 1A-2

```
R   S   L   Q   L   S   E   H   T   L   C   A   Y   P   S   A   L   H   A   Q    227
CGC TCC CTG CAG CTG TCG GAA CAC ACG CTC TGT GCT TAC CCC AGT GCC CTG CAT GCT CAG  681

A   L   G   S   L   Q   E   A   Q   L   C   C   E   G   A   L   E   L   H   T    247
GCC CTG GGC AGC CTC CAG GAG GCC CAG CTC TGC TGC GAG GGG GCC CTG GAG CTG CAC ACA  741

H   H   L   I   P   S   L   R   Q   V   V   F   Q   G   D   R   L   P   F   Q    267
CAC CAC CTC ATC CCG TCC CTA CGC CAA GTG GTG TTC CAG GGG GAT CGG CTG CCC TTC CAG  801

C   S   A   S   Y   L   G   N   D   T   R   I   R   W   Y   H   N   R   A   P    287
TGC TCT GCC AGC TAC CTG GGC AAC GAC ACC CGC ATC CGC TGG TAC CAC AAC CGA GCC CCT  861

V   E   G   D   E   Q   A   G   I   L   L   A   E   S   L   I   H   D   C   T    307
GTG GAG GGT GAT GAG CAG GCG GGC ATC CTC CTG GCC GAG AGC CTC ATC CAC GAC TGC ACC  921

F   I   T   S   E   L   T   L   S   H   I   G   V   W   A   S   G   E   W   E    327
TTC ATC ACC AGT GAS CTG ACG CTG TCT CAC ATC GGC GTG TGG GCC TCA GGC GAG TGG GAG  981
```

FIG. 1A-3

```
     C   T   V   S   M   A   Q   G   N   A   S   K   K   V   E   I   V   L   E    347
    TGC ACC GTG TCC ATG GCC CAA GGC AAC GCC AGC AAG AAG GTG GAG ATC GTG CTG GAG   1041

     T   S   A   S   Y   C   P   A   E   R   V   A   N   N   R   G   D   F   R   W   367
    ACC TCT GCC TCC TAC TGC CCC GCC GAG CGT GTT GCC AAC AAC CGC GGG GAC TTC AGG TGG  1101

     P   R   T   L   A   G   I   T   A   Y   Q   S   C   L   Q   Y   P   F   T    387
    CCC CGA ACT CTG GCC GGC ATC ACA GCC TAC CAG TCC TGC CTG CAG TAT CCC TTC ACC   1161

     V   P   L   G   G   G   A   P   G   T   R   A   S   R   R   C   D   R   A   G   407
    GTG CCC CTG GGC GGG GGT GCC CCG GGC ACC CGA GCC TCC CGC CGG TGT GAC CGT GCC GGC  1221

     R   W   E   P   G   D   Y   S   H   C   L   Y   T   N   D   I   T   R   V   L   427
    CGC TGG GAG CCA GGG GAC TAC TCC CAC TGT CTC TAC ACC AAC GAC ATC ACC AGG GTG CTG  1281

     Y   T   F   V   L   M   P   I   N   A   S   N   A   L   T   L   A   H   Q   L   447
    TAC ACC TTC GTG CTG ATG CCC ATC AAT GCG TCC AAC GCG CTG ACC CTG GCT CAC CAG CTG  1341

     R   V   Y   T   A   E   A   A   S   F   S   D   M   M   D   V   V   Y   V   A   467
    CGC GTG TAC ACA GCC GAG GCC GCT AGC TTT TCA GAC ATG ATG GAT GTA GTC TAT GTG GCT  1401
```

FIG. 1B-1

```
Q   M   I   Q   K   F   L   G   Y   V   D   Q   I   K   E   L   V   E   V   M    487
CAG ATG ATC CAG AAA TTT TTG GGT TAT GTC GAC CAG ATC AAA GAG CTG GTA GAG GTG ATG 1461

V   D   M   A   S   N   L   M   L   V   D   E   H   L   L   W   L   A   Q   R    507
GTG GAC ATG GCC AGC AAC CTG ATG CTG GTG GAC GAG CAC CTG CTG TGG CTG GCC CAG CGC 1521

E   D   K   A   C   S   R   I   V   G   A   L   E   R   I   G   G   A   A   L    527
GAG GAC AAG GCC TGC AGC CGC ATC GTG GGT GCC CTG GAG CGC ATT GGG GGG GCC GCC CTC 1581

S   P   H   A   Q   H   I   S   V   N   A   R   N   V   A   L   E   A   Y   L    547
AGC CCC CAT GCC CAG CAC ATC TCA GTG AAT GCG AGG AAC GTG GCA TTG GAG GCC TAC CTC 1641

I   K   P   H   S   Y   V   G   L   T   C   T   A   F   Q   R   R   E   G   G    567
ATC AAG CCG CAC AGC TAC GTG GGC CTG ACC TGC ACA GCC TTC CAG AGG AGG GAG GGA GGG 1701

V   P   G   T   R   P   G   S   P   G   Q   N   P   P   P   E   P   E   P   P    587
GTG CCG GGC ACA CGG CCA GGA AGC CCT GGC CAG AAC CCC CCA CCT GAG CCC GAG CCC CCA 1761

A   D   Q   Q   L   R   F   R   C   T   T   G   R   P   N   V   S   L   S   S    607
GCT GAC CAG CAG CTC CGC TTC CGC TGC ACC ACC GGG AGG CCC AAT GTT TCT CTG TCG TCC 1821
```

FIG. 1B-2

```
F   H   I   K   N   S   V   A   L   A   S   I   Q   L   P   P   S   L   F   S    627
TTC CAC ATC AAG AAC AGC GTG GCC CTC GCC TCC ATC CAG CTG CCC CCG AGT CTA TTC TCA 1881

S   L   P   A   A   L   A   P   P   V   P   P   D   C   T   L   Q   L   L   V    647
TCC CTT CCG GCT GCC CTG GCT CCC CCG GTG CCC CCA GAC TGC ACC CTG CAA CTG CTC GTC 1941

F   R   N   G   R   L   F   H   S   H   S   N   T   S   R   P   G   A   A   G    667
TTC CGA AAT GGC CGC CTC TTC CAC AGC CAC AGC AAC ACC TCC CGC CCT GGA GCT GCT GGG 2001

P   G   K   R   R   G   V   A   T   P   V   I   F   A   G   T   S   G   C   G    687
CCT GGC AAG AGG CGT GGC GTG GCC ACC CCC GTC ATC TTC GCA GGA ACC AGT GGC TGT GGC 2061

V   G   N   L   T   E   P   V   A   V   S   L   R   H   W   A   E   G   A   E    707
GTG GGA AAC CTG ACA GAG CCA GTG GCC GTT TCG CTG CGG CAC TGG GCT GAG GGA GCC GAA 2121

P   V   A   A   W   W   S   Q   E   G   P   G   E   A   G   G   W   T   S   E    727
CCT GTG GCC GCT TGG TGG AGC CAG GAG GGG CCC GGG GAG GCT GGG GGC TGG ACC TCG GAG 2181
```

FIG. 1B-3

G C Q L R S S Q P N V S A L H C Q H L G 747
GGC TGC CAG CTC CGC TCC AGC CAG CCC AAT GTC AGC GCC CTG CAC TGC CAG CAC TTG GGC 2241

N V A V L M E L S A F P R E V G G A G A 767
AAT GTG GCC GTG CTC ATG GAG CTG AGC GCC TTT CCC AGG GAG GTG GGG GGC GCC GGG GCA 2301

TM I
G L H P V V Y P C T A L L L L C L F A T 787
GGG CTG CAC CCC GTG GTA TAC CCC TGC ACG GCC TTC CTG CTG CTC TGC CTC TTC GCC ACC 2361

TM II
I I T Y I L N H S S I R V S R K G W H M 807
ATC ATC ACC TAC ATC CTC AAC CAC AGC TCC ATC CGT GTG TCC CGG AAA GGC TGG CAC ATG 2421

L L N L C F H I A M T S A V F A G G I T 827
CTG CTG AAC TTG TGC TTC CAC ATA GCC ATG ACC TCT GCT GTC TTT GCG GGG GGC ATC ACA 2481

TM III
L T N Y Q M V C Q A V G I T L H Y S S L 847
CTC ACC AAC TAC CAG ATG GTC TGC CAG GCG GTG GGC ATC ACC CTG CAC TAG TCC TCC CTA 2541

S T L L W M G V K A R V L H K E L T W R 867
TCC ACG CTG CTC TGG ATG GGC GTG AAG GCG CGA GTG CTC CAT AAG GAG CTC ACC TGG AGG 2601

A P P P Q E G D P A L P T P S P M L R F 887
GCA CCC CCT CCG CAA GAA GGG GAC CCC GCT CTG CCT ACT CCC AGT CCT ATG CTC CGG TTC 2661

Y L I A G G I P L I I C G I T A A V N I 907
TAT TTG ATC GCT GGA GGG ATT CCA CTC ATT ATC TGT GGC ATC ACA GCT GCA GTC AAC ATC 2721

TM V

H N Y R D H S P Y C W L V W R P S L G A 927
CAC AAC TAG CGG GAC CAC AGC CCC TAC TGC TGG CTG GTG TGG CGT CCA AGC CTT GGC GCC 2781

F Y I P V A L I L L I T W I Y F L C A G 947
TTC TAG ATC CCT GTG GCT TTG ATT CTG CTC ATC ACC TGG ATC TAT TTC CTG TGC GCC GGG 2841

L R L R G P L A Q N P K A G N S R A S L 967
CTA CGC TTA CGG GGT CCT CTG GCA CAG AAC CCC AAG GCG GGC AAC AGC AGG GCC TCC CTG 2901

E A G E E L R G S T R L R G S G P L L S 987
GAG GCA GGG GAG GAG CTG AGG GGT TCC ACC AGG CTC AGG GGC AGC GGC CCC CTC CTG AGT 2961

FIG. 1C-2

```
D   S   G   S   L   L   A   T   G   S   A   R   V   G   T   P   G   P   P   E    1007
GAC TCA GGT TCC CTT CTT GCT ACT GGG AGC GCG CGA GTG GGG ACG CCC GGG CCC CCG GAG  3021
                                                     TM VI
D   G   D   S   L   Y   S   P   G   V   Q   L   G   A   L   V   T   T   H   F    1027
GAT GGT GAC AGC CTC TAT TCT CCG GGA GTC CAG CTA GGG GCG CTG GTG ACC ACG CAC TTC  3081

L   Y   L   A   M   W   A   C   G   A   L   A   V   S   Q   R   W   L   P   R    1047
CTG TAG TTG GCC ATG TGG GCC TGC GGG GCT CTG GCA GTG TCC CAG CGC TGG CTG CCC CGG  3141
TM VII
V   V   C   S   C   L   Y   G   V   A   A   S   A   L   G   L   F   V   F   T    1067
GTG GTG TGC AGC TGC TTG TAC GGG GTG GCA GCC TCC GCC CTG GGC CTC TTC GTC TTC ACT  3201

H   H   C   A   R   R   R   D   V   R   A   S   W   R   A   C   C   P   P   A    1087
CAC CAC TGT GCC AGG CGG AGG GAC GTG AGA GCC TCG TGG CGC GCC TGC TGC CCC CCT GCC  3261

S   P   A   A   P   H   A   P   P   R   A   L   P   A   A   A   E   D   G   S    1107
TCT CCC GCG GCC CCC CAT GCC CCG CCC CGG GCC CTG CCC GCC GCC GCA GAG GAC GGT TCC  3321

P   V   F   G   E   G   P   P   S   L   K   S   S   P   S   G   S   S   G   H    1127
CCG GTG TTC GGG GAG GGG CCC CCC TCC CTC AAG TCC TCC CCA AGC GGC AGC AGC GGC CAT  3381

P   L   A   L   G   P   C   K   L   T   N   L   Q   L   A   Q   S   Q   V   C    1147
```

```
CCG CTG GCT CTG GGC CCC TGC AAG CTC ACC AAC CTG CAG CTG GCC CAG AGT GAG GTG TGC   3441

 E   A   G   A   A   A   G   G   E   G   E   P   E   P   A   G   T   R   G   N   1167
GAG GCG GGG GCG GCG GCC GGC GGG GAA GGA GAG CCG GAG CCG GCG GGC ACC CGG GGA AAC   3501

 L   A   H   R   H   P   N   N   V   H   H   G   R   R   A   H   K   S   R   A   1187
CTC GCC CAC CGC CAC CCC AAC AAC GTG CAC CAC GGG CGT CGG GCG CAC AAG AGC CGG GCC   3561

 K   G   H   R   A   G   E   A   C   G   K   N   R   L   K   A   L   R   G   G   1207
AAG GGA CAC CGC GCG GGG GAG GCC TGC GGC AAG AAC CGG CTC AAG GCC CTG CGC GGG GGC   3621

 A   A   G   A   L   E   L   L   S   S   E   S   G   S   L   H   N   S   P   T   1227
GCG GCG GGG GCG CTG GAG CTG CTG TCC AGC GAG AGC GGC AGT CTG CAC AAC AGC CCC ACC   3681

 D   S   Y   L   G   S   S   R   N   S   P   G   A   G   L   Q   L   E   G   E   1247
GAC AGC TAC CTG GGC AGC AGC CGC AAC AGC CCG GGC GCC GGC CTG CAG CTG GAA GGC GAG   3741

 P   M   L   T   P   S   E   G   S   D   T   S   A   A   P   L   S   E   A   G   1267
CCC ATG CTC ACG CCG TCC GAG GGC AGC GAC ACC AGC GCC GCG CCG CTT TCT GAG GCG GGC   3801
```

FIG. 1D-1

```
 R   A   G   Q   R   R   S   A   S   R   D   S   L   K   G   G   G   A   L   E   1287
CGG GCA GGC CAG CGC CGC AGC GCC AGC CGC GAC AGT CTC AAG GGC GGC GGC GCG CTG GAG  3861

 K   E   S   H   R   R   S   Y   P   L   N   A   A   S   L   N   G   A   P   K   1307
AAG GAG AGC CAT CGC CGC TCG TAC CCG CTC AAC GCC GCC AGC CTA AAC GGC GCC CCC AAG  3921

 G   G   K   Y   D   D   V   T   L   M   G   A   E   V   A   S   G   G   C   M   1327
GGG GGC AAG TAC GAC GAC GTC ACC CTG ATG GGC GCG GAG GTA GCC AGC GGC GGC TGC ATG  3981

 K   T   G   L   W   K   S   E   T   T   V   *                                   1339
AAG ACC GGA CTC TGG AAG AGC GAA ACT ACC GTC TAA                                  4017

GGTGGGGCGGGCGACGCGGTAGACGGGCTGGCCACGCGGCTCGTTCCCCGCTCCTCGGGGCCCTCCAAGGTGTCTCCG

TAGTCAGCAGGTTGGAGGCAGAGCAGCCGATGGCTGGAGGAAGCCCACAGGCGGATGTTCCCCACTTGCCTAGAGGGCA

TCCCTCTGGGGTAGCGACAGACAATCCCAGAAACACGCATAATACATTTCCGTCCAGCCCGGGGCAGTCTGACTGTCGG

TGCCCTCCCAGGAACGGGGAAGGCCTCCGTCTGTGTGAAAGGGCACAGCACATCCCAGGTGCACCCTCCCCAAGTACTC

CCACCCCGCCTACTGTCCATGCGGCCTCACTGGGGGCCATCAGCCTCACCAGCAAAGCAGAGATGAGAGCGTGGGAACT
```

FIG. 1D-2

GTGTTCTTTCCTCCCTGCCCTCTACTGATTTCAGCCCAGCCCCTGCCTAGATCCTAGGTCCCTTTTCCTCCCGAGTTTG

GCTGGCACGAGAGCTAGCCCAGCACATGAAGCAGGTGATGTTAAGTCACAAGGTGCTGCTTTTCAGATCCACTATGCAA

GAGGGGAGGGTGGGGCCACGTGAAAGGCAGCTCTAGACATCAACCAGTCCTGGGGGAGGGGAGTGGGAACCGGGCACAA

CTAGGAACAATGCCACCATTCCCACAGGAGTGGTACTTAAACCAGACAGCAGGGTTCAGAGGTGGCACACCGGGACAAA

GCTGAGGCCCTGCACCTCAACAGCTGACTGCCAGGTGCCTGTGGGTGAACTGAGGGGAGTAGAGGGAGAGGGCAGGTGG

AACTGGGGCAGAATCTAGTCATGCCCTAAAGCTAGTCCTGTAAACAATGGTGCCCCAGAAAGCTGCAGGTGGTGTTTGG

AGAAGCAGTTACTTTTCAGTTACAAGACCCATCTCCCTAGTCTCAGCCTTACAACACCACGGGACTAAGGAAGAGCACT

TCCTTGCCTCCGTAAGGCCAGAGGAAGAACCATCCCAATCATTTGATCTCCAGCTCCACAGTAGAGAGAAACCTACAAA

ATGTCAAACCAGCTTCCCGACTCCCAGGAGCTCAAGCCAAGCCCAGAGGCAGTGGCTGGGGTCCCTGCAGGTCATGAGG

GGCCTATGCCTTTACTCCTTTTAAACACCAGCACCCGTCTTTTCCCCAACCTAAAACCAACCACCAGCATTTCACTACA

FIG. 1D-3

GGACCAAATGGAAMCCGAGGGAMCCCTGGGTCTTGGGAAGAACAMCAGGAAACCAAGGTCTGMCCTAGGGTTCCCTCCC

AGTCTTCACATCACTYTGGCCTCATCMCCAAGGTGMCAGAGGACACAGGGGAGGGGGAAAACCCACACACACTCCTTGG

AATGGGTCCTGTTATTTATGCTTGCTGCMCAGACATATTAGAAGAAAAAAAAAAAGCTTTGTATTATTCTTCCACATAT

GCTGGCTGCTGTTAACACACCCTGCCAATGCCTTAGCACTGGAGAGCTTTTTGCAATATGCTGGGGAAAGGGGAGGGAG

GGAATGAAAGTGCCAAAGAAAACATGTTTTTAAGAACTCGGGTTTTATACAATAGAATGTTTTCTAGCAGATGCCTCTT

GTTTTAATATATTAAAATTTTGCAAAGCCCTTTGAAGNATAAAAAAANAGGGCAAACGCTAGACTAGTCTAGAGAAAAA

ACCTCCCAGGNTTCCCCCTAANAACTGGGGCGTAGTGTCCCTATNAACG

FIG. 1E

Consensus 'Consensus #1' : When all match the residue of the Consensus show the residue of the Consensus otherwise show '.'.

Decoration 'Decoration #1' : Shade (with solid black) residues that match the Consensus exactly.

| | Kidney | Brain | Heart | Pool Liver | Liver 200 | Liver 260 | LF 079 | LF 190 | LF 191 | LF 194 | Quiescent Stellate | Passaged Stellate | Stellate | Stellate/FBS | NonCult Hepatocytes | Hep-1 Control | Hep-2 PMA/Ion 6 hr. | Hep-3 TGF 24 hrs. | Hep-4 TGF 48 hrs. |
|---|---|---|---|---|---|---|---|---|---|---|---|---|---|---|---|---|---|---|---|
| Ave 1571 | 35 | 33 | 26 | 28 | 30 | 29 | 25 | 30 | 25 | 31 | 32 | 23 | 25 | 22 | 31 | 31 | 32 | 33 | 30 |
| Ave Beta2 | 21 | 22 | 18 | 18 | 19 | 17 | 19 | 23 | 19 | 24 | 21 | 19 | 21 | 17 | 18 | 17 | 17 | 18 | 17 |
| □Rel Exp | 3 | 18 | 119 | 50 | 18 | 18 | 709 | 265 | 617 | 370 | 31 | 1746 | 1552 | 2091 | 7 | 2 | 2 | 1 | 4 |

| | Brain | Heart | Liver | Lung | Kidney | Sm. Intestine | Muscle | Spinal Cord | Spleen | Sham-12 | Sham-16 | Sham-18 | BDL-9 | BDL-13 | 179-15 7w. Con | 179-17 7w. Serum | 179-18 7w. Serum | 179-22 7w. Con | 179-23 7w. Serum | 179-24 7w. Serum |
|---|---|---|---|---|---|---|---|---|---|---|---|---|---|---|---|---|---|---|---|---|
| Ave 15571 | 24 | 34 | 31 | 24 | 35 | 34 | 30 | 25 | 30 | 31 | 29 | 34 | 31 | 30 | 32 | 36 | 30 | 32 | 30 | 30 |
| Ave rGAPDH | 16 | 18 | 18 | 20 | 21 | 19 | 15 | 17 | 16 | 21 | 20 | 22 | 22 | 23 | 19 | 21 | 19 | 20 | 20 | 19 |
| □Rel Exp | 626 | 1 | 27 | 7256 | 4 | 3 | 0 | 268 | 8 | 119 | 403 | 20 | 284 | 781 | 22 | 5 | 72 | 18 | 81 | 70 |

| | 602-1 CCL4 24 hrs. | 602-2 CCL4 24 hrs. | 602-5 Con. 24 hrs. | 602-8 CCL4 48 hrs. | 602-9 CCL4 48 hrs. | 602-12 Con. 48 hrs. | 593-1 CCL4 6w.dls.24h | 593-3 CCL4 6w.dls.24h | 593-5 Con. for #1 and 3 | 593-6 Con. for #1 and 3 | 593-7 CCL4 6w.dls.48h | 593-8 CCL4 6w.dls.48h | 593-9 CCL4 6w.dls.48h | 593-10 Con. for #7-9 |
|---|---|---|---|---|---|---|---|---|---|---|---|---|---|---|
| Ave r15571 | 34 | 34 | 38 | 32 | 29 | 35 | 40 | 37 | 33 | 30 | 32 | 29 | 29 | 31 |
| Ave rGAPDH | 17 | 18 | 21 | 18 | 18 | 20 | 21 | 21 | 23 | 21 | 21 | 18 | 18 | 22 |
| □Rel Exp | 1 | 2 | 1 | 8 | 55 | 3 | 0 | 2 | 123 | 149 | 37 | 111 | 73 | 326 |

NUCLEIC ACID ENCODING 15571, A GPCR-LIKE MOLECULE OF THE SECRETIN-LIKE FAMILY

CROSS-REFERENCE TO RELATED APPLICATIONS

This application is a continuation-in-part of U.S. Utility application Ser. No. 09/515,781, filed Feb. 29, 2000, now abandoned, which claims the benefit of U.S. Provisional Application Ser. No. 60/146,916, filed Aug. 3, 1999, and entitled "Novel GPCR Molecules of the Secretin Family and Uses Thereof," the contents of which are both herein incorporated by reference in their entirety.

FIELD OF THE INVENTION

The invention relates to novel GPCR-like nucleic acid sequences and proteins. Also provided are vectors, host cells, and recombinant methods for making and using the novel molecules.

BACKGROUND OF THE INVENTION

G-protein coupled receptors (GPCRs) constitute a major class of proteins responsible for transducing a signal within a cell (Strosberg (1991) *Eur. J. Biochem.* 196:1–10; Kerlavage (1991) *Curr. Opin. Struct. Biol.* 1:394–401; Probst et al. (1992) *DNA Cell Biol.* 11:1–20; Savarese et al. (1992) *Biochem* 283:1–9). GPCRs have three structural domains: an amino terminal extracellular domain; a transmembrane domain containing seven transmembrane segments, three extracellular loops, and three intracellular loops; and a carboxy terminal intracellular domain. Upon binding of a ligand to an extracellular portion of a GPCR, a signal is transduced within the cell that results in a change in a biological or physiological property of the cell. GPCRs, along with G-proteins and effectors (intracellular enzymes and channels modulated by G-proteins), are the components of a modular signaling system that connects the state of intracellular second messengers to extracellular inputs.

GPCR genes and gene-products are potential causative agents of disease (Spiegel et al. (1993) *J. Clin. Invest.* 92:1119–1125; McKusick et al. (1993) *J. Med. Genet.* 30:1–26). Specific defects in the rhodopsin gene and the V2 vasopressin receptor gene have been shown to cause various forms of retinitis pigmentosum (Nathans et al. (1992) *Annu. Rev. Genet.* 26:403–424) and nephrogenic diabetes insipidus (Holtzman et al. (1993) *Hum. Mol. Genet.* 2:1201–1204). These receptors are of critical importance to both the central nervous system and peripheral physiological processes. Evolutionary analyses suggest that the ancestor of these proteins originally developed in concert with complex body plans and nervous systems.

In addition to variability among individuals in their responses to drugs, several definable diseases arise from disorders of receptor function or receptor-effector systems. The loss of a receptor in a highly specialized signaling system may cause a relatively limited phenotypic disorder, such as the genetic deficiency of the androgen receptor in the testicular feminization syndrome (Griffin et al. (1995) *The Metabolic and Molecular Bases of Inherited Diseases* 7:2967–2998). Deficiencies of more widely used signaling systems have a broader spectrum of effects, as are seen in myasthenia gravis or some forms of insulin-resistant diabetes mellitus, which result from autoimmune depletion of nicotinic cholinergic receptors or insulin receptors, respectively. A lesion in a component of a signaling pathway that is used by many receptors can cause a generalized endocrinopathy. Heterozygous deficiency in $G_5$, the G protein that activates adenylyl cyclase in all cells, causes multiple endocrine disorders; the disease is termed *pseudohpoparathyroidism type* 1*a* (Spiegel et al. (1995) *The Metabolic and Molecular Bases of Inherited Diseases* 7:3073–3089). Homozygous deficiency in $G_5$ would presumably be lethal.

The expression of aberrant or ectopic receptors, effectors, or coupling proteins potentially can lead to supersensitivity, subsensitivity, or other untoward responses. Among the most interesting and significant events is the appearance of aberrant receptors as products of oncogenes, which transform otherwise normal cells into malignant cells. Virtually any type of signaling system may have oncogenic potential. G proteins can themselves be oncogenic when either overexpressed or constitutively activated by mutation (Lyons et al (1990) *Science* 249:655–659). In particular, the calcitonin receptor is a target for treatment of Paget's disease of the bone; the receptor for glucagon-like peptide 1 is a target for non-insulin dependent diabetes mellitus; parathyroid hormone is involved in calcium homeostasis. Antagonists of the parathyroid hormone receptor are of potential clinical use in the treatment of hyperparathyroidism and short-term hypercalcemic states.

The GPCR protein superfamily can be divided into five families: Family I, receptors typified by rhodopsin and the β2-adrenergic receptor and currently represented by over 200 unique members (Dohlman et al. (1991) *Annu. Rev. Biochem.* 60:653–688); Family II, the parathyroid hormone/calcitonin/secretin receptor family/Class B Secretin-like Family (Juppner et al. (1991) *Science* 254:1024–1026; Lin et al. (1991) *Science* 254:1022–1024); Family III, the metabotropic glutamate receptor family (Nakanishi (1992) *Science* 258 597:603); Family IV, the cAMP receptor family, important in the chemotaxis and development of *D. discoideum* (Klein et al. (1988) *Science* 241:1467–1472); and Family V, the fungal mating pheromone receptors such as STE2 (Kwjan (1992) *Annu. Rev. Biochem.* 61:1097–1129).

G proteins represent a family of heterotrimeric proteins composed of α, β, and γ subunits that bind guanine nucleotides. These proteins are usually linked to cell surface receptors, e.g., receptors containing seven transmembrane segments. Following ligand binding to the GPCR, a conformational change is transmitted to the G protein, which causes the α-subunit to exchange a bound GDP molecule for a GTP molecule and to dissociate from the βγ-subunits. The GTP-bound form of the α-subunit typically functions as an effector-modulating moiety, leading to the production of second messengers, such as cAMP (e.g., by activation of adenyl cyclase), diacylglycerol or inositol phosphates. Greater than different types of α-subunits are known in humans. These subunits associate with a smaller pool of β and γ subunits. Examples of mammalian G proteins include Gi, Go, Gq, Gs, and Gt. G proteins are described extensively in Lodish et al.(1995) *Molecular Cell Biology* (Scientific American Books Inc., New York, N.Y.), the contents of which are incorporated herein by reference. GPCRs, G proteins and G protein-linked effector and second messenger systems have been reviewed in Watson et al., eds. (1994) *The G-Protein Linked Receptor Fact Book* (Academic. Press, NY).

GPCRs are a major target for drug action and development. Accordingly, it is valuable to the field of pharmaceutical development to identify and characterize previously unknown GPCRs. The present invention advances the state of the art by providing previously unidentified human GPCR-like sequences.

SUMMARY OF THE INVENTION

Isolated nucleic acid molecules corresponding to GPCR-like nucleic acid sequences are provided. Additionally, amino acid sequences corresponding to the polynucleotides are encompassed. In particular, the present invention provides for isolated nucleic acid molecules comprising nucleotide sequences encoding the amino acid sequence shown in SEQ ID NO:2 or the nucleotide sequence encoding the DNA sequence deposited in a bacterial host with ATCC as Accession Number PTA-1660. Further provided are GPCR-like polypeptides having an amino acid sequence encoded by a nucleic acid molecule described herein, such as the sequence shown in SEQ ID NO:1.

The present invention also provides vectors and host cells for recombinant expression of the nucleic acid molecules described herein, as well as methods of making such vectors and host cells and for using them for production of the polypeptides or peptides of the invention by recombinant techniques.

The GPCR-like molecules of the present invention find use in identifying compounds that act as agonists and antagonists and modulate the expression of the novel receptors. Furthermore, compounds that modulate expression of the receptors for treatment and diagnosis of GPCR-related disorders are also encompassed. The molecules are useful for the treatment of immune, hematologic, fibrotic, hepatic, and respiratory disorders, including, but not limited to, atopic conditions, such as asthma and allergy, including allergic rhinitis, psoriasis, the effects of pathogen infection, chronic inflammatory diseases, organ-specific autoimmunity, graft rejection, graft versus host disease, cystic fibrosis, and liver fibrosis. Disorders associated with the following cells or tissues are also encompassed: lymph node; spleen; thymus; brain; lung; skeletal muscle; fetal liver; tonsil; colon; heart; liver; peripheral blood mononuclear cells (PBMC); $CD34^+$; bone marrow cells; neonatal umbilical cord blood (CB $CD34^+$); leukocytes from G-CSF treated patients (mPB leukocytes); $CD14^+$ cells; monocytes; hepatic stellate cells; fibrotic liver; kidney; spinal cord; and dermal and lung fibroblasts.

Accordingly, in one aspect, this invention provides isolated nucleic acid molecules encoding GPCR-like proteins or biologically active portions thereof, as well as nucleic acid fragments suitable as primers or hybridization probes for the detection of GPCR-like-encoding nucleic acids. The invention also features isolated or recombinant GPCR-like proteins and polypeptides. Preferred GPCR-like proteins and polypeptides possess at least one biological activity possessed by naturally occurring GPCR-like proteins.

Variant nucleic acid molecules and polypeptides substantially homologous to the nucleotide and amino acid sequence set forth in the Sequence Listing are encompassed by the present invention. Additionally, fragments and substantially homologous fragments of the nucleotide and amino acid sequence are provided.

Antibodies and antibody fragments that selectively bind the GPCR-like polypeptides and fragments are provided. Such antibodies are useful for detecting the presence of receptor protein in cells or tissues. Antibodies can also be used to assess receptor expression in disease states, to assess normal and aberrant subcellular localization of cells in the various tissues in an organism. Antibodies are also useful as diagnostic tools as an immunological marker for aberrant receptor protein.

In one embodiment, the uses can be applied in a therapeutic context in which treatment involves modulating receptor function. An antibody can be used, for example, to block ligand binding. Antibodies can be prepared against specific fragments containing sites required for function or against intact receptor associated with a cell. The GPCR-like modulators include GPCR-like proteins, nucleic acid molecules, peptides, or other small molecules.

The present invention also provides a diagnostic assay for identifying the presence or absence of a genetic lesion or mutation characterized by at least one of the following: (1) aberrant modification or mutation of a gene encoding a GPCR-like protein; (2) misregulation of a gene encoding a GPCR-like protein; and (3) aberrant post-translational modification of a GPCR-like protein, wherein a wild-type form of the gene encodes a protein with a GPCR-like activity.

In another aspect, the invention provides a method for identifying a compound that binds to or modulates the activity of a GPCR-like protein. In general, such methods entail measuring a biological activity of a GPCR-like protein in the presence and absence of a test compound and identifying those compounds that alter the activity of the GPCR-like protein.

The invention also features methods for identifying a compound that modulates the expression of GPCR-like genes by measuring the expression of the GPCR-like sequences in the presence and absence of the compound.

Other features and advantages of the invention will be apparent from the following detailed description and claims.

BRIEF DESCRIPTION OF THE DRAWINGS

FIGS. 1A-1-1E provide the full-length nucleotide (SEQ ID NO:1) and amino acid (SEQ ID NO:2) sequences for clone 15571. The position of each of the seven transmembrane domains, TM I-VII, is shown as a boxed sequence as follows: TM I, 772–793; TM II, 807–826; TM III, 836–855; TM IV, 887–904; TM V, 925–947; TM VI, 1021–1040; and TM VII, 1048–1066.

FIGS. 2A-1-2D show an alignment of the sequence encompassing the region of the seven transmembrane domain (7tm) of h15571 and the following human GPCRs of the Class B secretin-like family: CD97R (leukocyte antigen CD97, Swiss-Prot accession number P48960) (SEQ ID NO:9); CGRR (a calcitonin gene-related peptide type 1 receptor; Swiss-Prot accession number Q16602) (SEQ ID NO:10); CRF1 (corticotropin releasing factor receptor 1; Swiss-Prot accession numbers P34998 and Q13008) (SEQ ID NO:11); CRF2 (corticotropin releasing factor receptor 2; Swiss-Prot accession numbers Q13324, Q99431, and O43461) (SEQ ID NO:12); CTR (calcitonin receptor;Swiss-Prot accession number P30988) (SEQ ID NO:13); EMR1 (cell surface glycoprotein EMR1; Swiss-Prot accession number Q14246) (SEQ ID NO:14); GIPR (glucose-dependent insulinotropic polypeptide receptor; Swiss-Prot accession numbers P48546, Q16400, and Q14401) (SEQ ID NO:15); GLRP (glucagon-like peptide 1 receptor; Swiss-Prot accession numbers P43220 and Q99669) (SEQ ID NO:16); GLR (glucagon receptor; Swiss-Prot accession number P47871) (SEQ ID NO:17); GRFR (growth hormone-releasing hormone receptor; Swiss-Prot accession numbers Q02643 and Q99863) (SEQ ID NO:18); PACR (pituitary adenylate cyclase activating polypeptide type I receptor; Swiss-Prot accession number P41586) (SEQ ID NO: 19); PTR2 (parathyroid hormone receptor; Swiss-Prot accession number P49190) (SEQ ID NO:20); PTRR (parathyroid hormone/parathyroid hormone-related peptide receptor; Swiss-Prot accession number Q03431) (SEQ ID NO:21) SCRC (secretin receptor; Swiss-Prot accession numbers P47872, Q13213, and Q12961) (SEQ ID NO:22); VIPR (pituitary adenylate cyclase activating polypeptide type II receptor; Swiss-Prot accession numbers P32241 and Q15871) (SEQ ID NO:23); and, VIPS (pituitary adenylate cyclase activating polypeptide type III receptor; Swiss-Prot accession numbers P41587, Q15870, and Q13053) (SEQ ID NO:24).

DETAILED DESCRIPTION OF THE INVENTION

Figures 1, 2A:
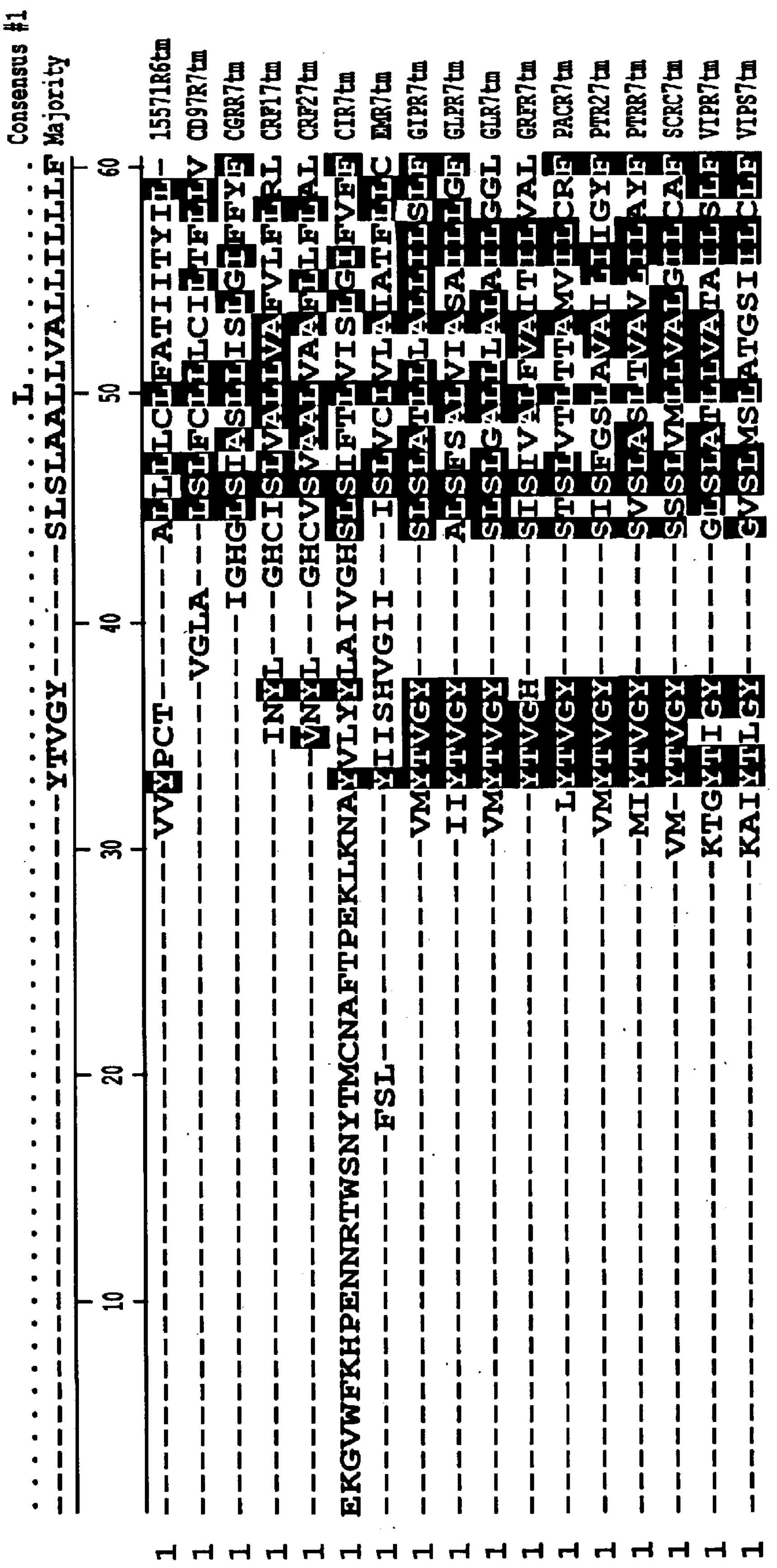
Figures 2, 2A:
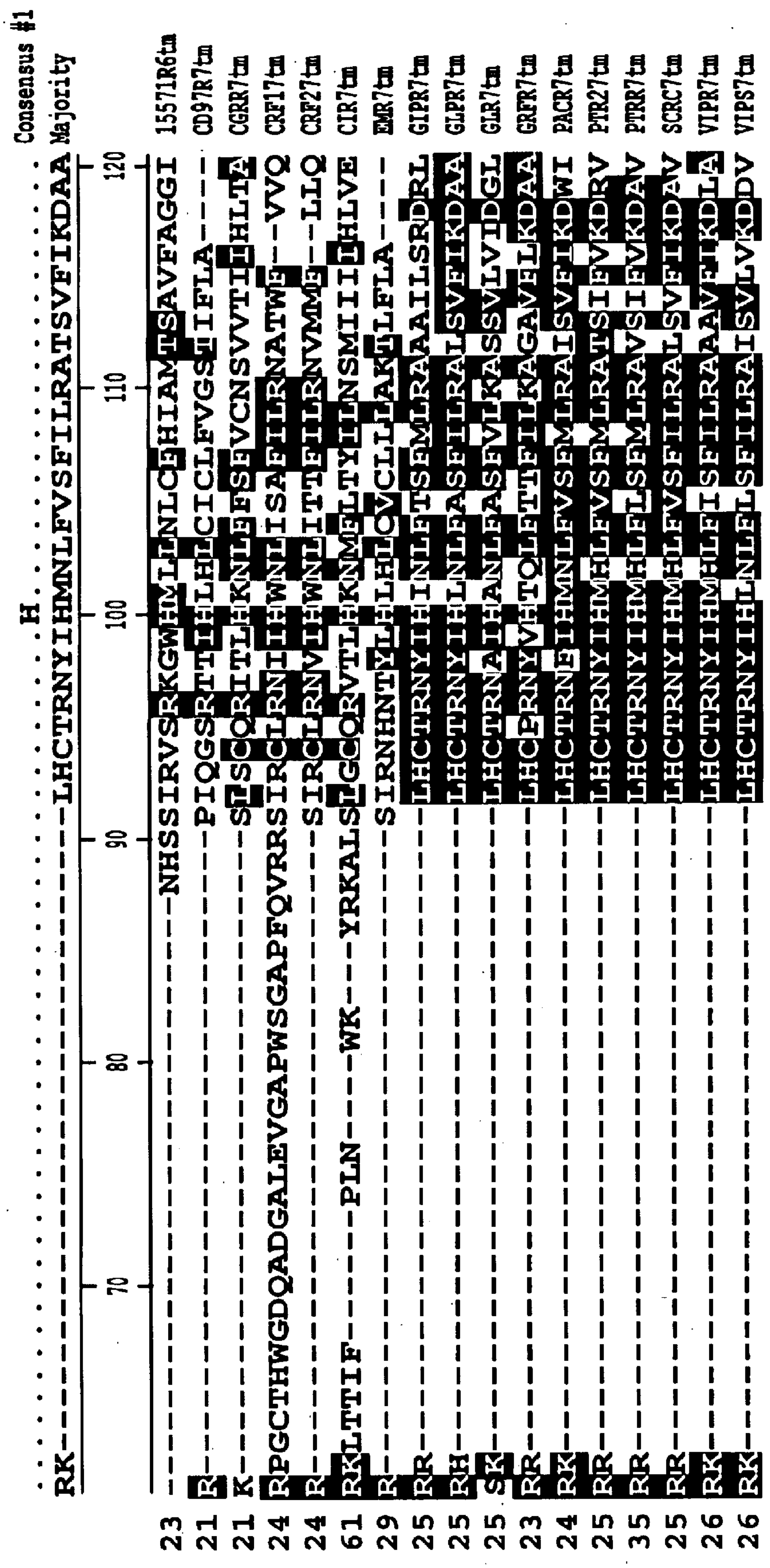
Figures 1, 2B:
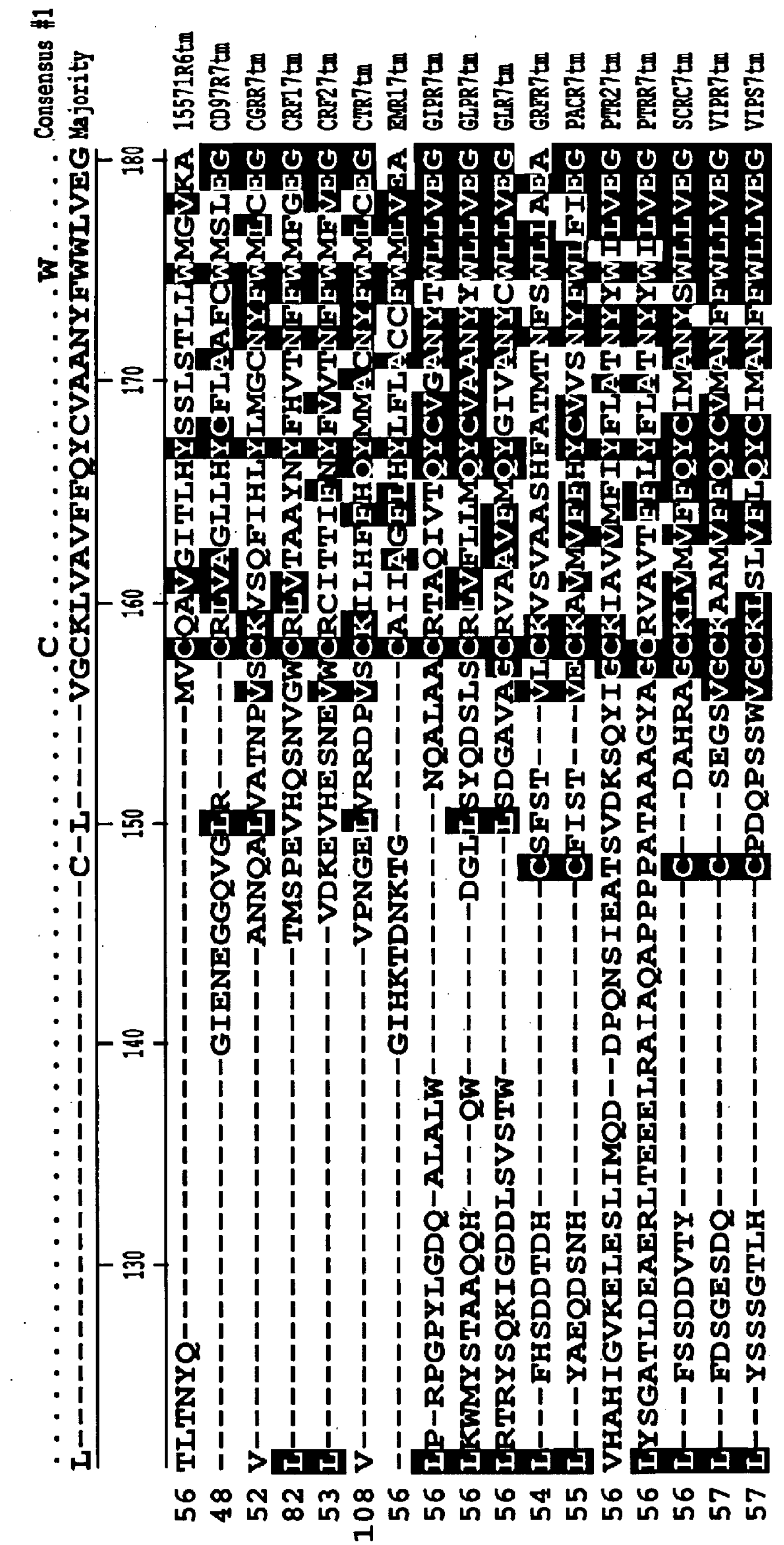
Figures 2, 2B:
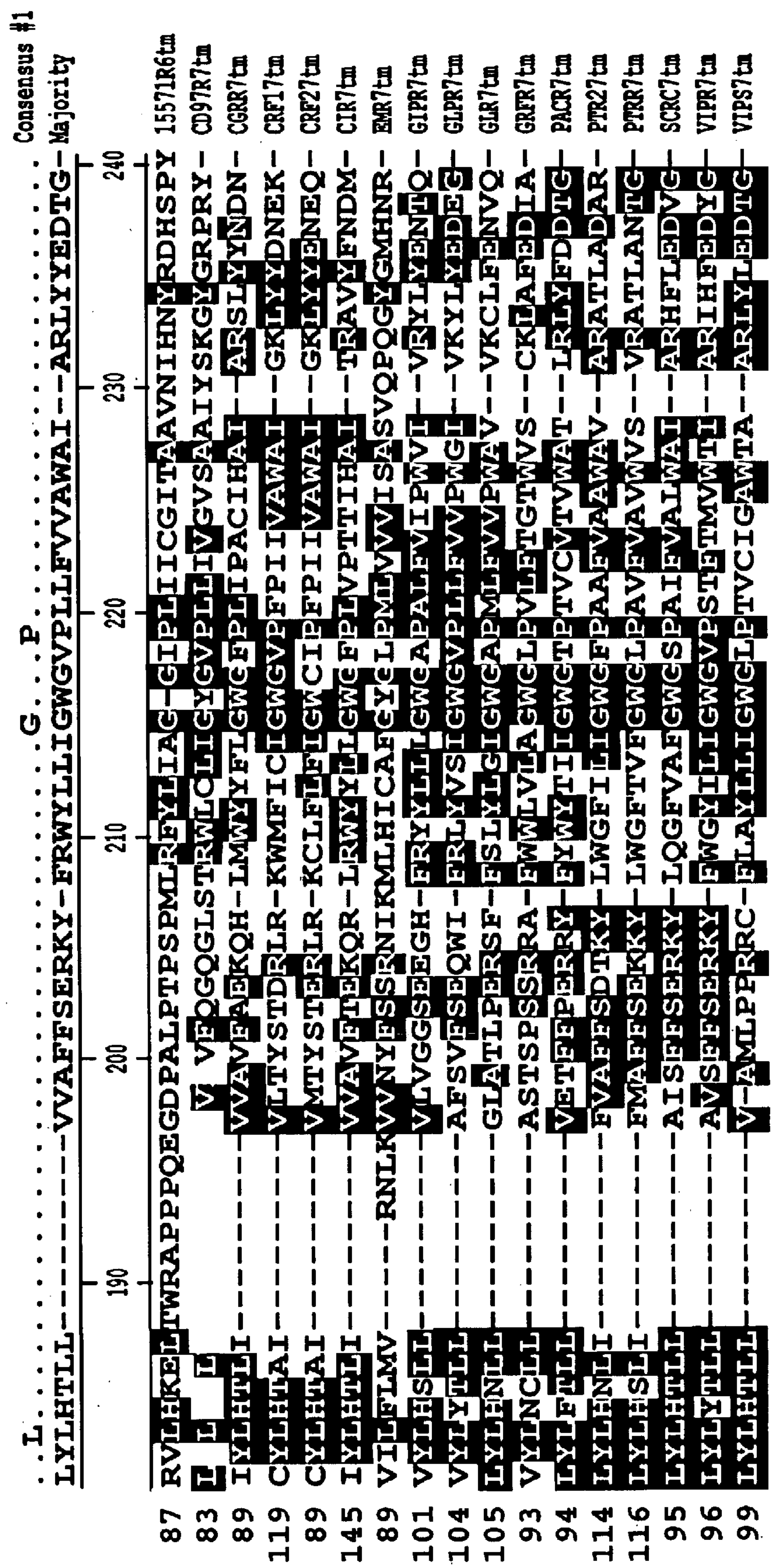
Figures 1, 2C:
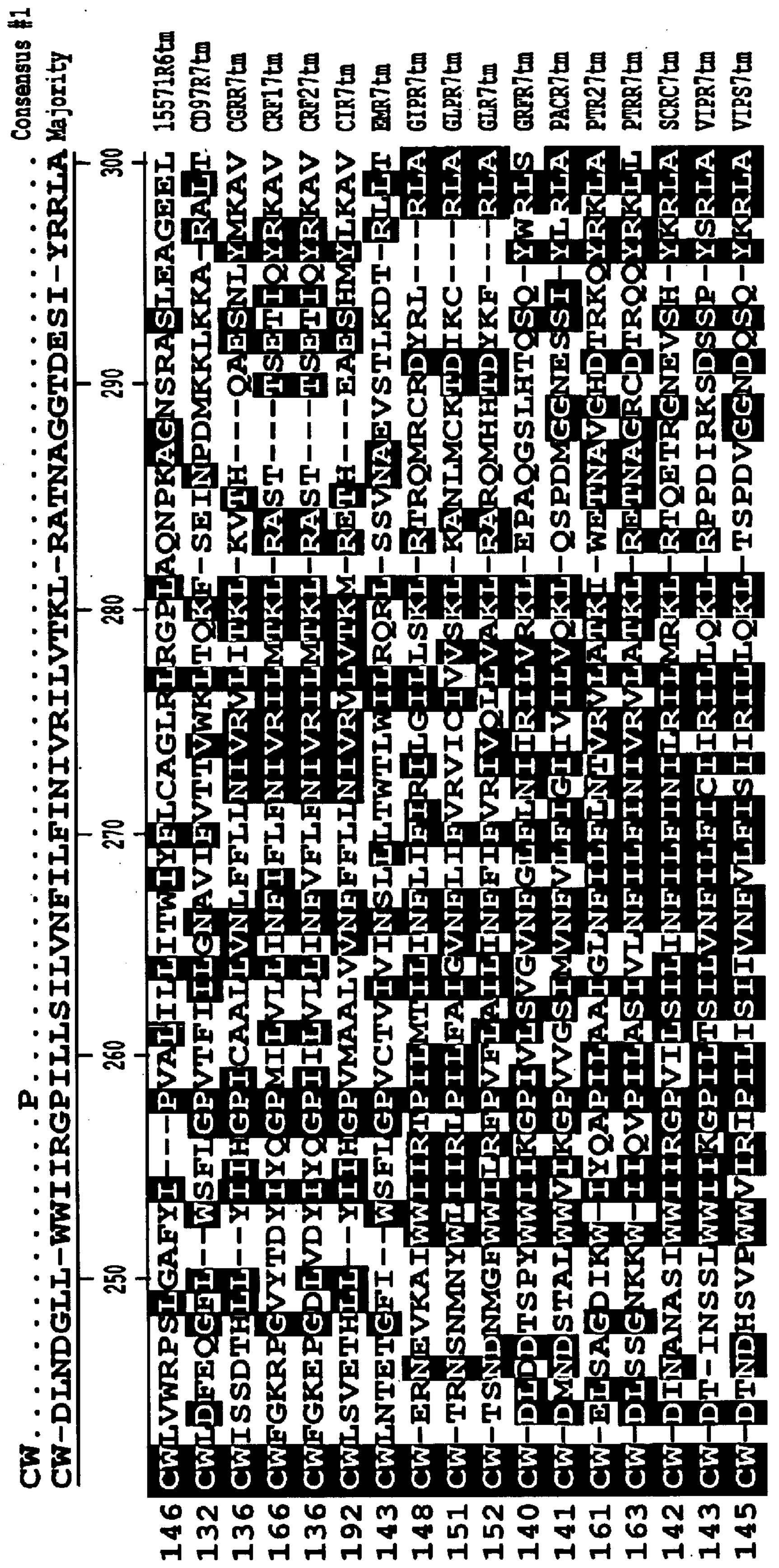
Figures 2, 2C:
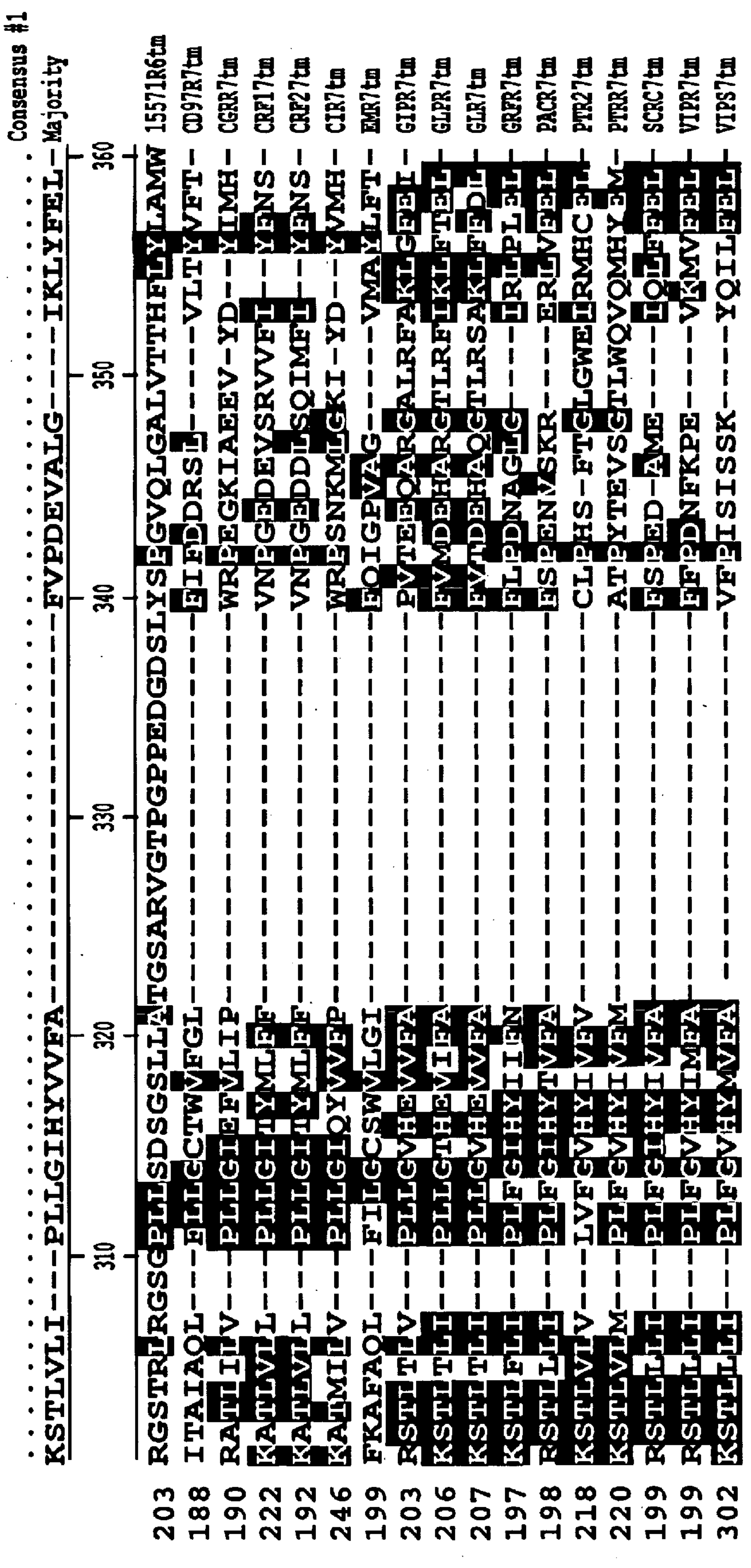

The present invention provides GPCR-like molecules. By "GPCR-like molecules" is intended a novel human sequence referred to as h15571, and variants and fragments thereof. These full-length gene sequences or fragments thereof are referred to as "GPCR-like" sequences, indicating they share sequence similarity with GPCR genes. Isolated nucleic acid molecules comprising nucleotide sequences encoding the h15571 polypeptide whose amino acid sequence is given in SEQ ID NO:2, or a variant or fragment thereof, are provided. A nucleotide sequence encoding the h15571 polypeptide is set forth in SEQ ID NO:1. The sequences are members of the secretin-like family of G-protein coupled receptors.

The secretin/VIP (vasoactive intestinal polypeptide) family includes receptors for peptides such as secretin, glucagon, glucagon-like peptide 1 (GLP-1), gastric inhibitory peptide, parathyroid hormone, VIP, pituitary adenlylate cyclase activating polypeptide (PACAP), calcitonin, and growth hormone releasing hormone. VIP has a wide profile of physiological actions. In the periphery, VIP induces relaxation in smooth muscle, inhibits secretion in certain tissues such as the stomach, stimulates secretion in tissues such as the intestinal epithelium, pancreas, and gall bladder, and modulates activity of cells in the immune system. In the central nervous system, VIP has a wide range of excitatory and inhibitory actions.

Members of the Class B Secretin-like family of GPCRs (Juppner et al. (1991) *Scienece* 254:1024–1026; Hamann et. al. (1996) *Genomics* 32:144–147) include: calcitonin receptor, calcitonin gene-related peptide receptor, corticotropin releasing factor receptor types 1 and 2, gastric inhibitory polypeptide receptor, glucagon receptor, glucagon-like peptide 1 receptor, growth hormone-releasing hormone receptor, parathyroid hormone/parathyroid homerelated peptide types 1 and 2, pituitary adenylate cyclase activating polypeptide receptor, secretin receptor, vasoactive intestinal peptide receptor types 1 and 2, insects diuretic hormone receptor, *Caenorhabditis elegans* putative receptor C13B9.4 (Swiss-Prot accession number Q09460), *Caenorhabditis elegans* putative receptor ZK64.3 (Swiss-Prot accession numbers P30650 and P30649), human leucocyte antigen CD97(a protein that contains, in its N-terminal section, 3 EGF-like domains) (Swiss-Prot accession number P48960), and mouse cell surface glycoprotein F4/80 (murine EMR1 hormone receptor that contains, in its N-terminal section, 7 EGF-like domains) (GenBank accession-number X93328), human EMR1 (EMR1 hormone receptor containing 6 EGF-like domains) (GenBank accession number X81479), BAI1 (a brain-specific p53-target gene containing thrombospondin type 1 repeats) (GenBank accession number AB005297), GPR56 (GenBank accession number AF106858), HE6 (a human receptor having an amino terminal region with identity to highly glycosylated mucin-like cell surface molecules) (GenBank accession number X81892), alpha-latrotxin receptors, and MEGF2 (a human protein containing EGF-like motifs) (GenBank accession number AB011536).

The receptor-like proteins of the invention function as GPCR-like proteins that participate in signaling pathways. As used herein, a "signaling pathway" refers to the modulation (e.g., stimulation or inhibition) of a cellular function/activity upon the binding of a ligand to the GPCR-like protein. Examples of such functions include mobilization of intracellular molecules that participate in a signal transduction pathway, e.g., phosphatidylinositol 4,5-bisphosphate ($PIP_2$), inositol 1,4,5-triphosphate ($IP_3$), and adenylate cyclase; polarization of the plasma membrane; production or secretion of molecules; alteration in the structure of a cellular component; cell proliferation, e.g., synthesis of DNA; cell migration; cell differentiation; and cell survival.

The response mediated by the receptor-like proteins of the invention depends on the type of cell. For example, in some cells, binding of a ligand to the receptor-like protein may stimulate an activity such as release of compounds, gating of a channel, cellular adhesion, migration, differentiation, etc., through phosphatidylinositol or cyclic AMP (cAMP) metabolism and turnover while in other cells, the binding of the ligand will produce a different result. Regardless of the cellular activity/response modulated by the receptor-like protein, it is universal that the protein is a GPCR-like protein and interacts with G proteins to produce one or more secondary signals, in a variety of intracellular signal transduction pathways, e.g., through phosphatidylinositol or cyclic AMP metabolism and turnover, in a cell.

As used herein, "phosphatidylinositol turnover and metabolism" refers to the molecules involved in the turnover and metabolism of phosphatidylinositol 4,5-bisphosphate ($PIP_2$) as well as to the activities of these molecules. $PIP_2$ is a phospholipid found in the cytosolic leaflet of the plasma membrane. Binding of ligand to the receptor activates, in some cells, the plasma-membrane enzyme phospholipase C that in turn can hydrolyze $PIP_2$ to produce 1,2-diacylglycerol (DAG) and inositol 1,4,5-triphosphate ($IP_3$). Once formed, $IP_3$ can diffuse to the endoplasmic reticulum surface where it can bind an $IP_3$ receptor, e.g., a calcium channel protein containing an $IP_3$ binding site. $IP_3$ binding can induce opening of the channel, allowing calcium ions to be released into the cytoplasm. $IP_3$ can also be phosphorylated by a specific kinase to form inositol 1,3,4,5-tetraphosphate ($IP_4$), a molecule that can cause calcium entry into the cytoplasm from the extracellular medium. $IP_3$ and $IP_4$ can subsequently be hydrolyzed very rapidly to the inactive products inositol 1,4-biphosphate ($IP_2$) and inositol 1,3,4-triphosphate, respectively. These inactive products can be recycled by the cell to synthesize $PIP_2$. The other second messenger produced by the hydrolysis of $PIP_2$, namely 1,2-diacylglycerol (DAG), remains in the cell membrane where it can serve to activate the enzyme protein kinase C. Protein kinase C is usually found soluble in the cytoplasm of the cell, but upon an increase in the intracellular calcium concentration, this enzyme can move to the plasma membrane where it can be activated by DAG. The activation of protein kinase C in different cells results in various cellular responses such as the phosphorylation of glycogen synthase, or the phosphorylation of various transcription factors, e.g., NF-κB. The language "phosphatidylinositol activity", as used herein, refers to an activity of $PIP_2$ or one of its metabolites.

Another signaling pathway in which the receptor-like proteins may participate is the cyclic AMP (cAMP) turnover pathway. As used herein, "cAMP turnover and metabolism" refers to the molecules involved in the turnover and metabolism of cAMP as well as to the activities of these molecules. Cyclic AMP is a second messenger produced in response to ligand-induced stimulation of certain G-protein coupled receptors. In the cAMP signaling pathway, binding of a ligand to a GPCR can lead to the activation of the enzyme adenyl cyclase, which catalyzes the synthesis of cAMP. The newly synthesized cAMP can in turn activate a cAMP-dependent protein kinase. This activated kinase can phosphorylate a voltage-gated potassium channel protein, or an associated protein, and lead to the inability of the potassium channel to open during an action potential. The inability of the potassium channel to open results in a decrease in the outward flow of potassium, which normally repolarizes the membrane of a neuron, leading to prolonged membrane depolarization.

The disclosed invention relates to methods and compositions for the modulation, diagnosis, and treatment of immune, hematologic, fibrotic, inflammatory, liver, and respiratory disorders. Such immune disorders include, but are not limited to, chronic inflammatory diseases and disorders, inflammatory bowel disease, such as Crohn's disease and ulcerative colitis, rheumatoid arthritis, including Lyme disease, insulin-dependent diabetes, organ-specific autoimmunity, including multiple sclerosis, Hashimoto's thyroiditis and Grave's disease, contact dermatitis, psoriasis, graft rejection, graft versus host disease, sarcoidosis, atopic conditions, such as asthma and allergy, including allergic rhinitis, gastrointestinal allergies, including food allergies, eosinophilia, conjunctivitis, glomerular nephritis, certain pathogen susceptibilities such as helminthic (e.g., leishmaniasis), certain viral infections, including HIV, HBV, HCV, and bacterial infections, including tuberculosis and lepromatous leprosy.

Respiratory disorders include, but are not limited to, apnea, asthma, particularly bronchial asthma, berillium disease, bronchiectasis, bronchitis, bronchopneumonia, cystic fibrosis, diphtheria, dyspnea, emphysema, chronic obstructive pulmonary disease, allergic bronchopulmonary aspergillosis, pneumonia, acute pulmonary edema, pertussis, pharyngitis, atelectasis, Wegener's granulomatosis, Legionnaires disease, pleurisy, rheumatic fever, and sinusitis.

Fibrotic disorders or diseases include fibrosis in general, e.g., chronic pulmonary obstructive disease; ideopathic pulmonary fibrosis; crescentic glomerulofibrosis; sarcoidosis; cystic fibrosis; fibrosis/cirrhosis, including cirrhosis secondary to chronic alcoholism, cirrhosis secondary to hepatitis type B or hepatitis type C, and primary biliary cirrhosis; liver disorders disclosed below, particularly liver fibrosis; and other fibrotic diseases; as well as in the treatment of bums and scarring.

Disorders involving the liver include, but are not limited to, hepatic injury; jaundice and cholestasis, such as bilirubin and bile formation; hepatic failure and cirrhosis, such as cirrhosis, portal hypertension, including ascites, portosystemic shunts, and splenomegaly; infectious disorders, such as viral hepatitis, including hepatitis A-E infection and infection by other hepatitis viruses, clinicopathologic syndromes, such as the carrier state, asymptomatic infection, acute viral hepatitis, chronic viral hepatitis, and fulminant hepatitis; autoimmune hepatitis; drug- and toxin-induced liver disease, such as alcoholic liver disease; inborn errors of metabolism and pediatric liver disease, such as hemochromatosis, Wilson disease, $\alpha_1$-antitrypsin deficiency, and neonatal hepatitis; intrahepatic biliary tract disease, such as secondary biliary cirrhosis, primary biliary cirrhosis, primary sclerosing cholangitis, and anomalies of the biliary tree; circulatory disorders, such as impaired blood flow into the liver, including hepatic artery compromise and portal vein obstruction and thrombosis, impaired blood flow through the liver, including passive congestion and centrilobular necrosis and peliosis hepatis, hepatic vein outflow obstruction, including hepatic vein thrombosis (Budd-Chiari syndrome) and veno-occlusive disease; hepatic disease associated with pregnancy, such as preeclampsia and eclampsia, acute fatty liver of pregnancy, and intrehepatic cholestasis of pregnancy; hepatic complications of organ or bone marrow transplantation, such as drug toxicity after bone marrow transplantation, graft-versus-host disease and liver rejection, and nonimmunologic damage to liver allografis; tumors and tumorous conditions, such as nodular hyperplasias, adenomas, and malignant tumors, including primary carcinoma of the liver and metastatic tumors.

Hematologic disorders include but are not limited to anemias including chemotherapy-induced anemia, sickle cell and hemolytic anemia, hemophilias including types A and B, leukemias, thalassemias, spherocytosis, Von Willebrand disease, chronic granulomatous disease, glucose-6-phosphate dehydrogenase deficiency, thrombosis, clotting factor abnormalities and deficiencies including factor VIII and IX deficiencies, hemarthrosis, hematemesis, hematomas, hematuria, hemochromatosis, hemoglobinuria, hemolytic-uremic syndrome, thrombocytopenias including chemotherapy-induced thrombocytopenia, HIV-associated thrombocytopenia, hemorrhagic telangiectasia, idiopathic thrombocytopenic purpura, thrombotic microangiopathy, hemosiderosis, chemotherapy induced neutropenias. Other disorders include polycythemias, including polycythemia vera, secondary polycythemia, and relative polycythemia, neutropenias, including chemotherapy-induced neutropenia, chronic idiopathic neutropenia, Felty's syndrome, neutropenias resulting from acute infectious diseases, lymphoma or aleukemic lymphocytic leukemia with neutropenia, myelodysplastic syndrome, rheumatic disease induced neutropenias such as systemic lupus, erythematosus, rheumatoid arthritis, and polymyositis.

A novel human GPCR-like gene sequence, referred to as h15571, is provided. This gene sequence and variants and fragments thereof are encompassed by the term "GPCR-like" molecules or sequences as used herein. The GPCR-like sequences find use in modulating a GPCR-like function. By "modulating" is intended the upregulating or downregulating of a response. That is, the compositions of the invention affect the targeted activity in either a positive or negative fashion.

The GPCR-like gene, designated clone h15571, was identified in human thymus and spleen cDNA libraries. Clone h15571 encodes an approximately 6.09 Kb mRNA transcript having the corresponding cDNA set forth in SEQ ID NO:1. This transcript has a 4014-nucleotide open reading frame (nucleotides 366–4379 of SEQ ID NO:1), which encodes a 1338 amino acid polypeptide (SEQ ID NO:2). The full-length nucleotide sequence and deduced amino acid sequence are shown in FIGS. 1A-1–1E.

An analysis of the full-length h15571 polypeptide (SEQ ID NO:2) predicts that the N-terminal 33 amino acids represent a signal peptide. Thus, the mature polypeptide is predicted to be 1305 amino acids in length (aa 34–1338 of SEQ ID NO:2). Transmembrane domains (TM) at the following positions of the sequence set forth in SEQ ID NO:2 were predicted by MEMSAT as well as by alignment with members of the secretin-like family of GPCRs and visual inspection; TM I, 772–793, TM II, 807–826; TM III, 836–855; TM IV, 887–904; TM V, 925–947; TM VI 1021–1040; and TM VII, 1048–1066. The 7 TM domains are shown as boxed sequences in FIGS. 1A-1–1E. Based on the predicted positions of TM I-VII, the predicted positions of the N-terminus extracellular domain (EC), the extracellular loops (EL) I-III, the intracellular loops (IL) I-III, and the C-terminus intracellular domain (IC) are as follows as shown in the sequence in SEQ ID NO:2: EC, about aa 34–771; EL I, about aa 827–835; EL II, about aa 905–924; EL III, about aa 1041–1048; IL I, about aa 794–806; IL II, about aa 856–886; IL III, about aa 948–1020; and IC, about aa 1067–1338. Prosite program analysis was used to predict various sites within the h15571 protein. N-glycosylation sites were predicted at aa 84–87, 101–104, 162–165, 207–210, 275–278, 336–339, 436–439, 602–605, 659–662, 690–693, 737–740, and 794–797. A glycosaminoglycan attachment site was predicted at aa 684–687. Protein Kinase C phosphorylation sites were predicted at aa 40–42, 43–45, 253–255, 338–340, 400–402, 598–600, 660–662, 698–700, 797–799, 801–803, 865–867, 976–978, 997–999, 1041–1043, 1079–1081, 1116–1118, 1233–1235, 1279–1281, and 1290–1292. Casein Kinase II phosphorylation sites were predicted at aa 69–72, 108–111, 231–234, 456–459, 1225–1228, and 1251–1254. N-myristoylation sites were predicted at aa 36–41, 53–58, 80–85, 98–103, 126–131, 145–150, 165–170, 295–300, 319–324, 392–397, 555–560, 566–571, 682–687, 722–727, 763–768, 825–830, 900–905, 961–966, 990–995, 1016–1021, 1055–1060, 1150–1155, 1163–1168, 1206–1211, 1220–1225, 1232–1237, 1255–1260, 1270–1275, 1304–1309, 1318–1323, and 1325–1330. Amidation sites were predicted at aa 4–7, 668–671, and 1178–1181. A prokaryotic membrane lipoproptein lipid attachment site was predicted at aa 676–686. An RGD cell attachment sequence was predicted at aa 362–364.

Domain matches using HMMER 2.1.1 (Washington University School of Medicine) indicated the presence of several key protein domains. A search of the HMM database using Pfam (Protein Family) indicated the presence of five leucine rich repeat domains, residing at aa 85–108, 109–132, 133–156, 157–180, and 604–630. A leucine rich repeat C-terminal domain was identified at aa 190–240. An immunoglobulin domain was identified at aa 261–330. A latrophilin/CL-1-like GPS domain was identified at aa 706–758. A search of the HMM database using SMART (Simple Modular Architecture Research Tool) revealed the following domain matches: four leucine rich repeat typical-2 subfamily domains were identified, residing at aa 82–106, 107–130, 131–154, and 155–178. Two leucine rich repeat SDS22-like subfamily domains were identified, residing at aa 107–128 and 131–157. A leucine rich repeat ribonuclease inhibitor type domain was identified at aa 131–157. A leucine rich repeat C-terminal domain was identified at aa 190–240. An immunuglobulin C-2 type domain was identified at aa 259–335. An immunoglobulin 3-C domain was identified at aa 253–346. A hormone receptor domain was identified at aa 349–426. A G-protein coupled receptor proteolytic site domain was identified at aa 706–758.

ProDom analysis indicates that the h15571 polypeptide has regions sharing similarity with other GPCRs. Amino acid residues 367–1077 share approximately 33% identity with portions of a consensus sequence for Family II GPCRs including calcitonin receptor (CALR), corticotrophin releasing factor receptor (CRFR), and parathyroid hormone/parathyroid hormone related receptor (PTRR). ProDom analysis also indicates that the h15571 polypeptide has regions sharing similarity with several other proteins. Amino acid residues 84–131, 85–155, 110–179, and 134–187 share approximately 43%, 36%, 34%, and 24% identity with amino acid residues 26–73, 3–73, 4–73, and 4–57, respectively, of a consensus sequence for the rat MEGF5 glycoprotein EGF-like domain. Amino acid residues 89–237 share approximately 30% identity with a consensus sequence for a family that groups together the CYAA, ESA8, and CD 14 proteins. Amino acid residues 182–356 share approximately 21% identity with a protein encoded by the *C. elegans* YK6G3.3, which also has multiple leucine-rich repeats. Amino acid residues 88–221 share approximately 32% identity with a leucine-rich repeat protein. Amino acid residues 37–176 share approximately 23% identity with the *C. elegans* C44H4.1 protein (Accession No. CABD1867). Amino acid residues 180–237 and 860–883 share an identity of approximately 37% and 45%, respectively, with aa residues 4–64 and 166–187 of the human KIAA0644 protein.

Figure 2D:
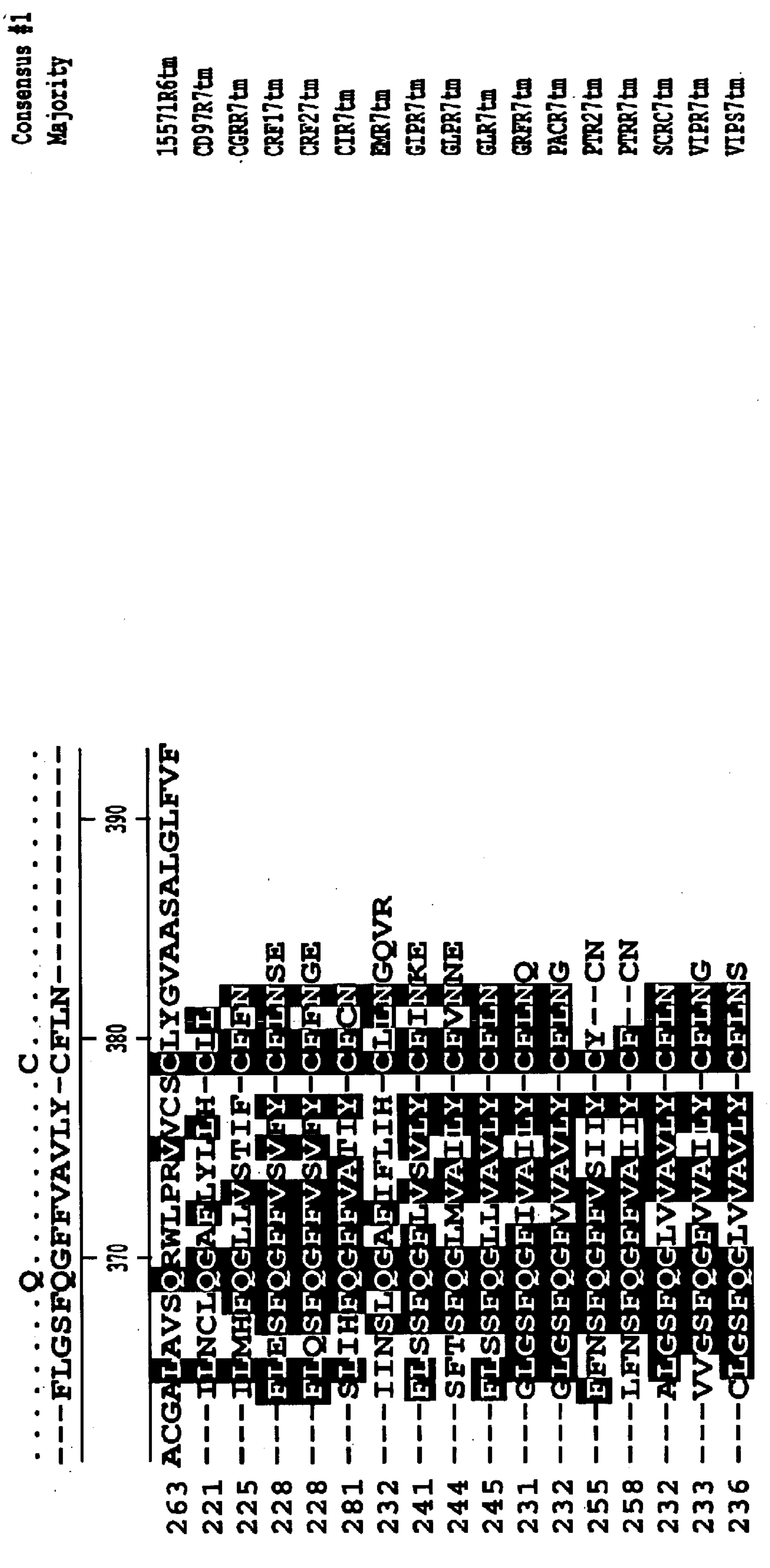

Shown in FIGS. 2A-1–2D is an alignment of the seven transmembrane (7 TM) domains of h15571 with several members of the Class B secretin-like family of GPCRs. Based on sequence homology of the 7 TM domains, h15571 appears to be related to a subfamily of the Class B Secretin-like Family of GPCRs. The members of this subfamily share similar sequences in the 7 TM domains that are distinct from other members of the secretin-like family. This subfamily includes CD97, EMR1, BAI1, GPR56, HE6, alpha-latrotoxin receptors, MEGF2, and two putative GPCRs identified by sequencing the *C. elegans* genome (GenBank™ accession numbers Z54306 and U39848). The members of this subfamily are further characterized by the presence of an extremely large N-terminal extracellular region (containing, for example, several hundred amino acid residues, e.g., at least 200, 250, 300, 350, 400, 450, 500, 550, 600, 650, 700, 750, 800, 850, 900, 950, or 1000, or more amino acid residues). The members of this family of molecules also share a box of four conserved cysteine residues in the N-terminus of TM I, which is the purported area of proteolytic cleavage for at least two members, CD97 and the latrotoxin receptor. Further, there is a cellular adhesion domain (e.g., mucin-like, thrombospondin-like, EGF-like, or lectin-like) seen in the N-terminus of members of this subfamily. See Liu et al. (1999) *Genomics* 55:296–305.

h15571 shares with other members of this subfamily a large N-terminal extracellular region (approximately 738 aa residues), but differs by the presence of two of the four conserved cysteine residues in the N-terminus of TM I. Further, no known cellular adhesion domain has been identified in the N-terminus of h15571. The 7 TM region of h15571 (from about aa 772 to about 1066 of SEQ ID NO:2) shows the highest homology (approximately 19.4%) with the CD97 7 TM region.

A plasmid containing the h15571 cDNA insert was deposited with American Type Culture Collection (ATCC), 10801 University Boulevard, Manassas, Va., on Apr. 5, 2000, and assigned Accession Number PTA-1660. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

The GPCR-like sequences of the invention are members of a family of molecules (the "secretin-like receptor family") having conserved functional features. The term "family" or "subfamily" when referring to the proteins and nucleic acid molecules of the invention is intended to mean two or more proteins or nucleic acid molecules having sufficient amino acid or nucleotide sequence identity as defined herein. Such family members can be naturally occurring and can be from either the same or different species. For example, a family can contain a first protein of murine origin and a homologue of that protein of human origin, as well as a second, distinct protein of human origin and a murine homologue of that protein. Members of a family may also have common functional characteristics.

Preferred GPCR-like polypeptides of the present invention have an amino acid sequence sufficiently identical to the amino acid sequence of SEQ ID NO:2. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain (e.g., leucine rich repeat domain, immunoglobulin domain, transmembrane receptor domain, G-protein receptor domain, etc.) and/or common functional activity. For example, amino acid or nucleotide sequences that contain a common structural domain having at least about 45%, 55%, 60% or 65% identity, preferably at least about 70%, 75%, 80%, identity, more preferably at least about 85%, 90%, 91%, 92%, 93%, 94%, 95%, 96%, 97%, 98%, or 99% identity are defined herein as sufficiently identical.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A preferred, nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873–5877. Such an algorithm is incorporated into the NBLAST and XBLAST programs of Altschul et al. (1990) *J. Mol. Biol.* 215:403. BLAST nucleotide searches can be performed with the NBLAST program, score=100, wordlength=12, to obtain nucleotide sequences homologous to GPCR-like nucleic acid molecules of the invention. BLAST protein searches can be performed with the XBLAST program, score=50, wordlength=3, to obtain amino acid sequences homologous to GPCR-like protein molecules of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., XBLAST and NBLAST) can be used. See http:H/www.ncbi.nlm.nih.gov. Another preferred, non-limiting example of a mathematical algorithm utilized for the comparison of sequences is the algorithm of Myers and Miller (1988) CABIOS4:11–17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used. An additional preferred program is the Pairwise Alignment Program (Sequence Explorer), using default parameters.

Accordingly, another embodiment of the invention features isolated GPCR-like proteins and polypeptides having a GPCR-like protein activity. As used interchangeably herein, a "GPCR-like protein activity", "biological activity of a GPCR-like protein", or "functional activity of a GPCR-like protein" refers to an activity exerted by a GPCR-like protein, polypeptide, or nucleic acid molecule on a GPCR-like responsive cell as determined in vivo, or in vitro, according to standard assay techniques. A GPCR-like activity can be a direct activity, such as an association with or an enzymatic activity on a second protein, or an indirect activity, such as a cellular signaling activity mediated by interaction of the GPCR-like protein with a second protein. In a preferred embodiment, a GPCR-like activity includes at least one or more of the following activities: (1) modulating (i.e., stimulating and/or enhancing or inhibiting) cellular proliferation, differentiation, and/or function (in the cells and organs in which it is expressed, for example, lymph node; spleen; thymus; brain; lung; skeletal muscle; fetal liver; tonsil; colon; heart; liver; peripheral blood mononuclear cells (PBMC); $CD34^+$; bone marrow cells; neonatal umbilical cord blood (CB $CD34^+$); leukocytes from G-CSF treated patients (mPB leukocytes); $CD14^+$ cells; monocytes; hepatic stellate cells; fibrotic liver; kidney; spinal cord; dermal and lung fibroblasts; and the K562, HEK 293, Jurkat, and HL60 cell lines; (2) modulating a GPCR-like response; (3) modulating an inflammatory or immune response; (4) modulating a respiratory response; and (5) binding a GPCR-like receptor ligand.

An "isolated" or "purified" GPCR-like nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated"

nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated GPCR-like nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A GPCR-like protein that is substantially free of cellular material includes preparations of GPCR-like protein having less than about 30%, 20%, 10%, or 5% (by dry weight) of non-GPCR-like protein (also referred to herein as a "contaminating protein"). When the GPCR-like protein or biologically active portion thereof is recombinantly produced, preferably, culture medium represents less than about 30%, 20%, 10%, or 5% of the volume of the protein preparation. When GPCR-like protein is produced by chemical synthesis, preferably the protein preparations have less than about 30%, 20%, 10%, or 5% (by dry weight) of chemical precursors or non-GPCR-like chemicals.

Various aspects of the invention are described in further detail in the following subsections.

I. Isolated Nucleic Acid Molecules

One aspect of the invention pertains to isolated nucleic acid molecules comprising nucleotide sequences encoding GPCR-like proteins and polypeptides or biologically active portions thereof, as well as nucleic acid molecules sufficient for use as hybridization probes to identify GPCR-like-encoding nucleic acids (e.g., GPCR-like mRNA) and fragments for use as PCR primers for the amplification or mutation of GPCR-like nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

Nucleotide sequences encoding the GPCR-like proteins of the present invention include the sequence set forth in SEQ ID NO:1, the nucleotide sequence of the cDNA insert of the plasmid deposited with the ATCC as Patent Deposit No. PTA-1660 (the "cDNA of ATCC PTA-1660"), and complements thereof. By "complement" is intended a nucleotide sequence that is sufficiently complementary to a given nucleotide sequence such that it can hybridize to the given nucleotide sequence to thereby form a stable duplex. The corresponding amino acid sequence-for the polypeptide encoded by these nucleotide sequences is set forth in SEQ ID NO:2.

Nucleic acid molecules that are fragments of these GPCR-like nucleotide sequences are also encompassed by the present invention. By "fragment" is intended a portion of the nucleotide sequence encoding a GPCR-like protein. A fragment of a GPCR-like nucleotide sequence may encode a biologically active portion of a GPCR-like protein, or it may be a fragment that can be used as a hybridization probe or PCR primer using methods disclosed below. A biologically active portion of a GPCR-like protein can be prepared by isolating a portion of one of the GPCR-like nucleotide sequences of the invention, expressing the encoded portion of the GPCR-like protein (e.g., by recombinant expression in vitro), and assessing the activity of the encoded portion of the GPCR-like protein. Nucleic acid molecules that are fragments of a GPCR-like nucleotide sequence comprise at least about 15, 20, 50, 75, 100, 200, 300, 350, 400, 450, 500, 550, 600, 650, 700, 750, 800, 850, 900, 950, 1000, 1250, 1500, 1750, 2000, 2500, 3000, 3500, 4000, 4500, 5000, 5250, 5500, 5750, or 6000 nucleotides, or up to the number of nucleotides present in a full-length GPCR-like nucleotide sequence disclosed herein (6090 nucleotides for the h15571 sequence set forth in SEQ ID NO:1) depending upon the intended use.

It is understood that isolated fragments include any contiguous sequence not disclosed prior to the invention as well as sequences that are substantially the same and which are not disclosed. Accordingly, if an isolated fragment is disclosed prior to the present invention, that fragment is not intended to be encompassed by the invention. When a sequence is not disclosed prior to the present invention, an isolated nucleic acid fragment is at least about 12, 15, 20, 25, or 30 contiguous nucleotides. Other regions of the nucleotide sequence may comprise fragments of various sizes, depending upon potential homology with previously disclosed sequences.

A fragment of a GPCR-like nucleotide sequence that encodes a biologically active portion of a GPCR-like protein of the invention will encode at least about 15, 25, 30, 50, 75, 100, 125, 150, 175, 200, 300, 400, 500, 600, 700, 800, 900, 1000, 1050, 1100, 1150, 1200, 1250, 1300 contiguous amino acids, or up to the total number of amino acids present in a full-length GPCR-like polypeptide of the invention (1338 amino acids for the full-length h15571 protein set forth in SEQ ID NO:2). Fragments of a GPCR-like nucleotide sequence that are useful as hybridization probes for PCR primers generally need not encode a biologically active portion of a GPCR-like protein.

Nucleic acid molecules that are variants of the GPCR-like nucleotide sequences disclosed herein are also encompassed by the present invention. "Variants" of the GPCR-like nucleotide sequences include those sequences that encode the GPCR-like proteins disclosed herein but that differ conservatively because of the degeneracy of the genetic code. These naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the GPCR-like proteins disclosed in the present invention as discussed below. Generally, nucleotide sequence variants of the invention will have at least about 45%, 55%, 60%, 65%, 70%, 75%, 80%, 85%, 90%, 91%, 92%, 93%, 94%, 95%, 96%, 97%, 98%, or 99% identity to a particular nucleotide sequence disclosed herein. A variant GPCR-like nucleotide sequence will encode a GPCR-like protein that has an amino acid sequence having at least about 45%, 55%, 60%, 65%, 70%, 75%, 80%, 85%, 90%, 91%, 92%, 93%, 94%, 95%, 96%, 99% identity to the amino acid sequence of a GPCR-like protein disclosed herein.

In addition to the GPCR-like nucleotide sequence shown in SEQ ID NO:1 and the nucleotide sequence of the cDNA of ATCC PTA-1660, it will be appreciated by those skilled in the art that DNA sequence polymorphisms that lead to changes in the amino acid sequences of GPCR-like proteins may exist within a population (e.g., the human population). Such genetic polymorphism in a GPCR-like gene may exist among individuals within a population due to natural allelic variation. An allele is one of a group of genes that occur alternatively at a given genetic locus. As used herein, the terms "gene" and "recombinant gene" refer to nucleic acid molecules comprising an open reading frame encoding a GPCR-like protein, preferably a mammalian GPCR-like protein. As used herein, the phrase "allelic variant" refers to a nucleotide sequence that occurs at a GPCR-like locus or to a polypeptide encoded by the nucleotide sequence. Such natural allelic variations can typically result in 1–5% variance in the nucleotide sequence of the GPCR-like gene. Any and all such nucleotide variations and resulting amino acid polymorphisms or variations in a GPCR-like sequence that are the result of natural allelic variation and that do not alter the functional activity of GPCR-like proteins are intended to be within the scope of the invention.

Moreover, nucleic acid molecules encoding GPCR-like proteins from other species (GPCR-like homologues), that have a nucleotide sequence differing from that of the GPCR-like sequences disclosed herein, are intended to be within the scope of the invention. For example, nucleic acid molecules corresponding to natural allelic variants and homologues of the human GPCR-like cDNA of the invention can be isolated based on their identity to the human GPCR-like nucleic acid disclosed herein using the human cDNA, or a portion thereof, as a hybridization probe according to standard hybridization techniques under stringent hybridization conditions as disclosed below.

In addition to naturally-occurring allelic variants of the GPCR-like sequences that may exist in the population, the skilled artisan will further appreciate that changes can be introduced by mutation into the nucleotide sequences of the invention thereby leading to changes in the amino acid sequence of the encoded GPCR-like proteins, without altering the biological activity of the GPCR-like proteins. Thus, an isolated nucleic acid molecule encoding a GPCR-like protein having a sequence that differs from that of SEQ ID NO:2 can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, preferably, conservative amino acid substitutions may be made at one or more predicted, preferably nonessential amino acid residues. A "nonessential" amino acid residue is a residue that can be altered from the wild-type sequence of a GPCR-like protein (e.g., the sequence of SEQ ID NO:2) without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Such substitutions would not be made for conserved amino acid residues, or for amino acid residues residing within a conserved motif, such as the 7 transmembrane receptor domains (i.e., TM I, 772–793, TM II, 807–826; TM III, 836–855; TM IV, 887–904; TM V, 925–947; TM VI 1021–1040; and TM VII, 1048–1066 of SEQ ID NO:2), where such residues are essential for protein activity.

Alternatively, variant GPCR-like nucleotide sequences can be made by introducing mutations randomly along all or part of a GPCR-like coding sequence, such as by saturation mutagenesis, and the resultant mutants can be screened for GPCR-like biological activity to identify mutants that retain activity. Following mutagenesis, the encoded protein can be expressed recombinantly, and the activity of the protein can be determined using standard assay techniques.

Thus the nucleotide sequences of the invention include the sequences disclosed herein as well as fragments and variants thereof. The GPCR-like nucleotide sequences of the invention, and fragments and variants thereof, can be used as probes and/or primers to identify and/or clone GPCR-like homologues in other cell types, e.g., from other tissues, as well as GPCR-like homologues from other mammals. Such probes can be used to detect transcripts or genomic sequences encoding the same or identical proteins. These probes can be used as part of a diagnostic test kit for identifying cells or tissues that misexpress a GPCR-like protein, such as by measuring levels of a GPCR-like -encoding nucleic acid in a sample of cells from a subject, e.g., detecting GPCR-like mRNA levels or determining whether a genomic GPCR-like gene has been mutated or deleted.

In this manner, methods such as PCR, hybridization, and the like can be used to identify such sequences having substantial identity to the sequences of the invention. See, for example, Sambrook et al. (1989) *Molecular Cloning: Laboratory Manual* (2d ed., Cold Spring Harbor Laboratory Press, Plainview, N.Y.) and Innis, et al. (1990) *PCR Protocols: A Guide to Methods and Applications* (Academic Press, NY). GPCR-like nucleotide sequences isolated based on their sequence identity to the GPCR-like nucleotide sequences set forth herein or to fragments and variants thereof are encompassed by the present invention.

In a hybridization method, all or part of a known GPCR-like nucleotide sequence can be used to screen cDNA or genomic libraries. Methods for construction of such cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.). The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known GPCR-like nucleotide sequence disclosed herein. Degenerate primers designed on the basis of conserved nucleotides or amino acid residues in a known GPCR-like nucleotide sequence or encoded amino acid sequence can additionally be used. The probe typically comprises a region of nucleotide sequence that hybridizes under stringent conditions to at least about 12, preferably about 25, more preferably about 50, 75, 100, 125, 150, 175, 200, 250, 300, 350, or 400 consecutive nucleotides of a GPCR-like nucleotide sequence of the invention or a fragment or variant thereof. Preparation of probes for hybridization is generally known in the art and is disclosed in Sambrook et al. (1989) *Molecular Cloning: A Laboratory Manual* (2d ed., Cold Spring Harbor Laboratory Press, Plainview, N.Y.), herein incorporated by reference.

For example, in one embodiment, a previously unidentified GPCR-like nucleic acid molecule hybridizes under stringent conditions to a probe that is a nucleic acid molecule comprising one of the GPCR-like nucleotide sequences of the invention or a fragment thereof. In another embodiment, the previously unknown GPCR-like nucleic acid molecule is at least about 300, 325, 350, 375, 400, 425, 450, 500, 550, 600, 650, 700, 800, 900, 1000, 2000, 3000, 4000, 5000, or 6000 nucleotides in length and hybridizes under stringent conditions to a probe that is a nucleic acid molecule comprising one of the GPCR-like nucleotide sequences disclosed herein or a fragment thereof.

Accordingly, in another embodiment, an isolated previously unknown GPCR-like nucleic acid molecule of the invention is at least about 300, 325, 350, 375, 400, 425, 450, 500, 550, 600, 650, 700, 800, 900, 1000, 1,100, 1,200, 1,300, or 1,400 nucleotides in length and hybridizes under stringent conditions to a probe that is a nucleic acid molecule comprising one of the nucleotide sequences of the invention, preferably the coding sequence set forth in SEQ ID NO:1, the cDNA of ATCC PTA-1660, or a complement, fragment, or variant thereof.

As used herein, the term "hybridizes under stringent conditions" is intended to describe conditions for hybridization and washing under which nucleotide sequences having at least about 60%, 65%, 70%, preferably 75% identity to each other typically remain hybridized to each other. Such stringent conditions are known to those skilled in the art and can be found in *Current Protocols in Molecular Biology* (John Wiley & Sons, New York (1989)), 6.3.1–6.3.6. A preferred, non-limiting example of stringent hybridization conditions is hybridization in 6×sodium chloride/sodium citrate (SSC) at about 45° C., followed by one or more washes in 0.2×SSC, 0.1% SDS at 50–65° C. In another preferred embodiment, stringent conditions comprise hybridization in 6×SSC at 42° C., followed by washing with 1×SSC at 55° C. Preferably, an isolated nucleic acid molecule that hybridizes under stringent conditions to a GPCR-like sequence of the invention corresponds to a naturally occurring nucleic acid molecule. As used herein, a "naturally occurring" nucleic acid molecule refers to an RNA or DNA molecule having a nucleotide sequence that occurs in nature (e.g., encodes a natural protein).

Thus, in addition to the GPCR-like nucleotide sequences disclosed herein and fragments and variants thereof, the isolated nucleic acid molecules of the invention also encompass homologous DNA sequences identified and isolated from other cells and/or organisms by hybridization with entire or partial sequences obtained from the GPCR-like nucleotide sequences disclosed herein or variants and fragments thereof.

The present invention also encompasses antisense nucleic acid molecules, i.e., molecules that are complementary to a sense nucleic acid encoding a protein, e.g., complementary to the coding strand of a double-stranded cDNA molecule, or complementary to an mRNA sequence. Accordingly, an antisense nucleic acid can hydrogen bond to a sense nucleic acid. The antisense nucleic acid can be complementary to an entire GPCR-like coding strand, or to only a portion thereof, e.g., all or part of the protein coding region (or open reading frame). An antisense nucleic acid molecule can be antisense to a noncoding region of the coding strand of a nucleotide sequence encoding a GPCR-like protein. The noncoding regions are the 5' and 3' sequences that flank the coding region and are not translated into amino acids.

Given the coding-strand sequence encoding a GPCR-like protein disclosed herein (e.g., the coding-strand sequence of SEQ ID NO:1), antisense nucleic acids of the invention can be designed according to the rules of Watson and Crick base pairing. The antisense nucleic acid molecule can be complementary to the entire coding region of GPCR-like mRNA, but more preferably is an oligonucleotide that is antisense to only a portion of the coding or noncoding region of GPCR-like mRNA. For example, the antisense oligonucleotide can be complementary to the region surrounding the translation start site of GPCR-like mRNA. An antisense oligonucleotide can be, for example, about 5, 10, 15, 20, 25, 30, 35, 40, 45, or 50 nucleotides in length. An antisense nucleic acid of the invention can be constructed using chemical synthesis and enzymatic ligation procedures known in the art.

For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, including, but not limited to, for example e.g., phosphorothioate derivatives and acridine substituted nucleotides. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

When used therapeutically, the antisense nucleic acid molecules of the invention are typically administered to a subject or generated in situ such that they hybridize with or bind to cellular mRNA and/or genomic DNA encoding a GPCR-like protein to thereby inhibit expression of the protein, e.g., by inhibiting transcription and/or translation. An example of a route of administration of antisense nucleic acid molecules of the invention includes direct injection at a tissue site. Alternatively, antisense nucleic acid molecules can be modified to target selected cells and then administered systemically. For example, antisense molecules can be linked to peptides or antibodies to form a complex that specifically binds to receptors or antigens expressed on a selected cell surface. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An (α-anomeric nucleic acid molecule forms specific double-stranded hybrids with complementary RNA in which, contrary to the usual β-units, the strands run parallel to each other (Gaultier et al. (1987) *Nucleic Acids Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) FEBS Lett. 215:327–330).

The invention also encompasses ribozymes, which are catalytic RNA molecules with ribonuclease activity that are capable of cleaving a single-stranded nucleic acid, such as an mRNA, to which they have a complementary region. Ribozymes (e.g., hammerhead ribozymes (described in Haselhoff and Gerlach (1988) Nature 334:585–591)) can be used to catalytically cleave GPCR-like mRNA transcripts to thereby inhibit translation of GPCR-like mRNA. A ribozyme having specificity for a GPCR-like-encoding nucleic acid can be designed based upon the nucleotide sequence of a GPCR-like cDNA disclosed herein. (e.g., SEQ ID NO:1). See, e.g., Cech et al., U.S. Pat. No. 4,987,071; and Cech et al., U.S. Pat. No. 5,116,742. Alternatively, GPCR-like mRNA can be used to select a catalytic RNA having a specific ribonuclease activity from a pool of RNA molecules. See, e.g., Bartel and Szostak (1993) *Science* 261:1411–1418.

The invention also encompasses nucleic acid molecules that form triple helical structures. For example, GPCR-like gene expression can be inhibited by targeting nucleotide sequences complementary to the regulatory region of the GPCR-like protein (e.g., the GPCR-like promoter and/or enhancers) to form triple helical structures that prevent transcription of the GPCR-like gene in target cells. See generally Helene (1991) *Anticancer Drug Des.* 6(6):569; Helene (1992) *Ann. N.Y Acad. Sci.* 660:27; and Maher (1992) Bioassays 14(12):807.

In preferred embodiments, the nucleic acid molecules of the invention can be modified at the base moiety, sugar moiety, or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid-phase peptide synthesis protocols as described, for example, in Hyrup et al. (1996), supra; Perry-O'Keefe et al. (1996) *Proc. Natl. Acad. Sci. USA* 93:14670.

PNAs of a GPCR-like molecule can be used in therapeutic and diagnostic applications. For example, PNAs can be used as antisense or antigene agents for sequence-specific modulation of gene expression by, e.g., inducing transcription or translation arrest or inhibiting replication. PNAs of the invention can also be used, e.g., in the analysis of single base pair mutations in a gene by, e.g., PNA-directed PCR clamping; as artificial restriction enzymes when used in combination with other enzymes, e.g., S1 nucleases (Hyrup (1996), supra); or as probes or primers for DNA sequence and hybridization (Hyrup (1996), supra; Perry-O'Keefe et al. (1996), supra).

In another embodiment, PNAs of a GPCR-like molecule can be modified, e.g., to enhance their stability, specificity, or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra; Finn et al. (1996) *Nucleic Acids Res.* 24(17):3357–63; Mag et al. (1989) *Nucleic Acids Res.* 17:5973; and Peterson et al. (1975) *Bioorganic Med. Chem. Lett.* 5:1119.

II. Isolated GPCR-like Proteins and Anti-GPCR-like Antibodies

GPCR-like proteins are also encompassed within the present invention. By "GPCR-like protein" is intended a protein comprising the amino acid sequence set forth in SEQ ID NO:2, as well as fragments, biologically active portions, and variants thereof. "Fragments" or "biologically active portions" include polypeptide fragments suitable for use as immunogens to raise anti-GPCR-like antibodies. Fragments include peptides comprising amino acid sequences sufficiently identical to or derived from the amino acid sequence of a GPCR-like protein, or partial-length protein, of the invention and exhibiting at least one activity of a GPCR-like protein, but which include fewer amino acids than the full-length GPCR-like protein (SEQ ID NO:2) disclosed herein. Typically, biologically active portions comprise a domain or motif with at least one activity of the GPCR-like protein. A biologically active portion of a GPCR-like protein can be a polypeptide which is, for example, 10, 25, 50, 100 or more amino acids in length. Such biologically active portions can be prepared by recombinant techniques and evaluated for one or more of the functional activities of a native GPCR-like protein. As used here, a fragment comprises at least 7 contiguous amino acids of SEQ ID NO:2. The invention encompasses other fragments, however, such as any fragment in the protein greater than 8, 9, 10, or 11 amino acids.

Biologically active fragments (peptides which are, for example, 5, 7, 10, 12, 15, 20, 30, 35, 36, 37, 38, 39, 40, 50, 100 or more amino acids in length) can comprise, for example, a domain or motif, e.g., leucine rich repeats and leucine rich repeat C-terminal domains, latrophilin/CL-1-like GPS domain, immunoglobulin domain, 7 transmembrane receptor domain, and sites for glycosylation, protein kinase C phosphorylation, casein kinase II phosphorylation, glycosaminoglycan attachment, amidation, N-myristoylation, prokaryotic membrane lipoprotein lipid attachment, and RGD cell attachment. Further possible fragments include sites important for cellular and subcellular targeting. Fragments, for example, can extend in one or both directions from the functional site to encompass 5, 10, 15, 20, 30, 40, 50, or up to 100 amino acids. Further, fragments can include sub-fragments of the specific domains mentioned above, which sub-fragments retain the function of the domain from which they are derived. Such domains or motifs and their sub-fragments can be identified by means of routine computerized homology searching procedures.

Figure 3:
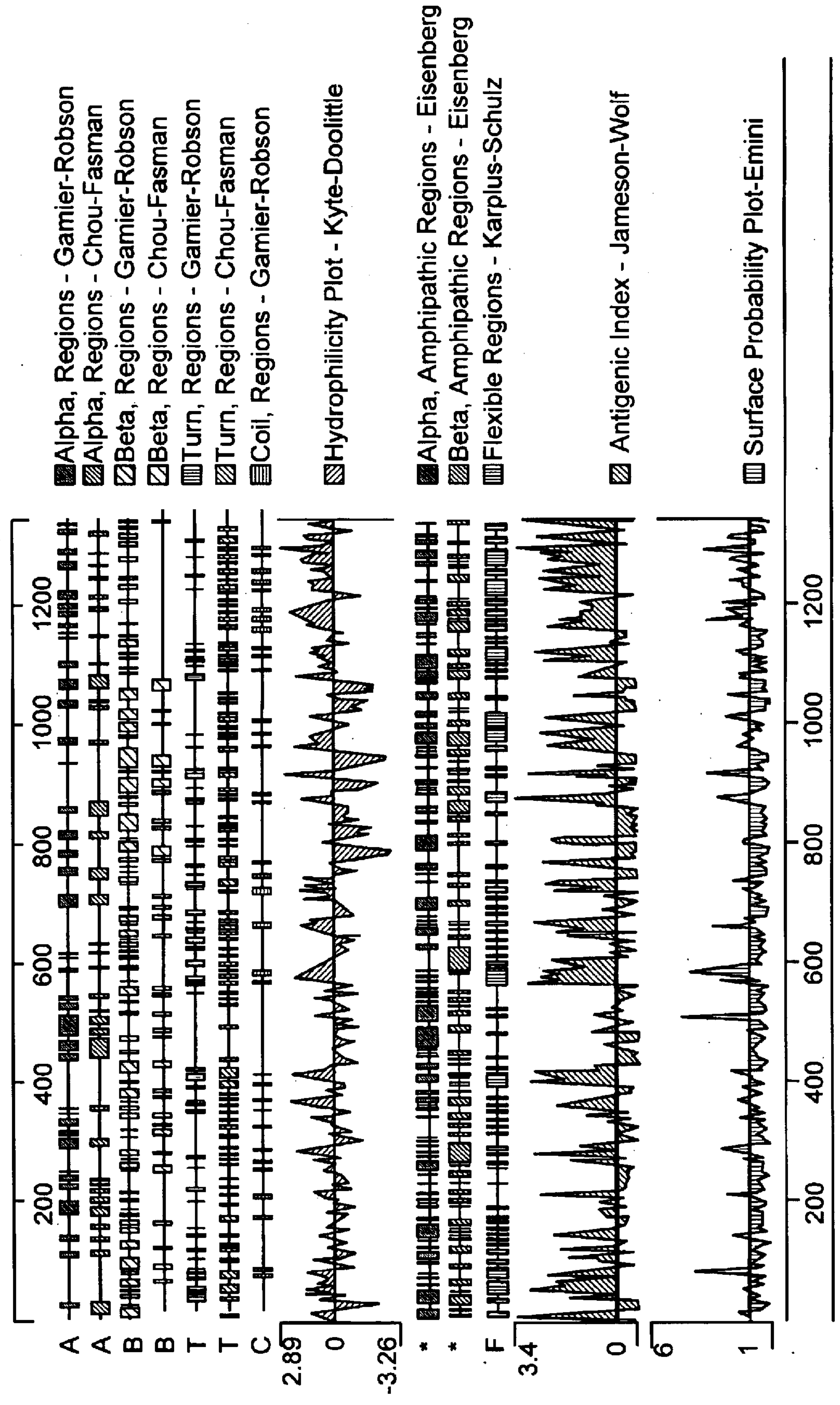
FIG. 3 shows an analysis of the h15571 GPCR-like amino acid sequence: αβ turn and coil regions, hydrophilicity, amphipathic regions, flexible regions, antigenic index, and surface probability plot.

The invention also provides fragments with immunogenic properties. These contain an epitope-bearing portion of the GPCR-like polypeptides of the invention. These epitope-bearing peptides are useful to raise antibodies that bind specifically to a GPCR-like polypeptide or region or fragment. These peptides can contain at least 10, 12, at least 14, or between at least about 15 to about 30 amino acids. Non-limiting examples of antigenic polypeptides that can be used to generate antibodies include but are not limited to peptides derived from an extracellular site. Regions having a high antigenicity index are shown in FIG. 3 for the h15571 polypeptide. However, intracellularly-made antibodies ("intrabodies") are also encompassed, which would recognize intracellular peptide regions. The epitope-bearing GPCR-like polypeptides may be produced by any conventional means (Houghten, R. A. (1985) *Proc. Natl. Acad. Sci. USA* 82:5131–5135). Simultaneous multiple peptide synthesis is described in U.S. Pat. No. 4,631,211.

By "variants" is intended proteins or polypeptides having an amino acid sequence that is at least about 45%, 55%, 60%, 65%, preferably about 70%, 75%, 80%, 85%, 90%, 91%, 92%, 93%, 94%, 95%, 96%, 97%, 98%, or 99% identical to the amino acid sequence of SEQ ID NO:2. Variants also include polypeptides encoded by the cDNA insert of the plasmid deposited with ATCC as Patent Deposit No. PTA-1660, or polypeptides encoded by a nucleic acid molecule that hybridizes to the nucleic acid molecule of SEQ ID NO:1, or a complement thereof, under stringent conditions. Such variants generally retain the functional activity of the GPCR-like proteins of the invention. Variants include polypeptides that differ in amino acid sequence due to natural allelic variation or mutagenesis.

The invention also provides GPCR-like chimeric or fusion proteins. As used herein, a GPCR-like "chimeric protein" or "fusion protein" comprises a GPCR-like polypeptide operably linked to a non-GPCR-like polypeptide. A "GPCR-like polypeptide" refers to a polypeptide having an amino acid sequence corresponding to a GPCR-like protein, whereas a "non- GPCR-like polypeptide" refers to a polypeptide having an amino acid sequence corresponding to a protein that is not substantially identical to the GPCR-like protein, e.g., a protein that is different from the GPCR-like protein and which is derived from the same or a different organism. Within a GPCR-like fusion protein, the GPCR-like polypeptide can correspond to all or a portion of a GPCR-like protein, preferably at least one biologically active portion of a GPCR-like protein. Within the fusion protein, the term "operably linked" is intended to indicate that the GPCR-like polypeptide and the non-GPCR-like polypeptide are fused in-frame to each other. The non-GPCR-like polypeptide can be fused to the N-terminus or C-terminus of the GPCR-like polypeptide.

One useful fusion protein is a GST-GPCR-like fusion protein in which the GPCR-like sequences are fused to the C-terminus of the GST sequences. Such fusion proteins can facilitate the purification of recombinant GPCR-like proteins.

In yet another embodiment, the fusion protein is a GPCR-like-immunoglobulin fusion protein in which all or part of a GPCR-like protein is fused to sequences derived from a member of the immunoglobulin protein family. The GPCR-like-immunoglobulin fusion proteins of the invention can be incorporated into pharmaceutical compositions and administered to a subject to inhibit an interaction between a GPCR-like ligand and a GPCR protein on the surface of a cell, thereby suppressing GPCR-like-mediated signal transduction in vivo. The GPCR-immunoglobulin fusion proteins can be used to affect the bioavailability of a GPCR-like cognate ligand. Inhibition of the GPCR-like ligand/GPCR-like interaction may be useful therapeutically, both for treating proliferative and differentiative disorders and for modulating (e.g., promoting or inhibiting) cell survival. Moreover, the GPCR-like-immunoglobulin fusion proteins of the invention can be used as immunogens to produce anti-GPCR-like antibodies in a subject, to purify GPCR-like ligands, and in screening assays to identify molecules that inhibit the interaction of a GPCR-like protein with a GPCR-like ligand.

Preferably, a GPCR-like chimeric or fusion protein of the invention is produced by standard recombinant DNA techniques. For example, DNA fragments coding for the different polypeptide sequences may be ligated together in-frame, or the fusion gene can be synthesized, such as with automated DNA synthesizers. Alternatively, PCR amplification of gene fragments can be carried out using anchor primers that give rise to complementary overhangs between two consecutive gene fragments, which can subsequently be annealed and reamplified to generate a chimeric gene sequence (see, e.g., Ausubel et al., eds. (1995) *Current Protocols in Molecular Biology*) (Greene Publishing and Wiley-Interscience, NY). Moreover, a GPCR-like-encoding nucleic acid can be cloned into a commercially available expression vector such that it is linked in-frame to an existing fusion moiety.

Variants of the GPCR-like proteins can function as either GPCR-like agonists (mimetics) or as GPCR-like antagonists. Variants of the GPCR-like protein can be generated by mutagenesis, e.g., discrete point mutation or truncation of the GPCR-like protein. An agonist of the GPCR-like protein can retain substantially the same, or a subset, of the biological activities of the naturally occurring form of the GPCR-like protein. An antagonist of the GPCR-like protein can inhibit one or more of the activities of the naturally occurring form of the GPCR-like protein by, for example, competitively binding to a downstream or upstream member of a cellular signaling cascade that includes the GPCR-like protein. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the GPCR-like proteins.

Variants of a GPCR-like protein that function as either GPCR-like agonists or as GPCR-like antagonists can be identified by screening combinatorial libraries of mutants, e.g., truncation mutants, of a GPCR-like protein for GPCR-like protein agonist or antagonist activity. In one embodiment, a variegated library of GPCR-like variants is generated by combinatorial mutagenesis at the nucleic acid level and is encoded by a variegated gene library. A variegated library of GPCR-like variants can be produced by, for example, enzymatically ligating a mixture of synthetic oligonucleotides into gene sequences such that a degenerate set of potential GPCR-like sequences is expressible as individual polypeptides, or alternatively, as a set of larger fusion proteins (e.g., for phage display) containing the set of GPCR-like sequences therein. There are a variety of methods that can be used to produce libraries of potential GPCR-like variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential GPCR-like sequences. Methods for synthesizing degenerate oligonucleotides are known in the art (see, e.g., Narang (1983) Tetrahedron 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of a GPCR-like protein coding sequence can be used to generate a variegated population of GPCR-like fragments for screening and subsequent selection of variants of a GPCR-like protein. In one embodiment, a library of coding sequence fragments can be generated by treating a double-stranded PCR fragment of a GPCR-like coding sequence with a nuclease under conditions wherein nicking occurs only about once per molecule, denaturing the double-stranded DNA, renaturing the DNA to form double-stranded DNA which can include sense/antisense pairs from different nicked products, removing single-stranded portions from reformed duplexes by treatment with S1 nuclease, and ligating the resulting fragment library into an expression vector. By this method, one can derive an expression library that encodes N-terminal and internal fragments of various sizes of the GPCR-like protein.

Several techniques are known in the art for screening gene products of combinatorial libraries made by point mutations or truncation and for screening cDNA libraries for gene products having a selected property. Such techniques are adaptable for rapid screening of the gene libraries generated by the combinatorial mutagenesis of GPCR-like proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique that enhances the frequency of functional mutants in the libraries, can be used in combination with the screening assays to identify GPCR-like variants (Arkin and Yourvan (1992) Proc. Natl. Acad. Sci. USA 89:7811–7815; Delgrave et al. (1993) *Protein Engineering* 6(3):327–331).

An isolated GPCR-like polypeptide or fragments thereof of the invention can be used as an immunogen to generate antibodies that bind GPCR-like proteins using standard techniques for polyclonal and monoclonal antibody preparation. The full-length GPCR-like protein can be used or, alternatively, the invention provides antigenic peptide fragments of GPCR proteins for use as immunogens. The antigenic peptide of a GPCR-like protein comprises at least 8, preferably 10, 15, 20, or 30 amino acid residues of the amino acid sequence shown in SEQ ID NO:2 and encompasses an epitope of a GPCR-like protein such that an antibody raised against the peptide forms a specific immune complex with the GPCR-like protein. Preferred epitopes encompassed by the antigenic peptide are regions of a GPCR-like protein that are located on the surface of the protein, e.g., hydrophilic regions.

Accordingly, another aspect of the invention pertains to anti-GPCR-like polyclonal and monoclonal antibodies that bind a GPCR-like protein. Polyclonal anti-GPCR-like antibodies can be prepared by immunizing a suitable subject (e.g., rabbit, goat, mouse, or other mammal) with a GPCR-like immunogen. The anti-GPCR-like antibody titer in the immunized subject can be monitored over time by standard techniques, such as with an enzyme linked immunosorbent assay (ELISA) using immobilized GPCR-like protein. At an appropriate time after immunization, e.g., when the anti-GPCR-like antibody titers are highest, antibody-producing cells can be obtained from the subject and used to prepare monoclonal antibodies by standard techniques, such as the hybridoma technique originally described by Kohler and Milstein (1975) *Nature* 256:495–497, the human B cell hybridoma technique (Kozbor et al. (1983) *Immunol. Today* 4:72), the EBV-hybridoma technique (Cole et al. (1985) in *Monoclonal Antibodies and Cancer Therapy*, ed. Reisfeld and Sell (Alan R. Liss, Inc., New York, N.Y.), pp. 77–96) or trioma techniques. The technology for producing hybridomas is well known (see generally Coligan et al., eds. (1994) *Current Protocols in Immunology* (John Wiley & Sons, Inc., New York, N.Y.); Galfre et al. (1977) *Nature* 266:55052; Kenneth (1980) in *Monoclonal Antibodies: A New Dimension In Biological Analyses* (Plenum Publishing Corp., NY; and Lemer (1981) *Yale J Biol. Med.*, 54:387–402).

Alternative to preparing monoclonal antibody-secreting hybridomas, a monoclonal anti-GPCR-like antibody can be identified and isolated by screening a recombinant combinatorial immunoglobulin library (e.g., an antibody phage display library) with a GPCR-like protein to thereby isolate immunoglobulin library members that bind the GPCR-like protein. Kits for generating and screening phage display libraries are commercially available (e.g., the Pharmacia *Recombinant Phage Antibody System*, Catalog No. 27-9400–01; and the Stratagene SurjZAP™ phage Display Kit, Catalog No. 240612). Additionally, examples of methods and reagents particularly amenable for use in generating and screening antibody display library can be found in, for example, U.S. Pat. No. 5,223,409; PCT Publication Nos. WO 92/18619; WO 91/17271; WO 92/20791; WO 92/15679; 93/01288; WO 92/01047; 92/09690; and 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J.* 12:725–734.

Additionally, recombinant anti-GPCR-like antibodies, such as chimeric and humanized monoclonal antibodies, comprising both human and nonhuman portions, which can be made using standard recombinant DNA techniques, are within the scope of the invention. Such chimeric and humanized monoclonal antibodies can be produced by recombinant DNA techniques known in the art, for example using methods described in PCT Publication Nos. WO 86/101533 and WO 87/02671; European Patent Application Nos. 184,187, 171,496, 125,023, and 173,494; U.S. Pat. Nos. 4,816,567 and 5,225,539; European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; Shaw et al. (1988) *J. Natl. Cancer Inst.* 80:1553–1559); Morrison (1985) *Science* 229:1202–1207; Oi et al. (1986) *Bio/Techniques* 4:214; Jones et al. (1986) *Nature* 321:552–525; Verhoeyan et al. (1988) *Science* 239:1534; and Beidler et al. (1988) *J. Immunol.* 141:4053–4060.

Completely human antibodies are particularly desirable for therapeutic treatment of human patients. Such antibodies can be produced using transgenic mice that are incapable of expressing endogenous immunoglobulin heavy and light chains genes, but which can express human heavy and light chain genes. See, for example, Lonberg and Huszar (1995) *Int. Rev. Immunol.* 13:65–93); and U.S. Pat. Nos. 5,625,126; 5,633,425; 5,569,825; 5,661,016; and 5,545,806. In addition, companies such as Abgenix, Inc. (Fremont, Calif.), can be engaged to provide human antibodies directed against a selected antigen using technology similar to that described above.

Completely human antibodies that recognize a selected epitope can be generated using a technique referred to as “guided selection.” In this approach a selected non-human monoclonal antibody, e.g., a murine antibody, is used to guide the selection of a completely human antibody recognizing the same epitope. This technology is described by Jespers et al. (1994) *Bio/Technology* 12:899–903).

An anti-GPCR-like antibody (e.g., a monoclonal antibody) can be used to isolate GPCR-like proteins by standard techniques, such as affinity chromatography or immunoprecipitation. An anti-GPCR-like antibody can facilitate the purification of natural GPCR-like protein from cells and of recombinantly produced GPCR-like protein expressed in host cells. Moreover, an anti-GPCR-like antibody can be used to detect GPCR-like protein (e.g., in a cellular lysate or cell supernatant) in order to evaluate the abundance and pattern of expression of the GPCR-like protein. Anti-GPCR-like antibodies can be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidinibiotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{35}S$, or $^{3}H$.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor-alpha, tumor necrosis factor-beta, alpha-interferon, beta-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Armon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies 84: Biological And clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev., 62:119–58 (1982). Alternatively, an antibody can be conjugated to a second antibody to form an antibody heteroconjugate as described by Segal in U.S. Pat. No. 4,676,980.

III. Recombinant Expression Vectors and Host Cells

Another aspect of the invention pertains to vectors, preferably expression vectors, containing a nucleic acid encoding a GPCR-like protein (or a portion thereof). "Vector" refers to a nucleic acid molecule capable of transporting another nucleic acid to which it has been linked, such as a "plasmid", a circular double-stranded DNA loop into which additional DNA segments can be ligated, or a viral vector, where additional DNA segments can be ligated into the viral genome. The vectors are useful for autonomous replication in a host cell or may be integrated into the genome of a host cell upon introduction into the host cell, and thereby are replicated along with the host genome (e.g., nonepisomal mammalian vectors). Expression vectors are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses, and adeno-associated viruses), that serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, operably linked to the nucleic acid sequence to be expressed. "Operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers, and other expression control elements (e.g., polyadenylation signals). See, for example, Goeddel (1990) in *Gene Expression Technology: Methods in Enzymology* 185 (Academic Press, San Diego, Calif.). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., GPCR-like proteins, mutant forms of GPCR-like proteins, fusion proteins, etc.).

The recombinant expression vectors of the invention can be designed for expression of GPCR-like protein in prokaryotic or eukaryotic host cells. Expression of proteins in prokaryotes is most often carried out in *E. coli* with vectors containing constitutive or inducible promoters directing the expression of either fusion or nonfusion proteins. Fusion vectors add a number of amino acids to a protein encoded therein, usually to the amino terminus of the recombinant protein. Typical fusion expression vectors include pGEX (Pharmacia Biotech Inc; Smith and Johnson (1988) *Gene* 67:31–40), pMAL (New England Biolabs, Beverly, Mass.), and pRIT5 (Pharmacia, Piscataway, N.J.) which fuse glutathione S-transferase (GST), maltose E binding protein, or protein A, respectively, to the target recombinant protein. Examples of suitable inducible nonfusion *E. coli* expression vectors include pTrc (Amann et al. (1988) *Gene* 69:301–315) and pET 11d (Studier et al. (1990) in *Gene Expression Technology: Methods in Enzymology* 185 (Academic Press, San Diego, Calif.), pp. 60–89). Strategies to maximize recombinant protein expression in *E. coli* can be found in Gottesman (1990) in *Gene Expression Technology: Methods in Enzymology* 185 (Academic Press, California), pp. 119–128 and Wada et al. (1992) *Nucleic Acids Res.* 20:2111–2118. Target gene expression from the pTrc vector relies on host RNA polymerase transcription from a hybrid trp-lac fusion promoter.

Suitable eukaryotic host cells include insect cells (examples of Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39)); yeast cells (examples of vectors for expression in yeast *S. cereivisiae* include pYepSec1 (Baldari et al. (1987) *EMBO J.* 6:229–234), pMFa (Kudjan and Herskowitz (1982) Cell 30:933–943), pJRY88 (Schultz et al. (1987) *Gene* 54:113–123), pYES2 (Invitrogen Corporation, San Diego, Calif.), and pPicZ (Invitrogen Corporation, San Diego, Calif.)); or mammalian cells (mammalian expression vectors include pCDM8 (Seed (1987) *Nature* 329:840) and pMT2PC (Kaufman et al. (1987) *EMBO J.* 6:187:195)). Suitable mammalian cells include Chinese hamster ovary cells (CHO) or SV40 transformed simian kidney cells (COS). In mammalian cells, the expression vector's control functions are often provided by viral regulatory elements. For example, commonly used promoters are derived from polyoma, Adenovirus 2, cytomegalovirus, and Simian Virus 40. For other suitable expression systems for both prokaryotic and eukaryotic cells, see chapters 16 and 17 of Sambrook et al. (1989) *Molecular cloning: A Laboratory Manual* (2d ed., Cold Spring Harbor Laboratory Press, Plainview, N.Y.). See, Goeddel (1990) in *Gene Expression Technology: Methods in Enzymology* 185 (Academic Press, San Diego, Calif.). Alternatively, the recombinant expression vector can be transcribed and translated in vitro, for example using T7 promoter regulatory sequences and T7 polymerase.

The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell but are still included within the scope of the term as used herein.

In one embodiment, the expression vector is a recombinant mammalian expression vector that comprises tissue-specific regulatory elements that direct expression of the nucleic acid preferentially in a particular cell type. Suitable tissue-specific promoters include the albumin promoter (e.g., liver-specific promoter; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Baneiji et al. (1983) *Cell* 33:729–740; Queen and Baltimore (1983) Cell 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Patent Publication No. 264,166). Developmentally-regulated promoters are also encompassed, for example the murine homeobox (Hox) promoter (Kessel and Gruss (1990) *Science* 249:374–379), the α-fetoprotein promoter (Campes and Tilghman (1989) Genes Dev. 3:537–546), and the like.

The invention further provides a recombinant expression vector comprising a DNA molecule of the invention cloned into the expression vector in an antisense orientation. That is, the DNA molecule is operably linked to a regulatory sequence in a manner that allows for expression (by transcription of the DNA molecule) of an RNA molecule that is antisense to GPCR-like mRNA. Regulatory sequences operably linked to a nucleic acid cloned in the antisense orientation can be chosen to direct the continuous expression of the antisense RNA molecule in a variety of cell types, for instance viral promoters and/or enhancers, or regulatory sequences can be chosen to direct constitutive, tissue-specific, or cell-type-specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes, see Weintraub et al. (1986) *Reviews—Trends in Genetics*, Vol. 1(1).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (1989) *Molecular Cloning: A Laboraty Manual* (2d ed., Cold Spring Harbor Laboratory Press, Plainview, N.Y.) and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin, and methotrexate. Nucleic acid encoding a selectable marker can be introduced into a host cell on the same vector as that encoding a GPCR-like protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) GPCR-like protein. Accordingly, the invention further provides methods for producing GPCR-like protein using the host cells of the invention. In one embodiment, the method comprises culturing the host cell of the invention, into which a recombinant expression vector encoding a GPCR-like protein has been introduced, in a suitable medium such that GPCR-like protein is produced. In another embodiment, the method further comprises isolating GPCR-like protein from the medium or the host cell.

The host cells of the invention can also be used to produce nonhuman transgenic animals. For example, in one embodiment, a host cell of the invention is a fertilized oocyte or an embryonic stem cell into which GPCR-like-coding sequences have been introduced. Such host cells can then be used to create nonhuman transgenic animals in which exogenous GPCR-like sequences have been introduced into their genome or homologous recombinant animals in which endogenous GPCR-like sequences have been altered. Such animals are useful for studying the function and/or activity of GPCR-like genes and proteins and for identifying and/or evaluating modulators of GPCR-like activity. As used herein, a "transgenic animal" is a nonhuman animal, preferably a mammal, more preferably a rodent such as a rat or mouse, in which one or more of the cells of the animal includes a transgene. Other examples of transgenic animals include nonhuman primates, sheep, dogs, cows, goats, chickens, amphibians, etc. A transgene is exogenous DNA that is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a nonhuman animal, preferably a mammal, more preferably a mouse, in which an endogenous GPCR-like gene has been altered by homologous recombination between the endogenous gene and an exogenous DNA molecule introduced into a cell of the animal, e.g., an embryonic cell of the animal, prior to development of the animal.

A transgenic animal of the invention can be created by introducing GPCR-like-encoding nucleic acid into the male pronuclei of a fertilized oocyte, e.g., by microinjection, retroviral infection, and allowing the oocyte to develop in a pseudopregnant female foster animal. The GPCR-like cDNA sequence can be introduced as a transgene into the genome of a nonhuman animal. Alternatively, a homologue of the mouse GPCR-like gene can be isolated based on hybridization and used as a transgene. Intronic sequences and polyadenylation signals can also be included in the transgene to increase the efficiency of expression of the transgene. A tissue-specific regulatory sequence(s) can be operably linked to the GPCR-like transgene to direct expression of GPCR-like protein to particular cells. Methods for generating transgenic animals via embryo manipulation and microinjection, particularly animals such as mice, have become conventional in the art and are described, for example, in U.S. Pat. Nos. 4,736,866, 4,870,009, and 4,873,191 and in Hogan (1986) *Manipulating the Mouse Embryo* (Cold Spring Harbor Laboratory Press, Cold Spring Harbor, N.Y., 1986). Similar methods are used for production of other transgenic animals. A transgenic founder animal can be identified based upon the presence of the GPCR-like transgene in its genome and/or expression of GPCR-like mRNA in tissues or cells of the animals. A transgenic founder animal can then be used to breed additional animals carrying the transgene. Moreover, transgenic animals carrying a transgene encoding GPCR-like gene can further be bred to other transgenic animals carrying other transgenes.

To create a homologous recombinant animal, one prepares a vector containing at least a portion of a GPCR-like gene or a homolog of the gene into which a deletion, addition, or substitution has been introduced to thereby alter, e.g., functionally disrupt, the GPCR-like gene. In a preferred embodiment, the vector is designed such that, upon homologous recombination, the endogenous GPCR-like gene is functionally disrupted (i.e., no longer encodes a functional protein; also referred to as a "knock out" vector). Alternatively, the vector can be designed such that, upon homologous recombination, the endogenous GPCR-like gene is mutated or otherwise altered but still encodes functional protein (e.g., the upstream regulatory region can be altered to thereby alter the expression of the endogenous GPCR-like protein). In the homologous recombination vector, the altered portion of the GPCR-like gene is flanked at its 5' and 3' ends by additional nucleic acid of the GPCR-like gene to allow for homologous recombination to occur between the exogenous GPCR-like gene carried by the vector and an endogenous GPCR-like gene in an embryonic stem cell. The additional flanking GPCR-like nucleic acid is of sufficient length for successful homologous recombination with the endogenous gene. Typically, several kilobases of flanking DNA (at both the 5' and 3' ends) are included in the vector (see, e.g., Thomas and Capecchi (1987) *Cell* 51:503 for a description of homologous recombination vectors). The vector is introduced into an embryonic stem cell line (e.g., by electroporation), and cells in which the introduced GPCR-like gene has homologously recombined with the endogenous GPCR-like gene are selected (see, e.g., Li et al. (1992) *Cell* 69:915). The selected cells are then injected into a blastocyst of an animal (e.g., a mouse) to form aggregation chimeras (see, e.g., Bradley (1987) in *Teratocarcinomas and Embryonic Stem Cells: A Practical Approach*, ed. Robertson (IRL, Oxford pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823–829 and in PCT Publication Nos. WO 90/11354, WO 91/01140, WO 92/0968, and WO 93/04169.

In another embodiment, transgenic nonhuman animals containing selected systems that allow for regulated expression of the transgene can be produced. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of Saccharomyces cerevisiae (O'Gorman et al. (1991) *Science* 251:1351–1355). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the nonhuman transgenic animals described herein can also be produced according to the methods described in Wilmut et al. (1997) *Nature* 385:810–813 and PCT Publication Nos. WO 97/07668 and WO 97/07669.

IV. Pharmaceutical Compositions

The GPCR-like nucleic acid molecules, GPCR-like proteins, and modulators thereof (e.g., anti-GPCR-like antibodies) (also referred to herein as "active compounds") of the invention can be incorporated into pharmaceutical compositions suitable for administration. Such compositions typically comprise the nucleic acid molecule, protein, or modulators thereof (e.g., antibody or small molecule) and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The compositions of the invention are useful to treat any of the disorders discussed herein. The compositions are provided in therapeutically effective amounts. By "therapeutically effective amounts" is intended an amount sufficient to modulate the desired response. As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e, including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, N.J.), or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride, in the composition. Prolonged absorption of the injectable compositions can be brought about by including in the composition an agent that delays absorption, for example, aluminum monostearate and gelatin.

Sterile injectable solutions can be prepared by incorporating the active compound (e.g., a GPCR-like protein or anti-GPCR-like antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions the preferred methods of preparation are vacuum drying and freeze-drying, which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth, or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from a pressurized container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermnal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated with each unit containing a predetermined quantity of active compound calculated to produce the desired therapeutic effect in association with the required pharmaceutical carrier. Depending on the type and severity of the disease, about 1 μg/kg to about 15 mg/kg (e.g., 0.1 to 20 mg/kg) of antibody is an initial candidate dosage for administration to the patient, whether, for example, by one or more separate administrations, or by continuous infusion. A typical daily dosage might range from about 1 μg/kg to about 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is disclosed in WO 94/04188. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: (a) screening assays; (b) detection assays (e.g., chromosomal mapping, tissue typing, forensic biology); (c) predictive medicine (e.g., diagnostic assays, prognostic assays, monitoring clinical trials, and pharmacogenomics); and (d) methods of treatment (e.g., therapeutic and prophylactic). The isolated nucleic acid molecules of the invention can be used to express GPCR-like protein (e.g., via a recombinant expression vector in a host cell in gene therapy applications), to detect GPCR-like mRNA (e.g., in a biological sample) or a genetic lesion in a GPCR-like gene, and to modulate GPCR-like activity. In addition, the GPCR-like proteins can be used to screen drugs or compounds that modulate the immune response as well as to treat disorders characterized by insufficient or excessive production of GPCR-like protein or production of GPCR-like protein forms that have decreased or aberrant activity compared to GPCR-like wild type protein. In addition, the anti-GPCR-like antibodies of the invention can be used to detect and isolate GPCR-like proteins and modulate GPCR-like activity.

A. Screening Assays

The invention provides a method (also referred to herein as a "screening assay") for identifying modulators, i.e., candidate or test compounds or agents (e.g., peptides, peptidomimetics, small molecules, or other drugs) that bind to GPCR-like proteins or have a stimulatory or inhibitory effect on, for example, GPCR-like expression or GPCR-like activity.

The test compounds of the present invention can be obtained using any of the numerous approaches in combinatorial library methods known in the art, including biological libraries, spatially addressable parallel-solid phase or solution phase libraries, synthetic library methods requiring deconvolution, the "one-bead one-compound" library method, and synthetic library methods using affinity chromatography selection. The biological library approach is limited to peptide libraries, while the other four approaches are applicable to peptide, nonpeptide oligomer, or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Bio/Techniques* 13:412–421), or on beads (Lam (1991) *Nature* 354:82–84), chips (Fodor (1993) *Nature* 364:555–556), bacteria (U.S. Pat. No. 5,223,409), spores (U.S. Pat. Nos. 5,571,698; 5,403,484; and 5,223,409), plasmids (Cull et al. (1992) *Proc. Natl. Acad. Sci. USA* 89:1865–1869), or phage (Scott and Smith (1990) *Science* 249:386–390; Devlin (1990) *Science* 249:404–406; Cwirla et al. (1990) *Proc. Natl. Acad. Sci. USA* 87:6378–6382; and Felici (1991) *J. Mol. Biol.* 222:301–310).

Determining the ability of the test compound to bind to the GPCR-like protein can be accomplished, for example, by coupling the test compound with a radioisotope or enzymatic label such that binding of the test compound to the GPCR-like protein or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product.

In a similar manner, one may determine the ability of the GPCR-like protein to bind to or interact with a GPCR-like target molecule. By "target molecule" is intended a molecule with which a GPCR-like protein binds or interacts in nature. In a preferred embodiment, the ability of the GPCR-like protein to bind to or interact with a GPCR-like target molecule can be determined by monitoring the activity of the target molecule. For example, the activity of the target molecule can be monitored by detecting induction of a cellular second messenger of the target (e.g., intracellular $Ca^{2+}$, diacylglycerol, IP3, etc.), detecting catalytic/enzymatic activity of the target on an appropriate substrate, detecting the induction of a reporter gene (e.g., a GPCR-like-responsive regulatory element operably linked to a nucleic acid encoding a detectable marker, e.g. luciferase), or detecting a cellular response, for example, cellular differentiation or cell proliferation.

In yet another embodiment, an assay of the present invention is a cell-free assay comprising contacting a GPCR-like protein or biologically active portion thereof with a test compound and determining the ability of the test compound to bind to the GPCR-like protein or biologically active portion thereof. Binding of the test compound to the GPCR-like protein can be determined either directly or indirectly as described above. In a preferred embodiment, the assay includes contacting the GPCR-like protein or biologically active portion thereof with a known compound that binds GPCR-like protein to form an assay mixture, contacting the assay mixture with a test compound, and determining the ability of the test compound to preferentially bind to GPCR-like protein or biologically active portion thereof as compared to the known compound.

In another embodiment, an assay is a cell-free assay comprising contacting GPCR-like protein or biologically active portion thereof with a test compound and determining the ability of the test compound to modulate (e.g., stimulate or inhibit) the activity of the GPCR-like protein or biologically active portion thereof. Determining the ability of the test compound to modulate the activity of a GPCR-like protein can be accomplished, for example, by determining the ability of the GPCR-like protein to bind to a GPCR-like target molecule as described above for determining direct binding. In an alternative embodiment, determining the ability of the test compound to modulate the activity of a GPCR-like protein can be accomplished by determining the ability of the GPCR-like protein to further modulate a GPCR-like target molecule. For example, the catalytic/enzymatic activity of the target molecule on an appropriate substrate can be determined as previously described.

In yet another embodiment, the cell-free assay comprises contacting the GPCR-like protein or biologically active portion thereof with a known compound that binds a GPCR-like protein to form an assay mixture, contacting the assay mixture with a test compound, and determining the ability of the test compound to preferentially bind to or modulate the activity of a GPCR-like target molecule.

In the above-mentioned assays, it may be desirable to immobilize either a GPCR-like protein or its target molecule to facilitate separation of complexed from uncomplexed forms of one or both of the proteins, as well as to accommodate automation of the assay. In one embodiment, a fusion protein can be provided that adds a domain that allows one or both of the proteins to be bound to a matrix. For example, glutathione-S-transferase/GPCR-like fusion proteins or glutathione-S-transferase/target fusion proteins can be adsorbed onto glutathione sepharose beads (Sigma Chemical, St. Louis, Mo.) or glutathione-derivatized microtitre plates, which are then combined with the test compound or the test compound and either the nonadsorbed target protein or GPCR-like protein, and the mixture incubated under conditions conducive to complex formation (e.g., at physiological conditions for salt and pH). Following incubation, the beads or microtitre plate wells are washed to remove any unbound components and complex formation is measured either directly or indirectly, for example, as described above. Alternatively, the complexes can be dissociated from the matrix, and the level of GPCR-like binding or activity determined using standard techniques.

Other techniques for immobilizing proteins on matrices can also be used in the screening assays of the invention. For example, either GPCR-like protein or its target molecule can be immobilized utilizing conjugation of biotin and streptavidin. Biotinylated GPCR-like molecules or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96-well plates (Pierce Chemicals). Alternatively, antibodies reactive with a GPCR-like protein or target molecules but which do not interfere with binding of the GPCR-like protein to its target molecule can be derivatized to the wells of the plate, and unbound target or GPCR-like protein trapped in the wells by antibody conjugation. Methods for detecting such complexes, in addition to those described above for the GST-immobilized complexes, include immunodetection of complexes using antibodies reactive with the GPCR-like protein or target molecule, as well as enzyme-linked assays that rely on detecting an enzymatic activity associated with the GPCR-like protein or target molecule.

In another embodiment, modulators of GPCR-like expression are identified in a method in which a cell is contacted with a candidate compound and the expression of GPCR-like mRNA or protein in the cell is determined relative to expression of GPCR-like mRNA or protein in a cell in the absence of the candidate compound. When expression is greater (statistically significantly greater) in the presence of the candidate compound than in its absence, the candidate compound is identified as a stimulator of GPCR-like mRNA or protein expression. Alternatively, when expression is less (statistically significantly less) in the presence of the candidate compound than in its absence, the candidate compound is identified as an inhibitor of GPCR-like mRNA or protein expression. The level of GPCR-like mRNA or protein expression in the cells can be determined by methods described herein for detecting GPCR-like mRNA or protein.

In yet another aspect of the invention, the GPCR-like proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Bio/Techniques* 14:920–924; Iwabuchi et al. (1993) *Oncogene* 8:1693–1696; and PCT Publication No. WO 94/10300), to identify other proteins, which bind to or interact with GPCR-like protein ("GPCR-like-binding proteins" or "GPCR-like -bp") and modulate GPCR-like activity. Such GPCR-like-binding proteins are also likely to be involved in the propagation of signals by the GPCR-like proteins as, for example, upstream or downstream elements of the GPCR-like pathway.

This invention further pertains to novel agents identified by the above-described screening assays and uses thereof for treatments as described herein.

B. Detection Assays

Portions or fragments of the cDNA sequences identified herein (and the corresponding complete gene sequences) can be used in numerous ways as polynucleotide reagents. For example, these sequences can be used to: (1) map their respective genes on a chromosome; (2) identify an individual from a minute biological sample (tissue typing); and (3) aid in forensic identification of a biological sample. These applications are described in the subsections below.

I. Chromosome Mapping

The isolated complete or partial GPCR-like gene sequences of the invention can be used to map their respective GPCR-like genes on a chromosome, thereby facilitating the location of gene regions associated with genetic disease. Computer analysis of GPCR-like sequences can be used to rapidly select PCR primers (preferably 15–25 bp in length) that do not span more than one exon in the genomic DNA, thereby simplifying the amplification process. These primers can then be used for PCR screening of somatic cell hybrids containing individual human chromosomes. Only those hybrids containing the human gene corresponding to the GPCR-like sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow (because they lack a particular enzyme), but in which human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes (D'Eustachio et al. (1983) *Science* 220:919–924). Somatic cell hybrids containing only fragments of human chromosomes can also be produced by using human chromosomes with translocations and deletions.

Other mapping strategies that can similarly be used to map a GPCR-like sequence 10 to its chromosome include in situ hybridization (described in Fan et al. (1990) *Proc. Natl. Acad. Sci. USA* 87:6223–27), pre-screening with labeled flow-sorted chromosomes, and pre-selection by hybridization to chromosome specific cDNA libraries. Furthermore, fluorescence in situ hybridization (FISH) of a DNA sequence to a metaphase chromosomal spread can be used to provide a precise chromosomal location in one step. For a review of this technique, see Verma et al. (1988) *Human Chromosomes: A Manual of Basic Techniques* (Pergamon Press, NY). The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results in a reasonable amount of time.

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Another strategy to map the chromosomal location of GPCR-like genes uses GPCR-like polypeptides and fragments and sequences of the present invention and antibodies specific thereto. This mapping can be carried out by specifically detecting the presence of a GPCR-like polypeptide in members of a panel of somatic cell hybrids between cells of a first species of animal from which the protein originates and cells from a second species of animal and then determining which somatic cell hybrid(s) expresses the polypeptide and noting the chromosome(s) from the first species of animal that it contains. For examples of this technique, see Pajunen et al. (1988) *Cytogenet. Cell Genet.* 47:37–41 and Van Keuren et al. (1986) *Hum. Genet.* 74:34–40. Alternatively, the presence of a GPCR-like polypeptide in the somatic cell hybrids can be determined by assaying an activity or property of the polypeptide, for example, enzymatic activity, as described in Bordelon-Riser et al. (1979) *Somatic Cell Genetics* 5:597–613 and Owerbach et al. (1978) *Proc. Natl. Acad. Sci. USA* 75:5640–5644.

Once a sequence has been mapped to a precise chromosomal location, the physical position of the sequence on the chromosome can be correlated with genetic map data. (Such data are found, for example, in V. McKusick, *Mendelian Inheritance in Man*, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al. (1987) *Nature* 325:783–787.

Moreover, differences in the DNA sequences between individuals affected and unaffected with a disease associated with the GPCR-like gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The GPCR-like sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes and probed on a Southern blot to yield unique bands for identification. The sequences of the present invention are useful as additional DNA markers for RFLP (described, e.g., in U.S. Pat. No. 5,272,057).

Furthermore, the sequences of the present invention can be used to provide an alternative technique for determining the actual base-by-base DNA sequence of selected portions of an individual's genome. Thus, the GPCR-like sequences of the invention can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The GPCR-like sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. The noncoding sequences of a nucleotide sequence comprising the sequence shown SEQ ID NO:1 can comfortably provide positive individual identification with a panel of perhaps 10 to 1,000 primers that each yield a noncoding amplified sequence of 100 bases. If a predicted coding sequence, such as that in SEQ ID NO:1, is used, a more appropriate number of primers for positive individual identification would be 500 to 2,000.

3. Use of Partial GPCR-like Sequences in Forensic Biology

DNA-based identification techniques can also be used in forensic biology. In this manner, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" that is unique to a particular individual. As mentioned above, actual base sequence information can be used for identification as an accurate alternative to patterns formed by restriction enzyme generated fragments. Sequences targeted to noncoding regions of a sequence comprising the sequence shown in SEQ ID NO:1 are particularly appropriate for this use as greater numbers of polymorphisms occur in the noncoding regions, making it easier to differentiate individuals using this technique. Examples of polynucleotide reagents include the GPCR-like sequences or portions thereof, e.g., fragments derived from the noncoding regions of sequences comprising the sequence shown in SEQ ID NO:I having a length of at least 20 or 30 bases.

The GPCR-like sequences described herein can further be used to provide polynucleotide reagents, e.g., labeled or labelable probes that can be used in, for example, an in situ hybridization technique, to identify a specific tissue. This can be very useful in cases where a forensic pathologist is presented with a tissue of unknown origin. Panels of such GPCR-like probes, can be used to identify tissue by species and/or by organ type.

In a similar fashion, these reagents, e.g., GPCR-like primers or probes can be used to screen tissue culture for contamination (i.e., screen for the presence of a mixture of different types of cells in a culture).

C. Predictive Medicine

The present invention also pertains to the field of predictive medicine in which diagnostic assays, prognostic assays, pharmacogenomics, and monitoring clinical trails are used for prognostic (predictive) purposes to thereby treat an individual prophylactically. These applications are described in the subsections below.

1. Diagnostic Assays

One aspect of the present invention relates to diagnostic assays for detecting GPCR-like protein and/or nucleic acid expression as well as GPCR-like activity, in the context of a biological sample. An exemplary method for detecting the presence or absence of GPCR-like proteins in a biological sample involves obtaining a biological sample from a test subject and contacting the biological sample with a compound or an agent capable of detecting GPCR-like protein or nucleic acid (e.g., mRNA, genomic DNA) that encodes GPCR-like protein such that the presence of GPCR-like protein is detected in the biological sample. Results obtained with a biological sample from the test subject may be compared to results obtained with a biological sample from a control subject.

A preferred agent for detecting GPCR-like mRNA or genomic DNA is a labeled nucleic acid probe capable of hybridizing to GPCR-like mRNA or genomic DNA. The nucleic acid probe can be, for example, a full-length GPCR-like nucleic acid, such as the full-length sequence shown in SEQ ID NO: 1, or a portion thereof, such as a nucleic acid molecule of at least 15, 30, 50, 100, 250, or 500 nucleotides in length and sufficient to specifically hybridize under stringent conditions to GPCR-like mRNA or genomic DNA. Other suitable probes for use in the diagnostic assays of the invention are described herein.

A preferred agent for detecting GPCR-like protein is an antibody capable of binding to GPCR-like protein, preferably an antibody with a detectable label. Antibodies can be polyclonal, or more preferably, monoclonal. An intact antibody, or a fragment thereof (e.g., Fab or $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

The term "biological sample" is intended to include tissues, cells, and biological fluids isolated from a subject, as well as tissues, cells, and fluids present within a subject. That is, the detection method of the invention can be used to detect GPCR-like mRNA, protein, or genomic DNA in a biological sample in vitro as well as in vivo. For example, in vitro techniques for detection of GPCR-like mRNA include Northern hybridizations and in situ hybridizations. In vitro techniques for detection of GPCR-like protein include enzyme linked immunosorbent assays (ELISAs), Western blots, immunoprecipitations, and immunofluorescence. In vitro techniques for detection of GPCR-like genomic DNA include Southern hybridizations. Furthermore, in vivo techniques for detection of GPCR-like protein include introducing into a subject a labeled anti-GPCR-like antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. Preferred biological samples are fibroblast samples, particularly dermal and lung fibroblasts, fibrotic samples, particularly liver fibrotic samples, and hepatic stellate cells isolated by conventional means from a subject.

The invention also encompasses kits for detecting the presence of GPCR-like proteins in a biological sample (a test sample). Such kits can be used to determine if a subject is suffering from or is at increased risk of developing a disorder associated with aberrant expression of GPCR-like protein (e.g., an immunological disorder). For example, the kit can comprise a labeled compound or agent capable of detecting GPCR-like protein or mRNA in a biological sample and means for determining the amount of a GPCR-like protein in the sample (e.g., an anti-GPCR-like antibody or an oligonucleotide probe that binds to DNA encoding a GPCR-like protein, e.g., SEQ ID NO:1). Kits can also include instructions for observing that the tested subject is suffering from or is at risk of developing a disorder associated with aberrant expression of GPCR-like sequences if the amount of GPCR-like protein or mRNA is above or below a normal level.

For antibody-based kits, the kit can comprise, for example: (1) a first antibody (e.g., attached to a solid support) that binds to GPCR-like protein; and, optionally, (2) a second, different antibody that binds to GPCR-like protein or the first antibody and is conjugated to a detectable agent. For oligonucleotide-based kits, the kit can comprise, for example: (1) an oligonucleotide, e.g., a detectably labeled oligonucleotide, that hybridizes to a GPCR-like nucleic acid sequence or (2) a pair of primers useful for amplifying a GPCR-like nucleic acid molecule.

The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples that can be assayed and compared to the test sample contained. Each component of the kit is usually enclosed within an individual container, and all of the various containers are within a single package along with instructions for observing whether the tested subject is suffering from or is at risk of developing a disorder associated with aberrant expression of GPCR-like proteins.

2. Other Diagnostic Assays

In another aspect, the invention features a method of analyzing a plurality of capture probes. The method can be used, e.g., to analyze gene expression. The method includes: providing a two dimensional array having a plurality of addresses, each address of the plurality being positionally distinguishable from each other address of the plurality, and each address of the plurality having a unique capture probe, e.g., a nucleic acid or peptide sequence; contacting the array with a GPCR-like nucleic acid, preferably purified, polypeptide, preferably purified, or antibody, and thereby evaluating the plurality of capture probes. Binding (e.g., in the case of a nucleic acid, hybridization) with a capture probe at an address of the plurality, is detected, e.g., by a signal generated from a label attached to the GPCR-like nucleic acid, polypeptide, or antibody. The capture probes can be a set of nucleic acids from a selected sample, e.g., a sample of nucleic acids derived from a control or non-stimulated tissue or cell.

The method can include contacting the GPCR-like nucleic acid, polypeptide, or antibody with a first array having a plurality of capture probes and a second array having a different plurality of capture probes. The results of each hybridization can be compared, e.g., to analyze differences in expression between a first and second sample. The first plurality of capture probes can be from a control sample, e.g., a wild type, normal, or non-diseased, non-stimulated, sample, e.g., a biological fluid, tissue, or cell sample. The second plurality of capture probes can be from an experimental sample, e.g., a mutant type, at risk, disease-state or disorder-state, or stimulated, sample, e.g., a biological fluid, tissue, or cell sample.

The plurality of capture probes can be a plurality of nucleic acid probes each of which specifically hybridizes, with an allele of a GPCR-like sequence of the invention. Such methods can be used to diagnose a subject, e.g., to evaluate risk for a disease or disorder, to evaluate suitability of a selected treatment for a subject, to evaluate whether a subject has a disease or disorder. Thus, for example, the h15571 sequence set forth in SEQ ID NO:1 encodes a GPCR-like polypeptide that is associated with liver function, thus it is useful for evaluating liver disorders.

The method can be used to detect single nucleotide polymorphisms (SNPs), as described below.

In another aspect, the invention features a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express a GPCR-like polypeptide of the invention or from a cell or subject in which a GPCR-like-mediated response has been elicited, e.g., by contact of the cell with a GPCR-like nucleic acid or protein of the invention, or administration to the cell or subject a GPCR-like nucleic acid or protein of the invention; contacting the array with one or more inquiry probes, wherein an inquiry probe can be a nucleic acid, polypeptide, or antibody (which is preferably other than a GPCR-like nucleic acid, polypeptide, or antibody of the invention); providing a two dimensional array having a plurality of addresses, each address of the plurality being positionally distinguishable from each other address of the plurality, and each address of the plurality having a unique capture probe, e.g., wherein the capture probes are from a cell or subject which does not express a GPCR-like sequence of the invention (or does not express as highly as in the case of the GPCR-like positive plurality of capture probes) or from a cell or subject in which a GPCR-like-mediated response has not been elicited (or has been elicited to a lesser extent than in the first sample); contacting the array with one or more inquiry probes (which is preferably other than a GPCR-like nucleic acid, polypeptide, or antibody of the invention), and thereby evaluating the plurality of capture probes. Binding, e.g., in the case of a nucleic acid, hybridization, with a capture probe at an address of the plurality, is detected, e.g., by signal generated from a label attached to the nucleic acid, polypeptide, or antibody.

In another aspect, the invention features a method of analyzing a GPCR-like sequence of the invention, e.g., analyzing structure, function, or relatedness to other nucleic acid or amino acid sequences. The method includes: providing a GPCR-like nucleic acid or amino acid sequence, e.g., the h15571 sequence set forth in SEQ ID NO:1 or SEQ ID NO:2 or a portion thereof, comparing the GPCR-like sequence with one or more preferably a plurality of sequences from a collection of sequences, e.g., a nucleic acid or protein sequence database; to thereby analyze the GPCR-like sequence of the invention.

The method can include evaluating the sequence identity between a GPCR-like sequence of the invention, e.g., the h15571 sequence, and a database sequence. The method can be performed by accessing the database at a second site, e.g., over the internet.

In another aspect, the invention features, a set of oligonucleotides, useful, e.g., for identifying SNP's, or identifying specific alleles of a GPCR-like sequence of the invention, e.g., the h15571 sequence. The set includes a plurality of oligonucleotides, each of which has a different nucleotide at an interrogation position, e.g., an SNP or the site of a mutation. In a preferred embodiment, the oligonucleotides of the plurality identical in sequence with one another (except for differences in length). The oligonucleotides can be provided with differential labels, such that an oligonucleotides which hybridizes to one allele provides a signal that is distinguishable from an oligonucleotides which hybridizes to a second allele.

3. Prognostic Assays

The methods described herein can furthermore be utilized as diagnostic or prognostic assays to identify subjects having or at risk of developing a disease or disorder associated with GPCR-like protein, GPCR-like nucleic acid expression, or GPCR-like activity. Prognostic assays can be used for prognostic or predictive purposes to thereby prophylactically treat an individual prior to the onset of a disorder characterized by or associated with GPCR-like protein, GPCR-like nucleic acid expression, or GPCR-like activity.

Thus, the present invention provides a method in which a test sample is obtained from a subject, and GPCR-like protein or nucleic acid (e.g., mRNA, genomic DNA) is detected, wherein the presence of GPCR-like protein or nucleic acid is diagnostic for a subject having or at risk of developing a disease or disorder associated with aberrant GPCR-like expression or activity. As used herein, a "test sample" refers to a biological sample obtained from a subject of interest. For example, a test sample can be a biological fluid (e.g., serum), cell sample, or tissue.

Furthermore, using the prognostic assays described herein, the present invention provides methods for determining whether a subject can be administered a specific agent (e.g., an agonist, antagonist, peptidomimetic, protein, peptide, nucleic acid, small molecule, or other drug candidate) or class of agents (e.g., agents of a type that decrease GPCR-like activity) to effectively treat a disease or disorder associated with aberrant GPCR-like expression or activity. In this manner, a test sample is obtained and GPCR-like protein or nucleic acid is detected. The presence of GPCR-like protein or nucleic acid is diagnostic for a subject that can be administered the agent to treat a disorder associated with aberrant GPCR-like expression or activity.

The methods of the invention can also be used to detect genetic lesions or mutations in a GPCR-like gene, thereby determining if a subject with the lesioned gene is at risk for a disorder characterized by aberrant cell proliferation and/or differentiation. In preferred embodiments, the methods include detecting, in a sample of cells from the subject, the presence or absence of a genetic lesion or mutation characterized by at least one of an alteration affecting the integrity of a gene encoding a GPCR-like protein, or the misexpression of the GPCR-like gene. For example, such genetic lesions or mutations can be detected by ascertaining the existence of at least one of: (1) a deletion of one or more nucleotides from a GPCR-like gene; (2) an addition of one or more nucleotides to a GPCR-like gene; (3) a substitution of one or more nucleotides of a GPCR-like gene; (4) a chromosomal rearrangement of a GPCR-like gene; (5) an alteration in the level of a messenger RNA transcript of a GPCR-like gene; (6) an aberrant modification of a GPCR-like gene, such as of the methylation pattern of the genomic DNA; (7) the presence of a non-wild-type splicing pattern of a messenger RNA transcript of a GPCR-like gene; (8) a non-wild-type level of a GPCR-like protein; (9) an allelic loss of a GPCR-like gene; and (10) an inappropriate post-translational modification of a GPCR-like protein. As described herein, there are a large number of assay techniques known in the art that can be used for detecting lesions in a GPCR-like gene. Any cell type or tissue, for example, hepatic stellate cells, derrnal and lung fibroblasts, fibrotic tissues, particularly fibrotic liver tissues, in which the GPCR-like proteins are expressed may be utilized in the prognostic assays described herein.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the GPCR-like gene (see, e.g., Abravaya et al. (1995) *Nucleic Acids Res.* 23:675–682). It is anticipated that PCR and/or LCR may be desirable to use as a preliminary amplification step in conjunction with any of the techniques used for detecting mutations described herein.

Alternative amplification methods include self sustained sequence replication (Guatelli et al. (1990) *Proc. Natl. Acad. Sci. USA* 87:1874–1878), transcriptional amplification system (Kwoh et al. (1989) *Proc. Natl. Acad. Sci. USA* 86:1173–1177), Q-Beta Replicase (Lizardi et al. (1988) *Bio/Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a GPCR-like gene from a sample cell can be identified by alterations in restriction enzyme cleavage patterns of isolated test sample and control DNA digested with one or more restriction endonucleases. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations in a GPCR-like molecule can be identified by hybridizing a sample and control nucleic acids, e.g., DNA or RNA, to high density arrays containing hundreds or thousands of oligonucleotides probes (Cronin et al. (1996) *Human Mutation* 7:244–255; Kozal et al. (1996) *Nature Medicine* 2:753–759). In yet another embodiment, any of a variety of sequencing reactions known in the art can be used to directly sequence the GPCR-like gene and detect mutations by comparing the sequence of the sample GPCR-like gene with the corresponding wild-type (control) sequence. Examples of sequencing reactions include those based on techniques developed by Maxim and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Bio/Techniques* 19:448), including sequencing by mass spectrometry (see, e.g., PCT Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the GPCR-like gene include methods in which protection from cleavage agents is used to detect mismatched bases in RNA/RNA or RNA/DNA heteroduplexes (Myers et al. (1985) *Science* 230:1242). See, also Cotton et al. (1988) *Proc. Natl. Acad. Sci. USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more "DNA mismatch repair" enzymes that recognize mismatched base pairs in double-stranded DNA in defined systems for detecting and mapping point mutations in GPCR-like cDNAs obtained from samples of cells. See, e.g., Hsu et al. (1994) *Carcinogenesis* 15:1657–1662. According to an exemplary embodiment, a probe based on a GPCR-like sequence, e.g., a wild-type GPCR-like sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in GPCR-like genes. For example, single-strand conformation polymorphism (SSCP) may be used to detect differences in electrophoretic mobility between mutant and wild-type nucleic acids (Orita et al. (1989) *Proc. Natl. Acad. Sci. USA* 86:2766; see also Cotton (1993) *Mutat. Res.* 285:125–144; Hayashi (1992) *Genet. Anal. Tech. Appl.* 9:73–79). The sensitivity of the assay may be enhanced by using RNA (rather than DNA), in which the secondary structure is more sensitive to a change in sequence. In a preferred embodiment, the subject method utilizes heteroduplex analysis to separate double-stranded heteroduplex molecules on the basis of changes in electrophoretic mobility (Keen et al. (1991) *Trends Genet.* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found (Saiki et al. (1986) *Nature* 324:163); Saiki et al. (1989) *Proc. Natl. Acad. Sci. USA* 86:6230). Such allele-specific oligonucleotides are hybridized to PCR-amplified target DNA or a number of different mutations when the oligonucleotides are attached to the hybridizing membrane and hybridized with labeled target DNA.

Alternatively, allele-specific amplification technology, which depends on selective PCR amplification, may be used in conjunction with the instant invention. Oligonucleotides used as primers for specific amplification may carry the mutation of interest in the center of the molecule so that amplification depends on differential hybridization (Gibbs et al. (1989) *Nucleic Acids Res.* 17:2437–2448) or at the extreme 3' end of one primer where, under appropriate conditions, mismatch can prevent or reduce polymerase extension (Prossner (1993) *Tibtech* 11:238). In addition, it may be desirable to introduce a novel restriction site in the region of the mutation to create cleavage-based detection (Gasparini el al. (1992) *Mol. Cell Probes* 6:1). It is anticipated that in certain embodiments amplification may also be performed using Taq ligase for amplification (Barany (1991) *Proc. Natl. Acad. Sci. USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing prepackaged diagnostic kits comprising at least one probe nucleic acid or antibody reagent described herein, which may be conveniently used, e.g., in clinical settings to diagnosed patients exhibiting symptoms or family history of a disease or illness involving a GPCR-like gene.

4. Pharmacogenomics

Agents, or modulators that have a stimulatory or inhibitory effect on GPCR-like activity (e.g., GPCR-like gene expression) as identified by a screening assay described herein, can be administered to individuals to treat (prophylactically or therapeutically) disorders associated with aberrant GPCR-like activity as well as to modulate the phenotype of an immune response. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of GPCR-like protein, expression of GPCR-like nucleic acid, or mutation content of GPCR-like genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) *Clin. Chem.* 43(2):254–266. In general, two types of pharmacogenetic conditions can be differentiated. Genetic conditions transmitted as a single factor altering the way drugs act on the body are referred to as "altered drug action." Genetic conditions transmitted as single factors altering the way the body acts on drugs are referred to as "altered drug metabolism". These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a GPCR-like molecule or GPCR-like modulator of the invention as well as tailoring the dosage and/or therapeutic regimen of treatment with a GPCR-like molecule or GPCR-like modulator of the invention.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, an "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drug's target is known (e.g., a GPCR-like protein of the present invention), all common variants of that gene can be fairly easily identified in the population and it can be determined if having one version of the gene versus another is associated with a particular drug response.

Alternatively, a method termed the "gene expression profiling", can be utilized to identify genes that predict drug response. For example, the gene expression of an animal dosed with a drug (e.g., a GPCR-like molecule or GPCR-like modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a GPCR-like molecule or GPCR-like modulator of the invention, such as a modulator identified by one of the exemplary screening assays described herein.

The present invention further provides methods for identifying new agents, or combinations, that are based on identifying agents that modulate the activity of one or more of the gene products encoded by one or more of the GPCR-like genes of the present invention, wherein these products may be associated with resistance of the cells to a therapeutic agent. Specifically, the activity of the proteins encoded by the GPCR-like genes of the present invention can be used as a basis for identifying agents for overcoming agent resistance. By blocking the activity of one or more of the resistance proteins, target cells, e.g., hepatic stellate cells, will become sensitive to treatment with an agent that the unmodified target cells were resistant to.

Monitoring the influence of agents (e.g., drugs) on the expression or activity of a GPCR-like protein can be applied in clinical trials. For example, the effectiveness of an agent determined by a screening assay as described herein to increase GPCR-like gene expression, protein levels, or upregulate GPCR-like activity, can be monitored in clinical trials of subjects exhibiting decreased GPCR-like gene expression, protein levels, or downregulated GPCR-like activity. Alternatively, the effectiveness of an agent determined by a-screening assay to decrease GPCR-like gene expression, protein levels, or downregulate GPCR-like activity, can be monitored in clinical trials of subjects exhibiting increased GPCR-like gene expression, protein levels, or upregulated GPCR-like activity. In such clinical trials, the expression or activity of a GPCR-like gene, and preferably, other genes that have been implicated in, for example, a GPCR-like-associated disorder can be used as a "read out" or markers of the phenotype of a particular cell.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, a PM will show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of GPCR-like protein, expression of GPCR-like nucleic acid, or mutation content of GPCR-like genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a GPCR-like modulator, such as a modulator identified by one of the exemplary screening assays described herein.

5. Monitoring of Effects During Clinical Trials

Monitoring the influence of agents (e.g., drugs, compounds) on the expression or activity of GPCR-like genes (e.g., the ability to modulate aberrant cell proliferation and/or differentiation) can be applied not only in basic drug screening but also in clinical trials. For example, the effectiveness of an agent, as determined by a screening assay as described herein, to increase or decrease GPCR-like gene expression, protein levels, or protein activity, can be monitored in clinical trials of subjects exhibiting decreased or increased GPCR-like gene expression, protein levels, or protein activity. In such clinical trials, GPCR-like expression or activity and preferably that of other genes that have been implicated in for example, a cellular proliferation disorder, can be used as a marker of the immune responsiveness of a particular cell.

For example, and not by way of limitation, genes that are modulated in cells by treatment with an agent (e.g., compound, drug, or small molecule) that modulates GPCR-like activity (e.g., as identified in a screening assay described herein) can be identified. Thus, to study the effect of agents on cellular proliferation disorders, for example, in a clinical trial, cells can be isolated and RNA prepared and analyzed for the levels of expression of GPCR-like genes and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of GPCR-like genes or other genes. In this way, the gene expression pattern can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (1) obtaining a preadministration sample from a subject prior to administration of the agent; (2) detecting the level of expression of a GPCR-like protein, mRNA, or genomic DNA in the preadministration sample; (3) obtaining one or more post-administration samples from the subject; (4) detecting the level of expression or activity of the GPCR-like protein, mRNA, or genomic DNA in the postadministration samples; (5) comparing the level of expression or activity of the GPCR-like protein, mRNA, or genomic DNA in the preadministration sample with the GPC GPCR-like R protein, mRNA, or genomic DNA in the postadministration sample or samples; and (vi) altering the administration of the agent to the subject accordingly to bring about the desired effect, i.e., for example, an increase or a decrease in the expression or activity of a GPCR-like protein.

C. Methods of Treatment

The present invention provides for both prophylactic and therapeutic methods of treating a subject at risk of (or susceptible to) a disorder or having a disorder associated with aberrant GPCR-like expression or activity. Additionally, the compositions of the invention find use in modulating the treatment of disorders described herein. Thus, therapies for immune, inflammatory, hematologic, fibrotic, hepatic, and respiratory disorders; disorders associated with the following cells or tissues: lymph node; spleen; thymus; brain; lung; skeletal muscle; fetal liver; tonsil; colon; heart; liver; peripheral blood mononuclear cells (PBMC); $CD34^+$; bone marrow cells; neonatal umbilical cord blood (CB $CD34^+$); leukocytes from G-CSF treated patients (mPB leukocytes); $CD14^+$ cells; monocytes; hepatic stellate cells; fibrotic liver; kidney; spinal cord; and dermal and lung fibroblasts; are encompassed herein.

I . Prophylactic Methods

In one aspect, the invention provides a method for preventing in a subject a disease or condition associated with an aberrant GPCR-like expression or activity by administering to the subject an agent that modulates GPCR-like expression or at least one GPCR-like gene activity. Subjects at risk for a disease that is caused, or contributed to, by aberrant GPCR-like expression or activity can be identified by, for example, any or a combination of diagnostic or prognostic assays as described herein. Administration of a prophylactic agent can occur prior to the manifestation of symptoms characteristic of the GPCR-like aberrancy, such that a disease or disorder is prevented or, alternatively, delayed in its progression. Depending on the type of GPCR-like aberrancy, for example, a GPCR-like agonist or GPCR-like antagonist agent can be used for treating the subject. The appropriate agent can be determined based on screening assays described herein.

2. Therapeutic Methods

Another aspect of the invention pertains to methods of modulating GPCR-like expression or activity for therapeutic purposes. The modulatory method of the invention involves contacting a cell with an agent that modulates one or more of the activities of GPCR-like protein activity associated with the cell. An agent that modulates GPCR-like protein activity can be an agent as described herein, such as a nucleic acid or a protein, a naturally-occurring cognate ligand of a GPCR-like protein, a peptide, a GPCR peptidomimetic, or other small molecule. In one embodiment, the agent stimulates one or more of the biological activities of GPCR-like protein. Examples of such stimulatory agents include active GPCR-like protein and a nucleic acid molecule encoding a GPCR-like protein that has been introduced into the cell. In another embodiment, the agent inhibits one or more of the biological activities of GPCR-like protein. Examples of such inhibitory agents include antisense GPCR-like nucleic acid molecules and anti-GPCR-like antibodies.

These modulatory methods can be performed in vitro (e.g., by culturing the cell with the agent) or, alternatively, in vivo (e.g, by administering the agent to a subject). As such, the present invention provides methods of treating an individual afflicted with a disease or disorder characterized by aberrant expression or activity of a GPCR-like protein or nucleic acid molecule. In one embodiment, the method involves administering an agent (e.g., an agent identified by a screening assay described herein), or a combination of agents, that modulates (e.g., upregulates or downregulates) GPCR-like expression or activity. In another embodiment, the method involves administering a GPCR-like protein or nucleic acid molecule as therapy to compensate for reduced or aberrant GPCR-like expression or activity.

Stimulation of GPCR activity is desirable in situations in which a GPCR-like protein is abnormally downregulated and/or in which increased GPCR-like activity is likely to have a beneficial effect. Conversely, inhibition of GPCR-like activity is desirable in situations in which GPCR-like activity is abnormally upregulated and/or in which decreased GPCR-like activity is likely to have a beneficial effect.

This invention is further illustrated by the following examples, which should not be construed as limiting.

EXPERIMENTAL

Example 1

Isolation of h15571

The clone h15571 was isolated from human thymus and spleen cDNA libraries. The identified clone h15571 encodes a transcript of approximately 6.09 Kb (corresponding cDNA set forth in SEQ ID NO:1). Nucleotides 366–4014 of this transcript represent an open reading frame that encodes a predicted 1338 amino acid polypeptide (SEQ ID NO:2).

An analysis of the h15571 GPCR-like amino acid sequence for physico-chemical chearacteristis, such as αβ turn and coil regions, hydrophilicity, amphipathic regions, flexible regions, antigenic index, and surface probability plot, is shown in FIG. 3.

A search of the nucleotide and protein databases revealed that h15571 shares similarity with other sequences, primarily in the C-terminal portion. The closest similarity resides with human cDNA DKFZp434C211 (GenBank Accession No. AL110244). Nucleotides 2986–5685 of SEQ ID NO:1 share approximately 99.4% sequence identity with this cDNA, as determined by global pairwise alignment. This cDNA encodes a hypothetical uncharacterized protein (GenBank Accession No. CAB53694, having 100% identity with amino acid residues 999–1338 of SEQ ID NO:2, the protein encoded by h15571, as determined by local pairwise alignment (BESTFIT). Local pairwise alignment (using BESTFIT) of the h15571 polypeptide indicates this protein shares sequence similarity to other GPCR proteins. Specifically, amino acid residues 695–944 of SEQ ID NO:2 share approximately 41.6% similarity and 30.5% identity with amino acid residues 2411–2646 of a mouse seven-pass transmembrane receptor precursor (GenBank Accession No. AAC68836); amino acid residues 689–946 of SEQ ID NO:2 share approximately 37.7% similarity and 30.5% identity with human MEGF2, a seven-pass transmembrane protein (GenBank Accession No. BAA32464); and amino acid residues 703–946 of SEQ ID NO:2 share approximately 37.8% similarity and 25.2% identity with amino acid residues 703–946 of rat MEGF2, a seven-pass transmembrane protein (GenBank Accession No. ABB32459).

Example 2 h115571 Expression Analysis

Total RNA was prepared from various human tissues by a single step extraction method using RNA STAT-60 according to the manufacturer's instructions (TelTest, Inc). Each RNA preparation was treated with DNase I (Ambion) at 37° C. for 1 hour. DNAse I treatment was determined to be complete if the sample required at least 38 PCR amplification cycles to reach a threshold level of flourescence using β-2 microglobulin as an internal amplicon reference. The integrity of the RNA samples following DNase I treatment was confirmed by agardse gel electrophoresis and ethidium bromide staining.

After phenol extraction, cDNA was prepared from the sample using the SUPERSCRIPT™ Choice System following the manufacturer's instructions (GibcoBRL). A negative control of RNA without reverse transcriptase was mock reverse transcribed for each RNA sample.

Expression of the novel h15571 GPCR-like gene sequence was measured by TaqMan® quantitative PCR (Perkin Elmer Applied Biosystems) in cDNA prepared from the following normal human tissues: lymph node, spleen, thymus, brain, lung, skeletal muscle, fetal liver, tonsil, colon, heart, and normal and fibrotic liver; the following primary cells: resting and phytohemaglutinin (PHA) activated peripheral blood mononuclear cells (PBMC); resting and PHA activated $CD3^+$ cells, $CD4^+$ and $CD8^+$ T cells; Th1 and Th2 cells stimulated for six or 48 hours with anti-CD3 antibody; resting and lipopolysaccharide (LPS) activated $CD19^+$ B cells; resting and LPS activated $CD19^+$ cells from tonsil; $CD34^+$ cells from mobilized peripheral blood (mPB $CD34^+$), adult resting bone marrow (ABM $CD34^+$), G-CSF mobilized bone marrow (mBM $CD34^+$), and neonatal umbilical cord blood (CB $CD34^+$); G-CSF mobilized peripheral blood leukocytes (mPB leukocytes) and $CD34^+$ cells purified from mPB leukocytes (mPB $CD34^+$); $CD14^+$ cells; granulocytes; hepatic stellate cells maintained in serum-free or fetal bovine serum (FBS) containing medium; resting and activated (phorbol 12-myristate 13-acetate (TPA) and ionomycin) normal human liver hepatocytes (NHLH); and fibroblasts (NHDF, normal human dermal fibroblasts; NHLF, normal human lung fibroblasts) mock stimulated or stimulated with transforming growth factor β (TGF-β). Transformed human cell lines included K526, an erythroleukemia; HL60, an acute promyelocytic leukemia; Jurkat, a T cell leukemia; HEK 293, epithelial cells from embryonic kidney transformed with adenovirus 5 DNA; and Hep3B hepatocellular liver carcinoma cells cultured in normal (HepB normoxia) or reduced oxygen tension (Hep3B hypoxia), or mock stimulated or stimulated with TGF-β.

Probes were designed by PrimerExpress software (PE Biosystems) based on the h15571 sequence. The primers and probes for expression analysis of h15571 and β-2 microglobulin were as follows:

h15571 ForwardPrimer GCATCACAGCTGCAGTCAACA (SEQ ID NO:3)

h15571 Reverse Primer GCCACACCAGCCAGCAGTA (SEQ ID NO:4)

h15571 TaqMan Probe CCACAACTACCGGGACCACAGCCC (SEQ ID NO:5)

β2 microglobulin Forward Primer CACCCCCACTGAAAAAGATGA (SEQ ID NO:6)

β-2 microglobulin Reverse Primer CTTAACTATCTTGGGCTGTGACAAAG (SEQ ID NO:7)

β-2 microglobulin TaqMan Probe TATGCCTGCCGTGTGAACCACGTG (SEQ ID NO:8)

The h15571 sequence probe was labeled using FAM (6-carboxyfluorescein), and the β2-microglobulin reference probe was labeled with a different fluorescent dye, VIC. The differential labeling of the target GPCR-like sequence and internal reference gene thus enabled measurement in the same well. Forward and reverse primers and the probes for both β2-microglobulin and the target h15571 sequence were added to the TaqMan® Universal PCR Master Mix (PE Applied Biosystems). Although the final concentration of primer and probe could vary, each was internally consistent within a given experiment. A typical experiment contained 200 nM of forward and reverse primers plus 100 nM probe for β-2 microglobulin and 600 nM forward and reverse primers plus 200 nM probe for the target h15571 sequence. TaqMan matrix experiments were carried out on an ABI PRISM 7700 Sequence Detection System (PE Applied Biosystems). The thermal cycler conditions were as follows: hold for 2 min at 50° C. and 10 min at 95° C., followed by two-step PCR for 40 cycles of 95° C. for 15 sec followed by 60° C. for 1 min.

The following method was used to quantitatively calculate h15571 expression in the various tissues relative to β2 microglobulin expression in the same tissue. The threshold cycle (Ct) value is defined as the cycle at which a statistically significant increase in fluorescence is detected. A lower Ct value is indicative of a higher mRNA concentration. The Ct value of the h15571 sequence is normalized by subtracting the Ct value of the β-2 microglobulin gene to obtain a $_{\Delta}Ct$ value using the following formula: $_{\Delta}Ct=Ct_{h15571}-Ct_{\beta\text{-}2\ microglobulin}$. Expression is then calibrated against a cDNA sample showing a comparatively low level of expression of the h15571 sequence. The $_{\Delta}Ct$ value for the calibrator sample is then subtracted from $_{\Delta}Ct$ for each tissue sample according to the following formula: $_{\Delta\Delta}Ct={}_{\Delta}Ct-_{sample}-{}_{\Delta}Ct-_{calibrator}$. Relative expression is then calculated using the arithmetic formula given by $2^{-\Delta\Delta Ct}$. Expression of the target h15571 sequence in each of the tissues tested was then graphically represented as discussed in more detail below.

Figure 4:
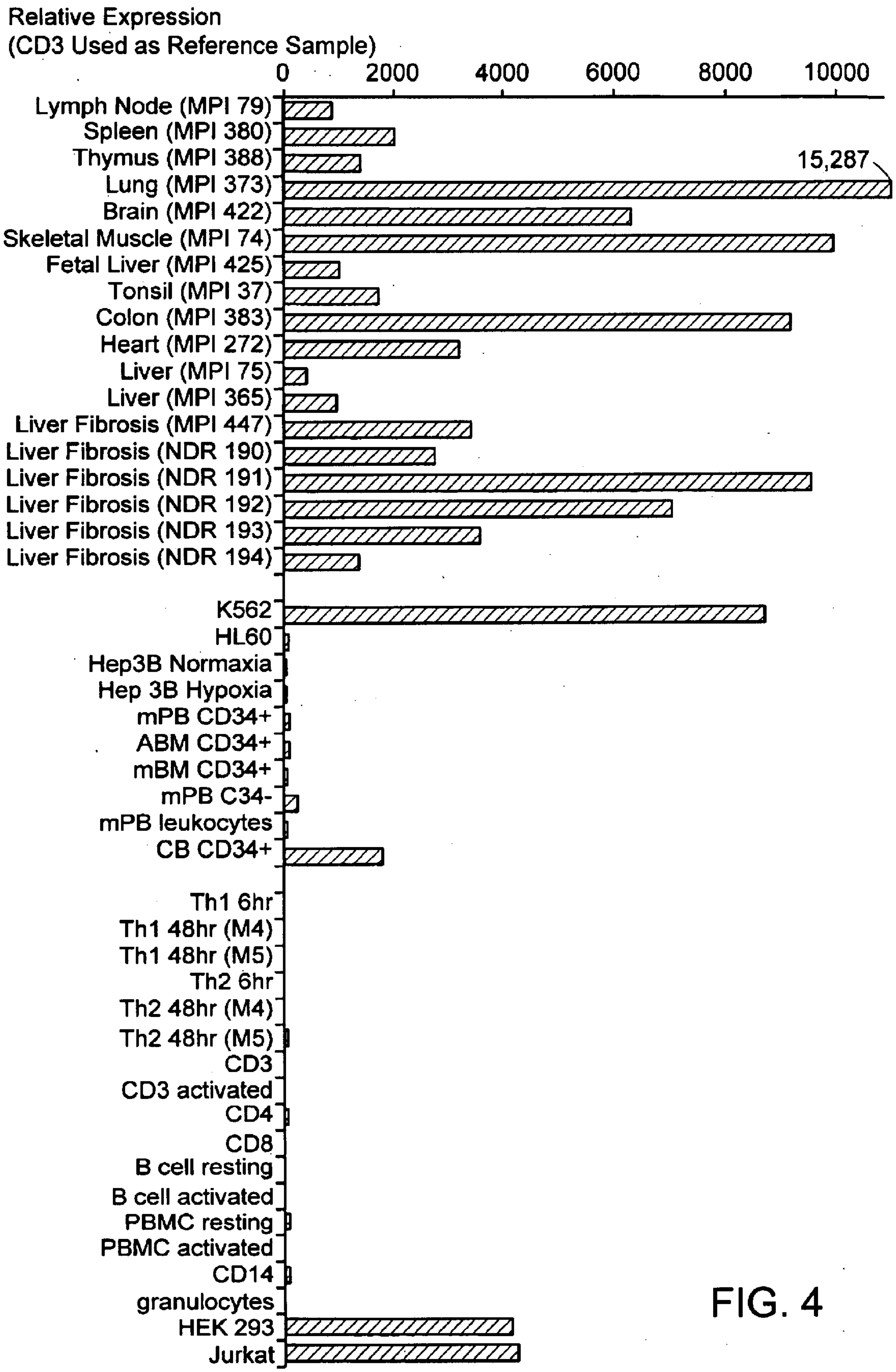
FIG. 4 shows expression of h15571 in various tissues and cell types relative to expression in human $CD3^+$ cells.

FIG. 4 shows expression of h15571 as determined in a broad panel of tissues and cell lines as described above, relative to expression in $CD3^{+}$T cells. The results indicate significant expression in lung, skeletal muscle, colon, fibrotic liver, and the K562 cell line; moderate expression in brain, and in the HEK 293 and Jurkat cell lines; and low level expression in lymph node, spleen, thymus, fetal liver, tonsil, heart, normal liver, and CB $CD34^{+}$ cells.

Figure 5:
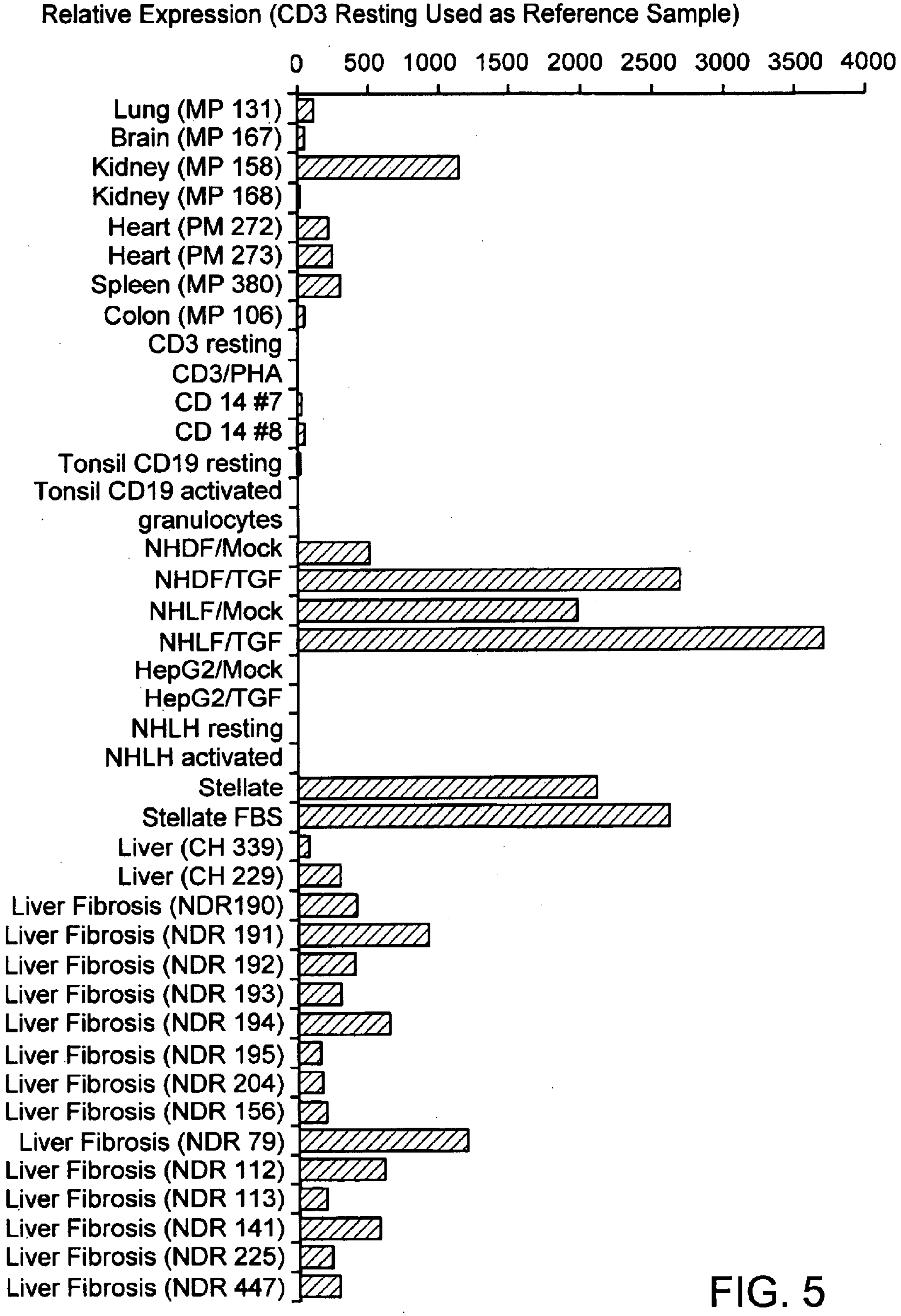
FIG. 5 shows expression of h15571 in various tissues and cell types relative to expression in human $CD3^+$ resting cells.

FIG. 5 shows expression of h15571 in various tissues and cell lines as described above, relative to expression in $CD3^{+}$ resting cells. The results indicate significant expression in normal human dermal and lung fibroblasts, and in hepatic stellate cells, which are involved in liver fibrosis.

Figure 6:
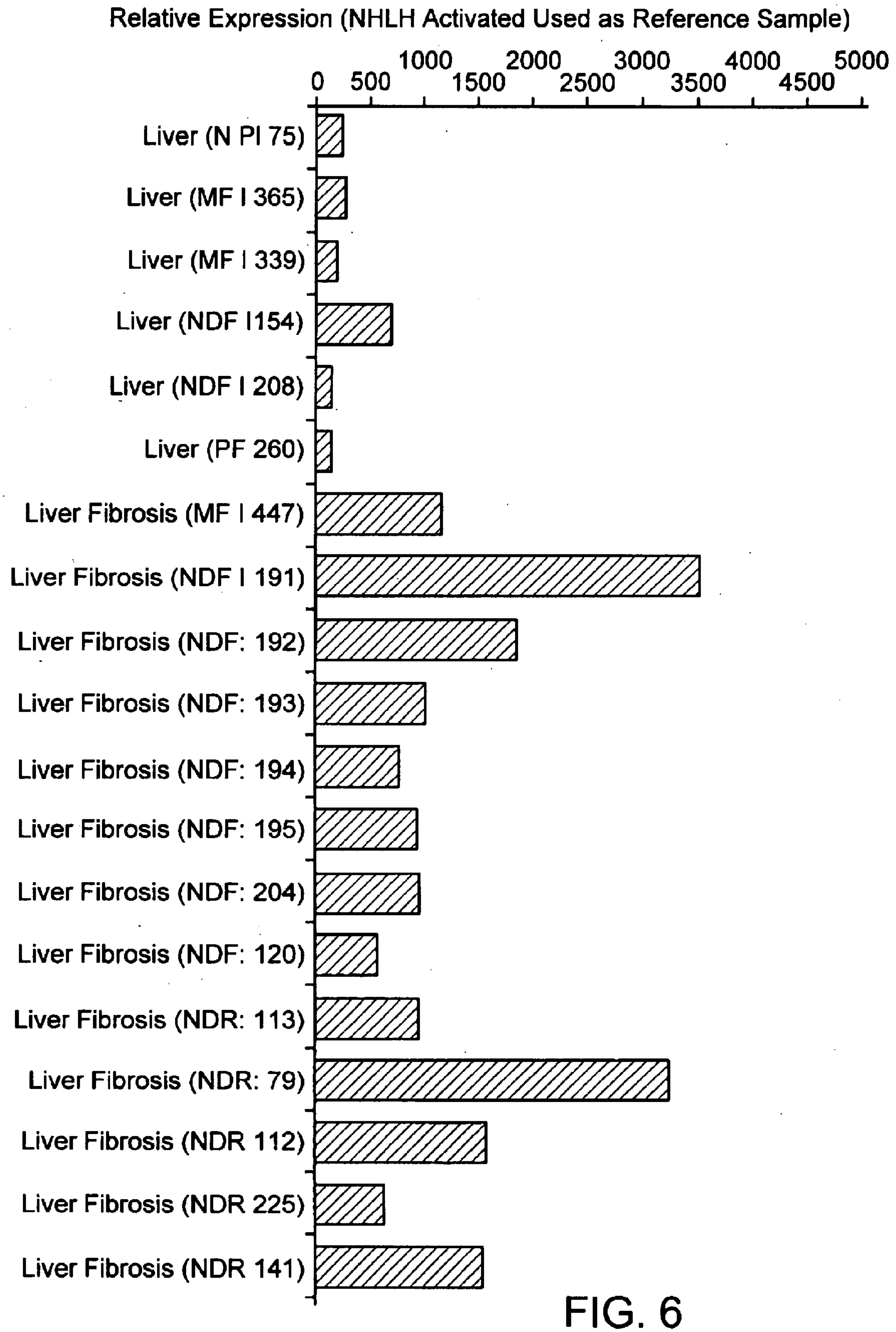
FIG. 6 shows expression of h15571 in normal liver and fibrotic liver samples relative to activated normal human liver hepatocytes (NHLH-activated).

The high expression observed in fibrotic liver samples was reexamined in a comparison of h15571 expression in thirteen fibrotic liver samples against six normal liver samples (see FIG. 6). The six samples taken from patients with no histological or clinical evidence of liver disease showed minimal expression of h15571. The thirteen samples from patients with histologically defined liver fibrosis, of mixed aetologies including chronic alcohol induced fibrosis, cryptogenic cirrhosis and primary biliary disease, showed upregulation of h15571 to differing degrees.

Figure 7:
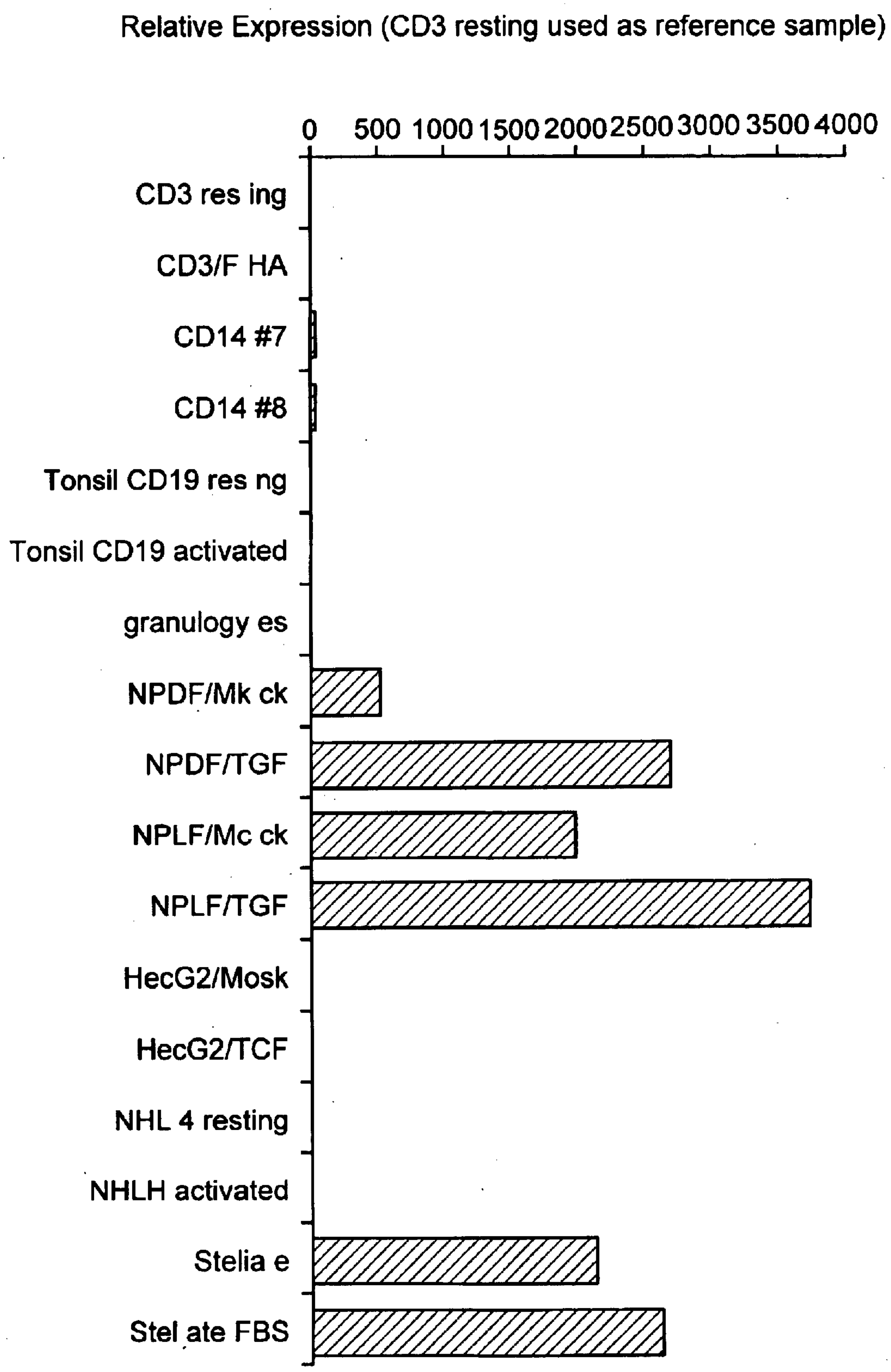
FIG. 7 shows expression of h15571 in hepatic stellate cells and fibroblasts relative to $CD3^+$ resting cells.

Isolated cells from this study were used to localize the expression of h15571 to the component cells of the liver or infiltrating inflammatory cells. h15571 expression was seen to be restricted to stellate cells and fibroblasts (NHDF=normal human dermal fibroblasts; NHLF=normal human lung fibroblasts). Activation with either transforming growth factor β (TGF-β) or fetal bovine serum (FBS) was seen to further increase the expression of h15571 in these cells (FIG. 7).

Figure 8:
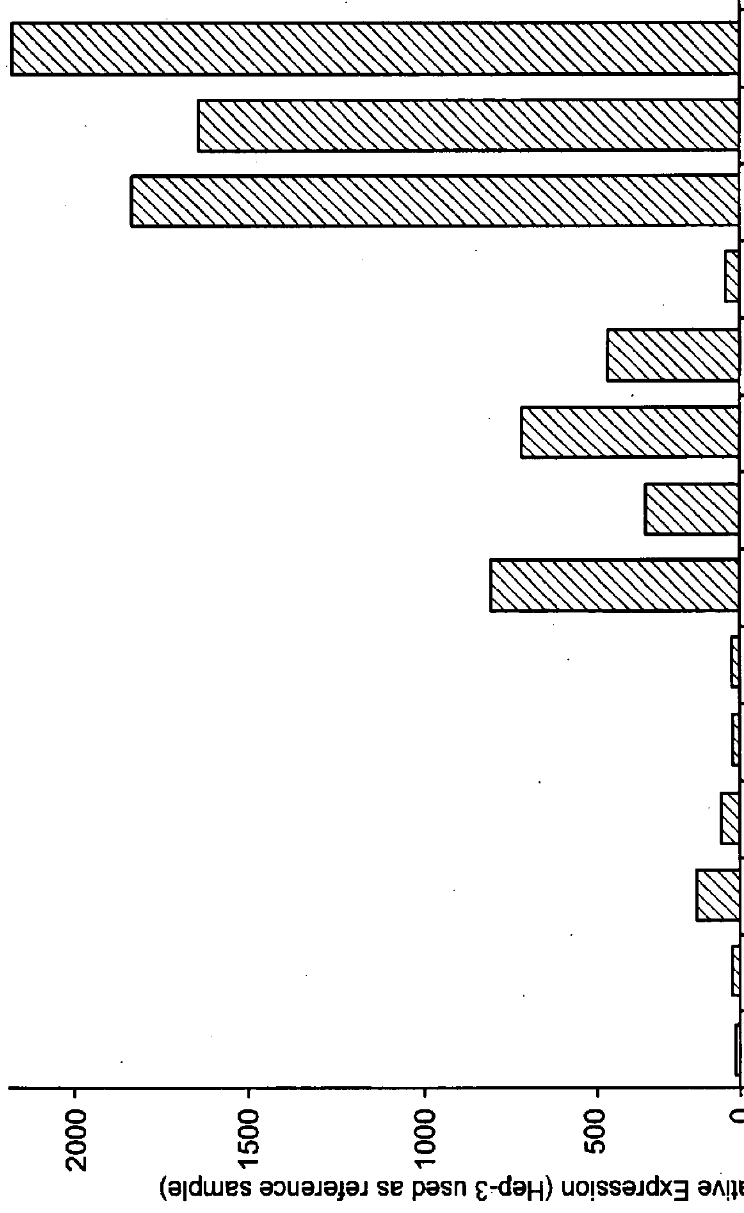
FIG. 8 contrasts expression of h15571 in normal liver versus fibrotic liver samples and liver stellate cells in their quiescent, passaged, resting, and serum-reactivated state relative to expression in hepatocytes 24 hours after TGF-β treatment.

The upregulation of h15571 in fibrotic liver samples, and the apparent localization of h15571 expression to activated stellate cells was examined further using similar TaqMan® PCR assays. FIG. 8 shows expression of h15571 as determined in several tissue and hepatic stellate cell samples relative to expression in hepatocytes 24 hours post-treatment with TGF (Hep-3 cells). Expression is clearly elevated in the human liver fibrotic samples, with low-level expression seen in human heart tissue, and nondetectable expression in normal human liver, brain, and kidney tissues. Furthermore, h15571 is not expressed in normal hepatocytes and those treated with PMA or TGF-β. Relative expression within hepatic stellate cells depends upon their physiological state. Thus, quiescent stellate cells show background levels of expression, while passaged stellate (fully activated stellate cells that have been exposed to prolonged culture), resting stellate, and stellate cells reactivated from their resting state with fetal bovine serum (FBS) have high levels of expression.

Figure 9:
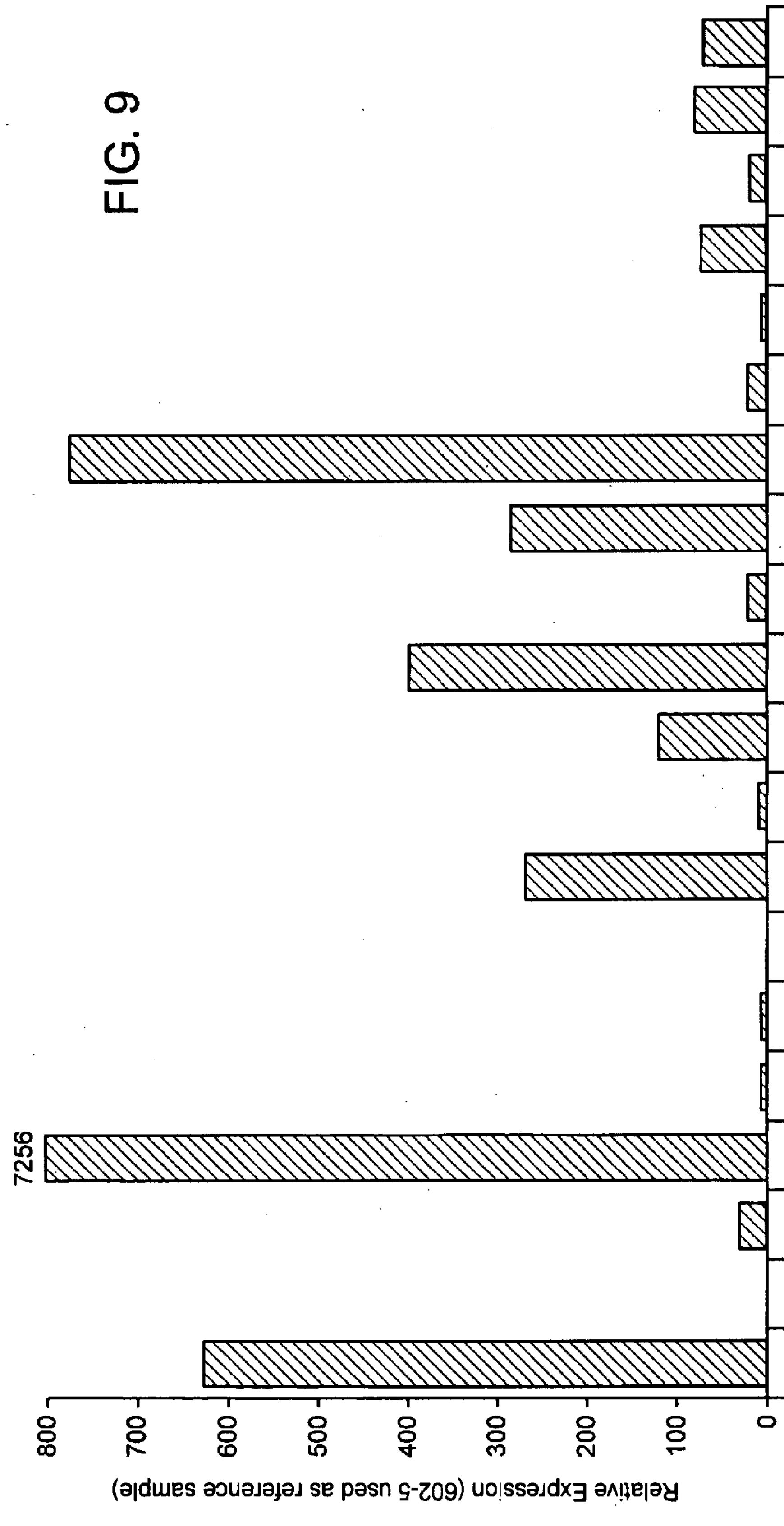
FIG. 9 shows rat 15571 expression in various tissues, including fibrotic liver samples induced by bile duct ligation (BDL) and porcine serum injection (serum) relative to controls (602–5, a normal rat liver).

Elevated expression levels in human liver fibrotic samples and in activated stellate cells indicates a potential role for h15571 in liver fibrosis. This potential role was examined further using rats and three models of liver fibrosis: bile duct ligation (see Kossakowska et al. (1998) *Amer. J. Pathol.* 153 (6): 1895), a surgical-base model; porcine serum injection (Paronetto and Popper (1966) *Amer. J. Pathol.* 49:1087, an immunological-based model; and carbon tetrachloride (CCL4) treatment, a toxicity-based model. FIG. 9 shows expression of rat 15571 as determined in several tissues. Significant expression is seen in brain and lung samples, and moderate expression in spinal cord samples. However, expression in normal liver, spleen, kidney, small intestine, and muscle samples is low or even nondetectable. Relative to normal liver, hi 5571 expression is elevated in rats that have undergone sham operation (i.e., control rats that have been exposed to surgical procedures such as anesthesia, but without bile duct ligation), and markedly elevated in livers of rats having their bile duct ligated for 14 days. Also, expression is elevated in fibrotic livers from rats treated with porcine serum for 7 weeks at 24 hours following the last injection of serum, though the effect is less dramatic than that seen with bile duct ligation.

Figure 10:
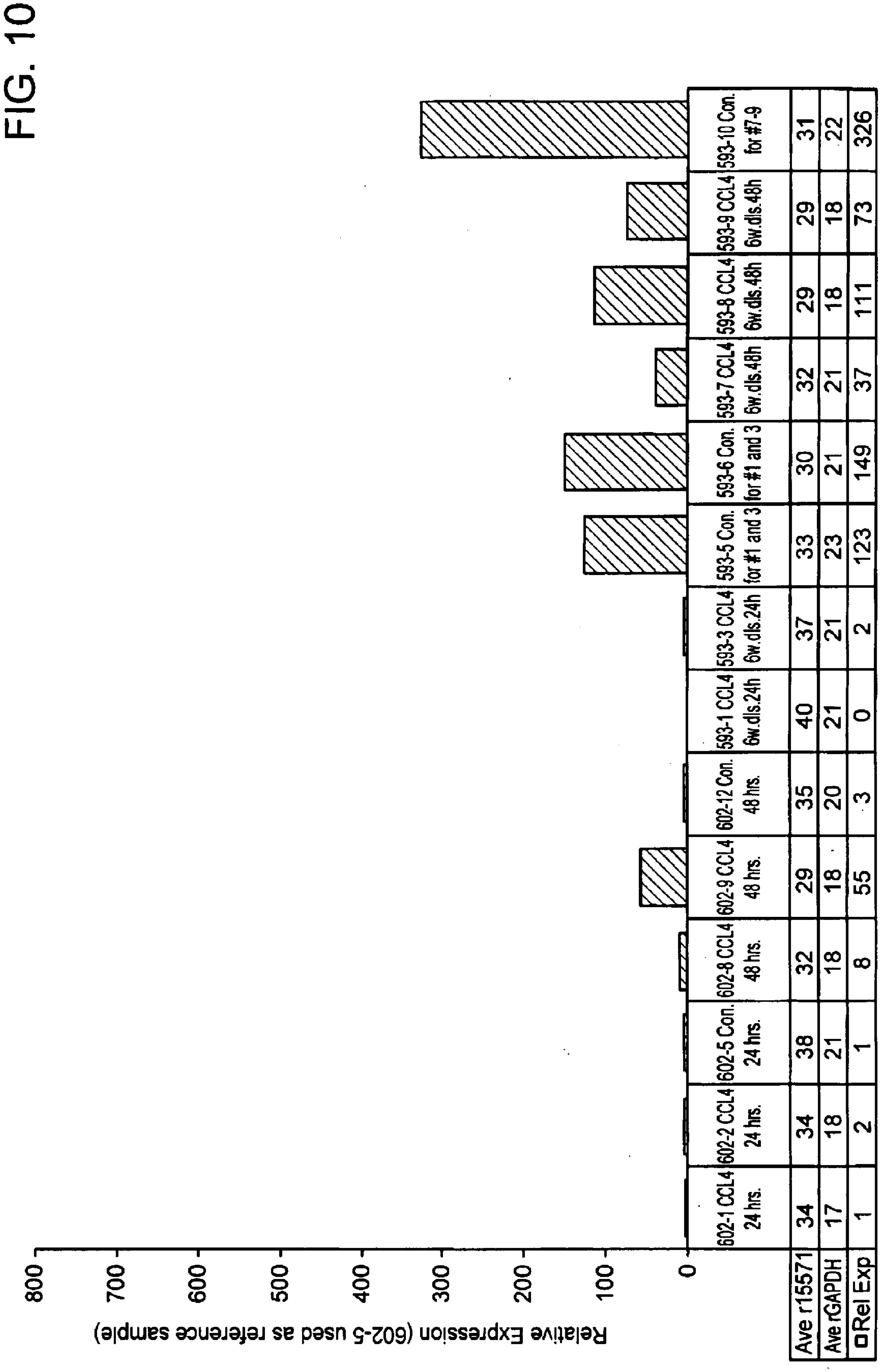
FIG. 10 shows rat 15571 expression in liver cell samples following treatment with carbon tetrachloride (CCL4) relative to controls 602–5.

FIG. 10 shows expression of rat 15571 in rat liver samples from rats treated with CCL4. This toxicity-based model indicates variable expression, but no clear demonstration of upregulation of the h15571 gene.

In summary; these TaqMan® assays reveal significant expression of h15571 in human lung, brain, skeletal muscle, colon, heart, and more particularly in liver fibrosis biopsies. Expression is high in activated hepatic stellate cells, TGF-beta-treated normal human lung fibroblasts, and TGF-beta-treated normal human dermal fibroblasts. Of particular significance is the low expression in normal human liver and nondetectable expression in normal human hepatocytes. Two rat models of liver fibrosis confirm that expression of this gene is elevated in the fibrotic liver tissues from treated animals relative to untreated control animals.

The h15571 protein, a secretin-like/GPCR-like protein, has restricted expression so that high levels of mRNA are detected only in activated hepatic stellate cells, not quiescent cells. Expression in fibrotic livers is elevated as compared to normal livers, and is undetectable in normal human hepatocytes and activated hepatocytes. These data indicate a role for h15571 in the process of fibrosis of the liver.

Example 3

In Situ Expression of h15571

Expression of h15571 was also examined by in situ hybridization of riboprobes to cellular mRNAs in the following human tissues: normal liver, fibrotic liver, normal fetal liver, kidney, colon adenocarcinoma, lung, and skeletal muscle. Sense and antisense riboprobes (RNA transcripts) of cDNA encoding h15571 were generated using $^{35}$S-dUTP, T3 polymerase, and T7 polymerase, and standard in vitro transcription reaction reagents.

Six μm sections of cryopreserved human tissue were prepared using a cryostat and annealed to glass slides, pre-hybed and hybridized to sense and antisense h15771 riboprobes according to standard protocols. Slides containing hybridized tissues and riboprobes were washed extensively (according to standard procedures), dipped in NTB-2 photoemulsion, and were allowed to expose for two weeks. Slides were developed and counterstained with hematoxylin to assist in identifying different subtypes of leukocytes. Data were recorded as pictures of these tissue sections as visualized under a microscope using bright and dark fields. The data from two separate experiments are summarized in Table I below.

High levels of h15571 expression were detected in some fibrotic adult livers and in skeletal muscle in two separate experiments. In those fibrotic liver samples exhibiting h15571 expression, activity was consistently detected in mesenchymal cells bordering fibrotic septae.

More specifically, expression of h15571 appears to be localized within activated stellate cells. These stellate cells are a type of myofibroblast believed to mediate the architectural changes that cause liver fibrosis. Thus activated stellate cells cause liver fibrosis, and it is these cells that express high levels of h15571 in liver fibrotic samples. No expression of h15571 was detected in tissue from: normal liver, normal fetal liver, kidney, colon adenocarcinoma, and lung.

The significant and remarkably consistent expression of h15571 in skeletal muscle is an indication of the relatedness of skeletal muscle cells and stellate cells. Myofibroblasts represent a cell type that shares properties with smooth muscle, such as contractability. Both types of cells/tissues express the protein alpha-actin, a mediator of contractability. Changes in this property may contribute to liver fibrosis.

TABLE 1

Expression Analysis of Human 15571 by In Situ Hybridization

| Tissue | h15571 | Comments |
|---|---|---|
| Normal Liver (NDR45) | – | |
| Normal Liver (NDR154) | – | |
| Fibrotic Liver (NDR112) | – | |
| Fibrotic Liver (NDR113) | – | |
| Fibrotic Liver (NDR126) | – | |
| Fibrotic Liver (NDR141) | – | |
| Fibrotic Liver (NDR190) | – | |
| Fibrotic Liver (NDR191) | + | Specific hybridization observed on mesenchymal cells bordering fibrotic septae. |
| Fibrotic Liver (NDR192) | + | Specific hybridization observed on mesenchymal cells bordering fibrotic septae. |
| Fibrotic Liver (NDR193) | + | Specific hybridization observed on mesenchymal cells bordering fibrotic septae. |
| Fibrotic Liver (NDR194) | – | |
| Fibrotic Liver (NDR195) | – | |
| Fibrotic Liver (NDR204) | + | Specific hybridization observed on mesenchymal cells bordering fibrotic septae. |
| Fibrotic Liver (NDR225) | – | |
| Normal Fetal Liver (BWH54) | – | |
| Normal Skeletal Muscle (PIT201) | + | |
| Normal Kidney (NDR169) | – | |
| Normal Lung (NDR44) | – | |
| Colon adenocarcinoma (NDR99) | – | |

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated nucleic acid molecule comprising the nucleotide sequence of SEQ ID NO:1 or a nucleotide sequence complementary to the nucleotide sequence of SEQ ID NO:1.

2. An isolated nucleic acid molecule comprising a nucleotide sequence encoding a polypeptide comprising the amino acid sequence of SEQ ID NO:2 or a nucleotide sequence complementary to a nucleotide sequence encoding a polypeptide comprising the amino acid sequence of SEQ ID NO:2.

3. An isolated nucleic acid molecule comprising a nucleotide sequence encoding a fusion polypeptide comprising the amino acid sequence of SEQ ID NO:2 and a heterologous polypeptide.

4. An isolated nucleic acid molecule of any one of claims 1–3, further comprising vector nucleic acid sequences.

5. An isolated host cell containing the nucleic acid molecule of any one of claims 1–3.

6. An isolated host cell containing a nucleic acid molecule of claim 4.

7. The host cell of claim 5 which is a mammalian cell.

8. The host cell of claim 6 which is a mammalian cell.

9. A method for producing a polypeptide comprising culturing the host cell of claim 5 under conditions in which the nucleic acid molecule is expressed and protein is produced.

10. A method for producing a polypeptide comprising culturing the host cell of claim 6 under conditions in which the nucleic acid molecule is expressed and protein is produced.

11. The method of claim 9 wherein said polypeptide comprises the amino acid sequence of SEQ ID NO:2.

12. The method of claim 10 wherein said polypeptide comprises the amino acid sequence of SEQ ID NO:2.

* * * * *

SEQUENCE LISTING

```
<160> NUMBER OF SEQ ID NOS:  24

<210> SEQ ID NO 1
<211> LENGTH: 6090
<212> TYPE: DNA
```

-continued

```
<213> ORGANISM: Homo Sapiens
<220> FEATURE:
<221> NAME/KEY: CDS
<222> LOCATION: (366)...(4379)
<221> NAME/KEY: misc_feature
<222> LOCATION: (1)...(6090)
<223> OTHER INFORMATION: n = A,T,C or G

<400> SEQUENCE: 1

ggagtcgacc cacgcgtccg cggcgcgatc cgctaggtcc cagcccagcg cccagcgagc     60

aggcgacgcg gaggggccgg gcctccagtg tcccgagggc cgggcgctga gactccggcc    120

gcgcagctgg gagctgcccg cgctgcgctg acagccgcgc cgacgtcctc cccgccgggg    180

cgctcgcagg acatgccccc ggggcgcggc ggcggggacc ccggggctcg cctccgccca    240

gggcccccct ccacgccctc gggagccccg ggcccccgct gagcactcct cccgcacgcc    300

tgggtccctc cggccggcgc gcagcccggc cccagcgctg tgggtccccg cggggcgatg    360

ggttg atg ggc gcc ggg gga cgc agg atg cgg ggg gcg ccc gcg cgc ctg    410
      Met Gly Ala Gly Gly Arg Arg Met Arg Gly Ala Pro Ala Arg Leu
       1               5                  10                  15

ctg ctg ccg ctg ctg ccg tgg ctc ctg ctg ctc ctg gcg ccc gag gct      458
Leu Leu Pro Leu Leu Pro Trp Leu Leu Leu Leu Leu Ala Pro Glu Ala
                 20                  25                  30

cgg ggc gcg ccc ggc tgc ccg cta tcc atc cgc agc tgc aag tgc tcg      506
Arg Gly Ala Pro Gly Cys Pro Leu Ser Ile Arg Ser Cys Lys Cys Ser
             35                  40                  45

ggg gag cgg ccc aag ggg ctg agc ggc ggc gtc cct ggc ccg gct cgg      554
Gly Glu Arg Pro Lys Gly Leu Ser Gly Gly Val Pro Gly Pro Ala Arg
         50                  55                  60

cgg agg gtg gtg tgc agc ggc ggg gac ctc ccg gag cct ccc gag ccc      602
Arg Arg Val Val Cys Ser Gly Gly Asp Leu Pro Glu Pro Pro Glu Pro
     65                  70                  75

ggc ctt ctg cct aac ggc acc gtt acc ctg ctc ttg agc aat aac aag      650
Gly Leu Leu Pro Asn Gly Thr Val Thr Leu Leu Leu Ser Asn Asn Lys
 80                  85                  90                  95

atc acg ggg ctc cgc aat ggc tcc ttc ctg gga ctg tca ctg ctg gag      698
Ile Thr Gly Leu Arg Asn Gly Ser Phe Leu Gly Leu Ser Leu Leu Glu
                100                 105                 110

aag ctg gac ctg agg aac aac atc atc agc aca gtg cag ccg ggc gcc      746
Lys Leu Asp Leu Arg Asn Asn Ile Ile Ser Thr Val Gln Pro Gly Ala
            115                 120                 125

ttc ctg ggc ctg ggg gag ctg aag cgt tta gat ctc tcc aac aac cgg      794
Phe Leu Gly Leu Gly Glu Leu Lys Arg Leu Asp Leu Ser Asn Asn Arg
        130                 135                 140

att ggc tgt ctc acc tcc gag acc ttc cag ggc ctc ccc agg ctt ctc      842
Ile Gly Cys Leu Thr Ser Glu Thr Phe Gln Gly Leu Pro Arg Leu Leu
    145                 150                 155

cga cta aac ata tct gga aac atc ttc tcc agt ctg caa cct ggg gtc      890
Arg Leu Asn Ile Ser Gly Asn Ile Phe Ser Ser Leu Gln Pro Gly Val
160                 165                 170                 175

ttt gat gag ctg cca gcc ctt aag gtt gtg gac ttg ggc acc gag ttc      938
Phe Asp Glu Leu Pro Ala Leu Lys Val Val Asp Leu Gly Thr Glu Phe
                180                 185                 190

ctg acc tgt gac tgc cac ctg cgc tgg ctg ctg ccc tgg gcc cag aat      986
Leu Thr Cys Asp Cys His Leu Arg Trp Leu Leu Pro Trp Ala Gln Asn
            195                 200                 205

cgc tcc ctg cag ctg tcg gaa cac acg ctc tgt gct tac ccc agt gcc     1034
Arg Ser Leu Gln Leu Ser Glu His Thr Leu Cys Ala Tyr Pro Ser Ala
        210                 215                 220

ctg cat gct cag gcc ctg ggc agc ctc cag gag gcc cag ctc tgc tgc     1082
```

-continued

```
Leu His Ala Gln Ala Leu Gly Ser Leu Gln Glu Ala Gln Leu Cys Cys
    225                 230                 235

gag ggg gcc ctg gag ctg cac aca cac cac ctc atc ccg tcc cta cgc      1130
Glu Gly Ala Leu Glu Leu His Thr His His Leu Ile Pro Ser Leu Arg
240                 245                 250                 255

caa gtg gtg ttc cag ggg gat cgg ctg ccc ttc cag tgc tct gcc agc      1178
Gln Val Val Phe Gln Gly Asp Arg Leu Pro Phe Gln Cys Ser Ala Ser
                260                 265                 270

tac ctg ggc aac gac acc cgc atc cgc tgg tac cac aac cga gcc cct      1226
Tyr Leu Gly Asn Asp Thr Arg Ile Arg Trp Tyr His Asn Arg Ala Pro
            275                 280                 285

gtg gag ggt gat gag cag gcg ggc atc ctc ctg gcc gag agc ctc atc      1274
Val Glu Gly Asp Glu Gln Ala Gly Ile Leu Leu Ala Glu Ser Leu Ile
        290                 295                 300

cac gac tgc acc ttc atc acc agt gag ctg acg ctg tct cac atc ggc      1322
His Asp Cys Thr Phe Ile Thr Ser Glu Leu Thr Leu Ser His Ile Gly
    305                 310                 315

gtg tgg gcc tca ggc gag tgg gag tgc acc gtg tcc atg gcc caa ggc      1370
Val Trp Ala Ser Gly Glu Trp Glu Cys Thr Val Ser Met Ala Gln Gly
320                 325                 330                 335

aac gcc agc aag aag gtg gag atc gtg gtg ctg gag acc tct gcc tcc      1418
Asn Ala Ser Lys Lys Val Glu Ile Val Val Leu Glu Thr Ser Ala Ser
                340                 345                 350

tac tgc ccc gcc gag cgt gtt gcc aac aac cgc ggg gac ttc agg tgg      1466
Tyr Cys Pro Ala Glu Arg Val Ala Asn Asn Arg Gly Asp Phe Arg Trp
            355                 360                 365

ccc cga act ctg gct ggc atc aca gcc tac cag tcc tgc ctg cag tat      1514
Pro Arg Thr Leu Ala Gly Ile Thr Ala Tyr Gln Ser Cys Leu Gln Tyr
        370                 375                 380

ccc ttc acc tca gtg ccc ctg ggc ggg ggt gcc ccg ggc acc cga gcc      1562
Pro Phe Thr Ser Val Pro Leu Gly Gly Gly Ala Pro Gly Thr Arg Ala
    385                 390                 395

tcc cgc cgg tgt gac cgt gcc ggc cgc tgg gag cca ggg gac tac tcc      1610
Ser Arg Arg Cys Asp Arg Ala Gly Arg Trp Glu Pro Gly Asp Tyr Ser
400                 405                 410                 415

cac tgt ctc tac acc aac gac atc acc agg gtg ctg tac acc ttc gtg      1658
His Cys Leu Tyr Thr Asn Asp Ile Thr Arg Val Leu Tyr Thr Phe Val
                420                 425                 430

ctg atg ccc atc aat gcc tcc aat gcg ctg acc ctg gct cac cag ctg      1706
Leu Met Pro Ile Asn Ala Ser Asn Ala Leu Thr Leu Ala His Gln Leu
            435                 440                 445

cgc gtg tac aca gcc gag gcc gct agc ttt tca gac atg atg gat gta      1754
Arg Val Tyr Thr Ala Glu Ala Ala Ser Phe Ser Asp Met Met Asp Val
        450                 455                 460

gtc tat gtg gct cag atg atc cag aaa ttt ttg ggt tat gtc gac cag      1802
Val Tyr Val Ala Gln Met Ile Gln Lys Phe Leu Gly Tyr Val Asp Gln
    465                 470                 475

atc aaa gag ctg gta gag gtg atg gtg gac atg gcc agc aac ctg atg      1850
Ile Lys Glu Leu Val Glu Val Met Val Asp Met Ala Ser Asn Leu Met
480                 485                 490                 495

ctg gtg gac gag cac ctg ctg tgg ctg gcc cag cgc gag gac aag gcc      1898
Leu Val Asp Glu His Leu Leu Trp Leu Ala Gln Arg Glu Asp Lys Ala
                500                 505                 510

tgc agc cgc atc gtg ggt gcc ctg gag cgc att ggg ggg gcc gcc ctc      1946
Cys Ser Arg Ile Val Gly Ala Leu Glu Arg Ile Gly Gly Ala Ala Leu
            515                 520                 525

agc ccc cat gcc cag cac atc tca gtg aat gcg agg aac gtg gca ttg      1994
Ser Pro His Ala Gln His Ile Ser Val Asn Ala Arg Asn Val Ala Leu
        530                 535                 540
```

-continued

```
gag gcc tac ctc atc aag ccg cac agc tac gtg ggc ctg acc tgc aca      2042
Glu Ala Tyr Leu Ile Lys Pro His Ser Tyr Val Gly Leu Thr Cys Thr
    545                 550                 555

gcc ttc cag agg agg gag gga ggg gtg ccg ggc aca cgg cca gga agc      2090
Ala Phe Gln Arg Arg Glu Gly Gly Val Pro Gly Thr Arg Pro Gly Ser
560                 565                 570                 575

cct ggc cag aac ccc cca cct gag ccc gag ccc cca gct gac cag cag      2138
Pro Gly Gln Asn Pro Pro Pro Glu Pro Glu Pro Pro Ala Asp Gln Gln
                580                 585                 590

ctc cgc ttc cgc tgc acc acc ggg agg ccc aat gtt tct ctg tcg tcc      2186
Leu Arg Phe Arg Cys Thr Thr Gly Arg Pro Asn Val Ser Leu Ser Ser
            595                 600                 605

ttc cac atc aag aac agc gtg gcc ctg gcc tcc atc cag ctg ccc ccg      2234
Phe His Ile Lys Asn Ser Val Ala Leu Ala Ser Ile Gln Leu Pro Pro
        610                 615                 620

agt cta ttc tca tcc ctt ccg gct gcc ctg gct ccc ccg gtg ccc cca      2282
Ser Leu Phe Ser Ser Leu Pro Ala Ala Leu Ala Pro Pro Val Pro Pro
    625                 630                 635

gac tgc acc ctg caa ctg ctc gtc ttc cga aat ggc cgc ctc ttc cac      2330
Asp Cys Thr Leu Gln Leu Leu Val Phe Arg Asn Gly Arg Leu Phe His
640                 645                 650                 655

agc cac agc aac acc tcc cgc cct gga gct gct ggg cct ggc aag agg      2378
Ser His Ser Asn Thr Ser Arg Pro Gly Ala Ala Gly Pro Gly Lys Arg
                660                 665                 670

cgt ggc gtg gcc acc ccc gtc atc ttc gca gga acc agt ggc tgt ggc      2426
Arg Gly Val Ala Thr Pro Val Ile Phe Ala Gly Thr Ser Gly Cys Gly
            675                 680                 685

gtg gga aac ctg aca gag cca gtg gcc gtt tcg ctg cgg cac tgg gct      2474
Val Gly Asn Leu Thr Glu Pro Val Ala Val Ser Leu Arg His Trp Ala
        690                 695                 700

gag gga gcc gaa cct gtg gcc gct tgg tgg agc cag gag ggg ccc ggg      2522
Glu Gly Ala Glu Pro Val Ala Ala Trp Trp Ser Gln Glu Gly Pro Gly
    705                 710                 715

gag gct ggg ggc tgg acc tcg gag ggc tgc cag ctc cgc tcc agc cag      2570
Glu Ala Gly Gly Trp Thr Ser Glu Gly Cys Gln Leu Arg Ser Ser Gln
720                 725                 730                 735

ccc aat gtc agc gcc ctg cac tgc cag cac ttg ggc aat gtg gcc gtg      2618
Pro Asn Val Ser Ala Leu His Cys Gln His Leu Gly Asn Val Ala Val
                740                 745                 750

ctc atg gag ctg agc gcc ttt ccc agg gag gtg ggg ggc gcc ggg gca      2666
Leu Met Glu Leu Ser Ala Phe Pro Arg Glu Val Gly Gly Ala Gly Ala
            755                 760                 765

ggg ctg cac ccc gtg gta tac ccc tgc acg gcc ttg ctg ctg ctc tgc      2714
Gly Leu His Pro Val Val Tyr Pro Cys Thr Ala Leu Leu Leu Leu Cys
        770                 775                 780

ctc ttc gcc acc atc atc acc tac atc ctc aac cac agc tcc atc cgt      2762
Leu Phe Ala Thr Ile Ile Thr Tyr Ile Leu Asn His Ser Ser Ile Arg
    785                 790                 795

gtg tcc cgg aaa ggc tgg cac atg ctg ctg aac ttg tgc ttc cac ata      2810
Val Ser Arg Lys Gly Trp His Met Leu Leu Asn Leu Cys Phe His Ile
800                 805                 810                 815

gcc atg acc tct gct gtc ttt gcg ggg ggc atc aca ctc acc aac tac      2858
Ala Met Thr Ser Ala Val Phe Ala Gly Gly Ile Thr Leu Thr Asn Tyr
                820                 825                 830

cag atg gtc tgc cag gcg gtg ggc atc acc ctg cac tac tcc tcc cta      2906
Gln Met Val Cys Gln Ala Val Gly Ile Thr Leu His Tyr Ser Ser Leu
            835                 840                 845

tcc acg ctg ctc tgg atg ggc gtg aag gcg cga gtg ctc cat aag gag      2954
Ser Thr Leu Leu Trp Met Gly Val Lys Ala Arg Val Leu His Lys Glu
        850                 855                 860
```

-continued

```
ctc acc tgg agg gca ccc cct ccg caa gaa ggg gac ccc gct ctg cct     3002
Leu Thr Trp Arg Ala Pro Pro Pro Gln Glu Gly Asp Pro Ala Leu Pro
    865                 870                 875

act ccc agt cct atg ctc cgg ttc tat ttg atc gct gga ggg att cca     3050
Thr Pro Ser Pro Met Leu Arg Phe Tyr Leu Ile Ala Gly Gly Ile Pro
880                 885                 890                 895

ctc att atc tgt ggc atc aca gct gca gtc aac atc cac aac tac cgg     3098
Leu Ile Ile Cys Gly Ile Thr Ala Ala Val Asn Ile His Asn Tyr Arg
                900                 905                 910

gac cac agc ccc tac tgc tgg ctg gtg tgg cgt cca agc ctt ggc gcc     3146
Asp His Ser Pro Tyr Cys Trp Leu Val Trp Arg Pro Ser Leu Gly Ala
            915                 920                 925

ttc tac atc cct gtg gct ttg att ctg ctc atc acc tgg atc tat ttc     3194
Phe Tyr Ile Pro Val Ala Leu Ile Leu Leu Ile Thr Trp Ile Tyr Phe
        930                 935                 940

ctg tgc gcc ggg cta cgc tta cgg ggt cct ctg gca cag aac ccc aag     3242
Leu Cys Ala Gly Leu Arg Leu Arg Gly Pro Leu Ala Gln Asn Pro Lys
    945                 950                 955

gcg ggc aac agc agg gcc tcc ctg gag gca ggg gag gag ctg agg ggt     3290
Ala Gly Asn Ser Arg Ala Ser Leu Glu Ala Gly Glu Glu Leu Arg Gly
960                 965                 970                 975

tcc acc agg ctc agg ggc agc ggc ccc ctc ctg agt gac tca ggt tcc     3338
Ser Thr Arg Leu Arg Gly Ser Gly Pro Leu Leu Ser Asp Ser Gly Ser
                980                 985                 990

ctt ctt gct act ggg agc gcg cga gtg ggg acg ccc ggg ccc ccg gag     3386
Leu Leu Ala Thr Gly Ser Ala Arg Val Gly Thr Pro Gly Pro Pro Glu
            995                 1000                1005

gat ggt gac agc ctc tat tct ccg gga gtc cag cta ggg gcg ctg gtg     3434
Asp Gly Asp Ser Leu Tyr Ser Pro Gly Val Gln Leu Gly Ala Leu Val
        1010                1015                1020

acc acg cac ttc ctg tac ttg gcc atg tgg gcc tgc ggg gct ctg gca     3482
Thr Thr His Phe Leu Tyr Leu Ala Met Trp Ala Cys Gly Ala Leu Ala
    1025                1030                1035

gtg tcc cag cgc tgg ctg ccc cgg gtg gtg tgc agc tgc ttg tac ggg     3530
Val Ser Gln Arg Trp Leu Pro Arg Val Val Cys Ser Cys Leu Tyr Gly
1040                1045                1050                1055

gtg gca gcc tcc gcc ctg ggc ctc ttc gtc ttc act cac cac tgt gcc     3578
Val Ala Ala Ser Ala Leu Gly Leu Phe Val Phe Thr His His Cys Ala
                1060                1065                1070

agg cgg agg gac gtg aga gcc tcg tgg cgc gcc tgc tgc ccc cct gcc     3626
Arg Arg Arg Asp Val Arg Ala Ser Trp Arg Ala Cys Cys Pro Pro Ala
            1075                1080                1085

tct ccc gcg gcc ccc cat gcc ccg ccc cgg gcc ctg ccc gcc gcc gca     3674
Ser Pro Ala Ala Pro His Ala Pro Pro Arg Ala Leu Pro Ala Ala Ala
        1090                1095                1100

gag gac ggt tcc ccg gtg ttc ggg gag ggg ccc ccc tcc ctc aag tcc     3722
Glu Asp Gly Ser Pro Val Phe Gly Glu Gly Pro Pro Ser Leu Lys Ser
    1105                1110                1115

tcc cca agc ggc agc agc ggc cat ccg ctg gct ctg ggc ccc tgc aag     3770
Ser Pro Ser Gly Ser Ser Gly His Pro Leu Ala Leu Gly Pro Cys Lys
1120                1125                1130                1135

ctc acc aac ctg cag ctg gcc cag agt cag gtg tgc gag gcg ggg gcg     3818
Leu Thr Asn Leu Gln Leu Ala Gln Ser Gln Val Cys Glu Ala Gly Ala
                1140                1145                1150

gcg gcc ggc ggg gaa gga gag ccg gag ccg gcg ggc acc cgg gga aac     3866
Ala Ala Gly Gly Glu Gly Glu Pro Glu Pro Ala Gly Thr Arg Gly Asn
            1155                1160                1165

ctc gcc cac cgc cac ccc aac aac gtg cac cac ggg cgt cgg gcg cac     3914
Leu Ala His Arg His Pro Asn Asn Val His His Gly Arg Arg Ala His
```

-continued

```
        1170                1175                1180

aag agc cgg gcc aag gga cac cgc gcg ggg gag gcc tgc ggc aag aac     3962
Lys Ser Arg Ala Lys Gly His Arg Ala Gly Glu Ala Cys Gly Lys Asn
    1185                1190                1195

cgg ctc aag gcc ctg cgc ggg ggc gcg gcg ggg gcg ctg gag ctg ctg     4010
Arg Leu Lys Ala Leu Arg Gly Gly Ala Ala Gly Ala Leu Glu Leu Leu
1200                1205                1210                1215

tcc agc gag agc ggc agt ctg cac aac agc ccc acc gac agc tac ctg     4058
Ser Ser Glu Ser Gly Ser Leu His Asn Ser Pro Thr Asp Ser Tyr Leu
                1220                1225                1230

ggc agc agc cgc aac agc ccg ggc gcc ggc ctg cag ctg gaa ggc gag     4106
Gly Ser Ser Arg Asn Ser Pro Gly Ala Gly Leu Gln Leu Glu Gly Glu
            1235                1240                1245

ccc atg ctc acg ccg tcc gag ggc agc gac acc agc gcc gcg ccg ctt     4154
Pro Met Leu Thr Pro Ser Glu Gly Ser Asp Thr Ser Ala Ala Pro Leu
        1250                1255                1260

tct gag gcg ggc cgg gca ggc cag cgc cgc agc gcc agc cgc gac agt     4202
Ser Glu Ala Gly Arg Ala Gly Gln Arg Arg Ser Ala Ser Arg Asp Ser
    1265                1270                1275

ctc aag ggc ggc ggc gcg ctg gag aag gag agc cat cgc cgc tcg tac     4250
Leu Lys Gly Gly Gly Ala Leu Glu Lys Glu Ser His Arg Arg Ser Tyr
1280                1285                1290                1295

ccg ctc aac gcc gcc agc cta aac ggc gcc ccc aag ggg ggc aag tac     4298
Pro Leu Asn Ala Ala Ser Leu Asn Gly Ala Pro Lys Gly Gly Lys Tyr
                1300                1305                1310

gac gac gtc acc ctg atg ggc gcg gag gta gcc agc ggc ggc tgc atg     4346
Asp Asp Val Thr Leu Met Gly Ala Glu Val Ala Ser Gly Gly Cys Met
            1315                1320                1325

aag acc gga ctc tgg aag agc gaa act acc gtc taaggtgggg cgggcgacgc   4399
Lys Thr Gly Leu Trp Lys Ser Glu Thr Thr Val
        1330                1335

ggtagacggg ctggccacgc ggctcgttcc cccgctcctc ggggccctcc aaggtgtctc   4459

cgtagtcagc aggttggagg cagaggagcc gatggctgga ggaagcccac aggcggatgt   4519

tccccacttg cctagagggc atccctctgg ggtagcgaca gacaatccca gaaacacgca   4579

taatacattt ccgtccagcc cggggcagtc tgactgtcgg tgccctccca ggaacgggga   4639

aggcctccgt ctgtgtgaaa gggcacagca catcccaggt gcaccctccc caagtactcc   4699

caccccgcct actgtccatg cggcctcact gggggccatc agcctcacca gcaaagcaga   4759

gatgagagcg tgggaactgt gttctttcct ccctgccctc tactgatttc agcccagccc   4819

ctgcctagat cctaggtccc ttttcctccc gagtttggct ggcacgagag ctagcccagc   4879

acatgaagca ggtgatgtta agtcacaagg tgctgctttt cagatccact atgcaagagg   4939

ggagggtggg gccacgtgaa aggcagctct agacatcaac cagtcctggg ggaggggagt   4999

gggaaccggg cacaactagg aacaatgcca ccattcccac aggagtggta cttaaaccag   5059

acagcagggt tcagaggtgg cacaccggga caaagctgag gccctgcacc tcaacagctg   5119

actgccaggt gcctgtgggt gaactgaggg gagtagaggg agagggcagg tggaactggg   5179

gcagaatcta gtcatgccct aaagctagtc ctgtaaacaa tggtgcccca gaaagctgca   5239

ggtggtgttt ggagaagcag ttacttttca gttacaagac ccatctccct agtctcagcc   5299

ttacaacacc acgggactaa ggaagagcac ttccttgcct ccgtaaggcc agaggaagaa   5359

ccatcccaat catttgatct ccagctccac agtagagaga aacctacaaa atgtcaaacc   5419

agcttcccga ctcccaggag ctcaagccaa gcccagaggc agtggctggg gtccctgcag   5479

gtcatgaggg gcctatgcct ttactccttt taaacaccag cacccgtctt ttccccaacc   5539
```

-continued taaaaccaac caccagcatt tcactacagg accaaatgga amccgaggga mccctgggtc 5599 ttgggaagaa camcaggaaa ccaaggtctg mcctagggtt ccctcccagt cttcacatca 5659 ctytggcctc atcmccaagg tgmcagagga cacaggggag ggggaaaacc cacacacact 5719 ccttggaatg ggtcctgtta tttatgcttg ctgcmcagac atattagaag aaaaaaaaaa 5779 agctttgtat tattcttcca catatgctgg ctgctgttta cacaccctgc caatgcctta 5839 gcactggaga gctttttgca atatgctggg gaaaggggag ggagggaatg aaagtgccaa 5899 agaaaacatg tttttaagaa ctcgggtttt atacaataga atgttttcta gcagatgcct 5959 cttgttttaa tatattaaaa ttttgcaaag ccctttgaag nataaaaaaa nagggcaaac 6019 gctagactag tctagagaaa aaacctccca ggnttccccc taanaactgg ggcgtagtgt 6079 ccctatnaac g 6090

<210> SEQ ID NO 2
<211> LENGTH: 1338
<212> TYPE: PRT
<213> ORGANISM: Homo Sapiens

<400> SEQUENCE: 2

```
Met Gly Ala Gly Gly Arg Arg Met Arg Gly Ala Pro Ala Arg Leu Leu
 1               5                  10                  15

Leu Pro Leu Leu Pro Trp Leu Leu Leu Leu Leu Ala Pro Glu Ala Arg
            20                  25                  30

Gly Ala Pro Gly Cys Pro Leu Ser Ile Arg Ser Cys Lys Cys Ser Gly
        35                  40                  45

Glu Arg Pro Lys Gly Leu Ser Gly Gly Val Pro Gly Pro Ala Arg Arg
    50                  55                  60

Arg Val Val Cys Ser Gly Gly Asp Leu Pro Glu Pro Pro Glu Pro Gly
65                  70                  75                  80

Leu Leu Pro Asn Gly Thr Val Thr Leu Leu Leu Ser Asn Asn Lys Ile
                85                  90                  95

Thr Gly Leu Arg Asn Gly Ser Phe Leu Gly Leu Ser Leu Leu Glu Lys
            100                 105                 110

Leu Asp Leu Arg Asn Asn Ile Ile Ser Thr Val Gln Pro Gly Ala Phe
        115                 120                 125

Leu Gly Leu Gly Glu Leu Lys Arg Leu Asp Leu Ser Asn Asn Arg Ile
    130                 135                 140

Gly Cys Leu Thr Ser Glu Thr Phe Gln Gly Leu Pro Arg Leu Leu Arg
145                 150                 155                 160

Leu Asn Ile Ser Gly Asn Ile Phe Ser Ser Leu Gln Pro Gly Val Phe
                165                 170                 175

Asp Glu Leu Pro Ala Leu Lys Val Val Asp Leu Gly Thr Glu Phe Leu
            180                 185                 190

Thr Cys Asp Cys His Leu Arg Trp Leu Leu Pro Trp Ala Gln Asn Arg
        195                 200                 205

Ser Leu Gln Leu Ser Glu His Thr Leu Cys Ala Tyr Pro Ser Ala Leu
    210                 215                 220

His Ala Gln Ala Leu Gly Ser Leu Gln Glu Ala Gln Leu Cys Cys Glu
225                 230                 235                 240

Gly Ala Leu Glu Leu His Thr His His Leu Ile Pro Ser Leu Arg Gln
                245                 250                 255

Val Val Phe Gln Gly Asp Arg Leu Pro Phe Gln Cys Ser Ala Ser Tyr
            260                 265                 270
```

-continued

```
Leu Gly Asn Asp Thr Arg Ile Arg Trp Tyr His Asn Arg Ala Pro Val
        275                 280                 285

Glu Gly Asp Glu Gln Ala Gly Ile Leu Leu Ala Glu Ser Leu Ile His
    290                 295                 300

Asp Cys Thr Phe Ile Thr Ser Glu Leu Thr Leu Ser His Ile Gly Val
305                 310                 315                 320

Trp Ala Ser Gly Glu Trp Glu Cys Thr Val Ser Met Ala Gln Gly Asn
                325                 330                 335

Ala Ser Lys Lys Val Glu Ile Val Val Leu Glu Thr Ser Ala Ser Tyr
            340                 345                 350

Cys Pro Ala Glu Arg Val Ala Asn Asn Arg Gly Asp Phe Arg Trp Pro
        355                 360                 365

Arg Thr Leu Ala Gly Ile Thr Ala Tyr Gln Ser Cys Leu Gln Tyr Pro
    370                 375                 380

Phe Thr Ser Val Pro Leu Gly Gly Gly Ala Pro Gly Thr Arg Ala Ser
385                 390                 395                 400

Arg Arg Cys Asp Arg Ala Gly Arg Trp Glu Pro Gly Asp Tyr Ser His
                405                 410                 415

Cys Leu Tyr Thr Asn Asp Ile Thr Arg Val Leu Tyr Thr Phe Val Leu
            420                 425                 430

Met Pro Ile Asn Ala Ser Asn Ala Leu Thr Leu Ala His Gln Leu Arg
        435                 440                 445

Val Tyr Thr Ala Glu Ala Ala Ser Phe Ser Asp Met Met Asp Val Val
    450                 455                 460

Tyr Val Ala Gln Met Ile Gln Lys Phe Leu Gly Tyr Val Asp Gln Ile
465                 470                 475                 480

Lys Glu Leu Val Glu Val Met Val Asp Met Ala Ser Asn Leu Met Leu
                485                 490                 495

Val Asp Glu His Leu Leu Trp Leu Ala Gln Arg Glu Asp Lys Ala Cys
            500                 505                 510

Ser Arg Ile Val Gly Ala Leu Glu Arg Ile Gly Gly Ala Ala Leu Ser
        515                 520                 525

Pro His Ala Gln His Ile Ser Val Asn Ala Arg Asn Val Ala Leu Glu
    530                 535                 540

Ala Tyr Leu Ile Lys Pro His Ser Tyr Val Gly Leu Thr Cys Thr Ala
545                 550                 555                 560

Phe Gln Arg Arg Glu Gly Gly Val Pro Gly Thr Arg Pro Gly Ser Pro
                565                 570                 575

Gly Gln Asn Pro Pro Pro Glu Pro Glu Pro Pro Ala Asp Gln Gln Leu
            580                 585                 590

Arg Phe Arg Cys Thr Thr Gly Arg Pro Asn Val Ser Leu Ser Ser Phe
        595                 600                 605

His Ile Lys Asn Ser Val Ala Leu Ala Ser Ile Gln Leu Pro Pro Ser
    610                 615                 620

Leu Phe Ser Ser Leu Pro Ala Ala Leu Ala Pro Pro Val Pro Pro Asp
625                 630                 635                 640

Cys Thr Leu Gln Leu Leu Val Phe Arg Asn Gly Arg Leu Phe His Ser
                645                 650                 655

His Ser Asn Thr Ser Arg Pro Gly Ala Ala Gly Pro Gly Lys Arg Arg
            660                 665                 670

Gly Val Ala Thr Pro Val Ile Phe Ala Gly Thr Ser Gly Cys Gly Val
        675                 680                 685
```

-continued

```
Gly Asn Leu Thr Glu Pro Val Ala Val Ser Leu Arg His Trp Ala Glu
    690                 695                 700

Gly Ala Glu Pro Val Ala Ala Trp Trp Ser Gln Glu Gly Pro Gly Glu
705                 710                 715                 720

Ala Gly Gly Trp Thr Ser Glu Gly Cys Gln Leu Arg Ser Ser Gln Pro
                725                 730                 735

Asn Val Ser Ala Leu His Cys Gln His Leu Gly Asn Val Ala Val Leu
            740                 745                 750

Met Glu Leu Ser Ala Phe Pro Arg Glu Val Gly Gly Ala Gly Ala Gly
        755                 760                 765

Leu His Pro Val Val Tyr Pro Cys Thr Ala Leu Leu Leu Leu Cys Leu
    770                 775                 780

Phe Ala Thr Ile Ile Thr Tyr Ile Leu Asn His Ser Ser Ile Arg Val
785                 790                 795                 800

Ser Arg Lys Gly Trp His Met Leu Leu Asn Leu Cys Phe His Ile Ala
                805                 810                 815

Met Thr Ser Ala Val Phe Ala Gly Gly Ile Thr Leu Thr Asn Tyr Gln
            820                 825                 830

Met Val Cys Gln Ala Val Gly Ile Thr Leu His Tyr Ser Ser Leu Ser
        835                 840                 845

Thr Leu Leu Trp Met Gly Val Lys Ala Arg Val Leu His Lys Glu Leu
    850                 855                 860

Thr Trp Arg Ala Pro Pro Pro Gln Glu Gly Asp Pro Ala Leu Pro Thr
865                 870                 875                 880

Pro Ser Pro Met Leu Arg Phe Tyr Leu Ile Ala Gly Gly Ile Pro Leu
                885                 890                 895

Ile Ile Cys Gly Ile Thr Ala Ala Val Asn Ile His Asn Tyr Arg Asp
            900                 905                 910

His Ser Pro Tyr Cys Trp Leu Val Trp Arg Pro Ser Leu Gly Ala Phe
        915                 920                 925

Tyr Ile Pro Val Ala Leu Ile Leu Leu Ile Thr Trp Ile Tyr Phe Leu
    930                 935                 940

Cys Ala Gly Leu Arg Leu Arg Gly Pro Leu Ala Gln Asn Pro Lys Ala
945                 950                 955                 960

Gly Asn Ser Arg Ala Ser Leu Glu Ala Gly Glu Glu Leu Arg Gly Ser
                965                 970                 975

Thr Arg Leu Arg Gly Ser Gly Pro Leu Leu Ser Asp Ser Gly Ser Leu
            980                 985                 990

Leu Ala Thr Gly Ser Ala Arg Val Gly Thr Pro Gly Pro Pro Glu Asp
        995                 1000                1005

Gly Asp Ser Leu Tyr Ser Pro Gly Val Gln Leu Gly Ala Leu Val Thr
    1010                1015                1020

Thr His Phe Leu Tyr Leu Ala Met Trp Ala Cys Gly Ala Leu Ala Val
1025                1030                1035                1040

Ser Gln Arg Trp Leu Pro Arg Val Val Cys Ser Cys Leu Tyr Gly Val
                1045                1050                1055

Ala Ala Ser Ala Leu Gly Leu Phe Val Phe Thr His His Cys Ala Arg
            1060                1065                1070

Arg Arg Asp Val Arg Ala Ser Trp Arg Ala Cys Cys Pro Pro Ala Ser
        1075                1080                1085

Pro Ala Ala Pro His Ala Pro Pro Arg Ala Leu Pro Ala Ala Ala Glu
    1090                1095                1100

Asp Gly Ser Pro Val Phe Gly Glu Gly Pro Pro Ser Leu Lys Ser Ser
```

-continued

```
1105                1110                1115                1120

Pro Ser Gly Ser Ser Gly His Pro Leu Ala Leu Gly Pro Cys Lys Leu
                1125                1130                1135

Thr Asn Leu Gln Leu Ala Gln Ser Gln Val Cys Glu Ala Gly Ala Ala
            1140                1145                1150

Ala Gly Gly Glu Gly Glu Pro Glu Pro Ala Gly Thr Arg Gly Asn Leu
        1155                1160                1165

Ala His Arg His Pro Asn Asn Val His His Gly Arg Arg Ala His Lys
    1170                1175                1180

Ser Arg Ala Lys Gly His Arg Ala Gly Glu Ala Cys Gly Lys Asn Arg
1185                1190                1195                1200

Leu Lys Ala Leu Arg Gly Gly Ala Ala Gly Ala Leu Glu Leu Leu Ser
                1205                1210                1215

Ser Glu Ser Gly Ser Leu His Asn Ser Pro Thr Asp Ser Tyr Leu Gly
            1220                1225                1230

Ser Ser Arg Asn Ser Pro Gly Ala Gly Leu Gln Leu Glu Gly Glu Pro
        1235                1240                1245

Met Leu Thr Pro Ser Glu Gly Ser Asp Thr Ser Ala Ala Pro Leu Ser
    1250                1255                1260

Glu Ala Gly Arg Ala Gly Gln Arg Arg Ser Ala Ser Arg Asp Ser Leu
1265                1270                1275                1280

Lys Gly Gly Gly Ala Leu Glu Lys Glu Ser His Arg Arg Ser Tyr Pro
                1285                1290                1295

Leu Asn Ala Ala Ser Leu Asn Gly Ala Pro Lys Gly Gly Lys Tyr Asp
            1300                1305                1310

Asp Val Thr Leu Met Gly Ala Glu Val Ala Ser Gly Gly Cys Met Lys
        1315                1320                1325

Thr Gly Leu Trp Lys Ser Glu Thr Thr Val
    1330                1335
```

<210> SEQ ID NO 3
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 3
gcatcacagc tgcagtcaac a 21

<210> SEQ ID NO 4
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 4
gccacaccag ccagcagta 19

<210> SEQ ID NO 5
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 5
ccacaactac cgggaccaca gccc 24

-continued

<210> SEQ ID NO 6
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 6
cacccccact gaaaaagatg a 21

<210> SEQ ID NO 7
<211> LENGTH: 26
<212> TYPE: DNA
<213> ORGANISM: Artificial Sequence
<220> FEATURE:
<223> OTHER INFORMATION: oligonucleotide primer

<400> SEQUENCE: 7
cttaactatc ttgggctgtg acaaag 26

<210> SEQ ID NO 8
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 8
tatgcctgcc gtgtgaacca cgtg 24

<210> SEQ ID NO 9
<211> LENGTH: 835
<212> TYPE: PRT
<213> ORGANISM: Homo sapiens

<400> SEQUENCE: 9

```
Met Gly Gly Arg Val Phe Leu Ala Phe Cys Val Trp Leu Thr Leu Pro
 1               5                  10                  15

Gly Ala Glu Thr Gln Asp Ser Arg Gly Cys Ala Arg Trp Cys Pro Gln
            20                  25                  30

Asn Ser Ser Cys Val Asn Ala Thr Ala Cys Arg Cys Asn Pro Gly Phe
        35                  40                  45

Ser Ser Phe Ser Glu Ile Ile Thr Thr Pro Thr Glu Thr Cys Asp Asp
    50                  55                  60

Ile Asn Glu Cys Ala Thr Pro Ser Lys Val Ser Cys Gly Lys Phe Ser
65                  70                  75                  80

Asp Cys Trp Asn Thr Glu Gly Ser Tyr Asp Cys Val Cys Ser Pro Gly
                85                  90                  95

Tyr Glu Pro Val Ser Gly Ala Lys Thr Phe Lys Asn Glu Ser Glu Asn
            100                 105                 110

Thr Cys Gln Asp Val Asp Glu Cys Gln Gln Asn Pro Arg Leu Cys Lys
        115                 120                 125

Ser Tyr Gly Thr Cys Val Asn Thr Leu Gly Ser Tyr Thr Cys Gln Cys
    130                 135                 140

Leu Pro Gly Phe Lys Phe Ile Pro Glu Asp Pro Lys Val Cys Thr Asp
145                 150                 155                 160

Val Asn Glu Cys Thr Ser Gly Gln Asn Pro Cys His Ser Ser Thr His
                165                 170                 175

Cys Leu Asn Asn Val Gly Ser Tyr Gln Cys Arg Cys Arg Pro Gly Trp
```

-continued

```
            180                 185                 190

Gln Pro Ile Pro Gly Ser Pro Asn Gly Pro Asn Asn Thr Val Cys Glu
        195                 200                 205

Asp Val Asp Glu Cys Ser Ser Gly Gln His Gln Cys Asp Ser Ser Thr
    210                 215                 220

Val Cys Phe Asn Thr Val Gly Ser Tyr Ser Cys Arg Cys Arg Pro Gly
225                 230                 235                 240

Trp Lys Pro Arg His Gly Ile Pro Asn Asn Gln Lys Asp Thr Val Cys
                245                 250                 255

Glu Asp Met Thr Phe Ser Thr Trp Thr Pro Pro Pro Gly Val His Ser
            260                 265                 270

Gln Thr Leu Ser Arg Phe Phe Asp Lys Val Gln Asp Leu Gly Arg Asp
        275                 280                 285

Ser Lys Thr Ser Ser Ala Glu Val Thr Ile Gln Asn Val Ile Lys Leu
    290                 295                 300

Val Asp Glu Leu Met Glu Ala Pro Gly Asp Val Glu Ala Leu Ala Pro
305                 310                 315                 320

Pro Val Arg His Leu Ile Ala Thr Gln Leu Leu Ser Asn Leu Glu Asp
                325                 330                 335

Ile Met Arg Ile Leu Ala Lys Ser Leu Pro Lys Gly Pro Phe Thr Tyr
            340                 345                 350

Ile Ser Pro Ser Asn Thr Glu Leu Thr Leu Met Ile Gln Glu Arg Gly
        355                 360                 365

Asp Lys Asn Val Thr Met Gly Gln Ser Ser Ala Arg Met Lys Leu Asn
    370                 375                 380

Trp Ala Val Ala Ala Gly Ala Glu Asp Pro Gly Pro Ala Val Ala Gly
385                 390                 395                 400

Ile Leu Ser Ile Gln Asn Met Thr Thr Leu Leu Ala Asn Ala Ser Leu
                405                 410                 415

Asn Leu His Ser Lys Lys Gln Ala Glu Leu Glu Glu Ile Tyr Glu Ser
            420                 425                 430

Ser Ile Arg Gly Val Gln Leu Arg Arg Leu Ser Ala Val Asn Ser Ile
        435                 440                 445

Phe Leu Ser His Asn Asn Thr Lys Glu Leu Asn Ser Pro Ile Leu Phe
    450                 455                 460

Ala Phe Ser His Leu Glu Ser Ser Asp Gly Glu Ala Gly Arg Asp Pro
465                 470                 475                 480

Pro Ala Lys Asp Val Met Pro Gly Pro Arg Gln Glu Leu Leu Cys Ala
                485                 490                 495

Phe Trp Lys Ser Asp Ser Asp Arg Gly Gly His Trp Ala Thr Glu Val
            500                 505                 510

Cys Gln Val Leu Gly Ser Lys Asn Gly Ser Thr Thr Cys Gln Cys Ser
        515                 520                 525

His Leu Ser Ser Phe Thr Ile Leu Met Ala His Tyr Asp Val Glu Asp
    530                 535                 540

Trp Lys Leu Thr Leu Ile Thr Arg Val Gly Leu Ala Leu Ser Leu Phe
545                 550                 555                 560

Cys Leu Leu Leu Cys Ile Leu Thr Phe Leu Leu Val Arg Pro Ile Gln
                565                 570                 575

Gly Ser Arg Thr Thr Ile His Leu His Leu Cys Ile Cys Leu Phe Val
            580                 585                 590

Gly Ser Thr Ile Phe Leu Ala Gly Ile Glu Asn Glu Gly Gly Gln Val
        595                 600                 605
```

-continued

```
Gly Leu Arg Cys Arg Leu Val Ala Gly Leu Leu His Tyr Cys Phe Leu
    610                 615                 620

Ala Ala Phe Cys Trp Met Ser Leu Glu Gly Leu Glu Leu Tyr Phe Leu
625                 630                 635                 640

Val Val Arg Val Phe Gln Gly Gln Gly Leu Ser Thr Arg Trp Leu Cys
                645                 650                 655

Leu Ile Gly Tyr Gly Val Pro Leu Leu Ile Val Gly Val Ser Ala Ala
            660                 665                 670

Ile Tyr Ser Lys Gly Tyr Gly Arg Pro Arg Tyr Cys Trp Leu Asp Phe
        675                 680                 685

Glu Gln Gly Phe Leu Trp Ser Phe Leu Gly Pro Val Thr Phe Ile Ile
    690                 695                 700

Leu Cys Asn Ala Val Ile Phe Val Thr Thr Val Trp Lys Leu Thr Gln
705                 710                 715                 720

Lys Phe Ser Glu Ile Asn Pro Asp Met Lys Lys Leu Lys Lys Ala Arg
                725                 730                 735

Ala Leu Thr Ile Thr Ala Ile Ala Gln Leu Phe Leu Leu Gly Cys Thr
            740                 745                 750

Trp Val Phe Gly Leu Phe Ile Phe Asp Asp Arg Ser Leu Val Leu Thr
        755                 760                 765

Tyr Val Phe Thr Ile Leu Asn Cys Leu Gln Gly Ala Phe Leu Tyr Leu
    770                 775                 780

Leu His Cys Leu Leu Asn Lys Lys Val Arg Glu Glu Tyr Arg Lys Trp
785                 790                 795                 800

Ala Cys Leu Val Ala Gly Gly Ser Lys Tyr Ser Glu Phe Thr Ser Thr
                805                 810                 815

Thr Ser Gly Thr Gly His Asn Gln Thr Arg Ala Leu Arg Ala Ser Glu
            820                 825                 830

Ser Gly Ile
        835


<210> SEQ ID NO 10
<211> LENGTH: 461
<212> TYPE: PRT
<213> ORGANISM: Homo sapiens

<400> SEQUENCE: 10

Met Glu Lys Lys Cys Thr Leu Tyr Phe Leu Val Leu Leu Pro Phe Phe
 1               5                  10                  15

Met Ile Leu Val Thr Ala Glu Leu Glu Glu Ser Pro Glu Asp Ser Ile
            20                  25                  30

Gln Leu Gly Val Thr Arg Asn Lys Ile Met Thr Ala Gln Tyr Glu Cys
        35                  40                  45

Tyr Gln Lys Ile Met Gln Asp Pro Ile Gln Gln Ala Glu Gly Val Tyr
    50                  55                  60

Cys Asn Arg Thr Trp Asp Gly Trp Leu Cys Trp Asn Asp Val Ala Ala
65                  70                  75                  80

Gly Thr Glu Ser Met Gln Leu Cys Pro Asp Tyr Phe Gln Asp Phe Asp
                85                  90                  95

Pro Ser Glu Lys Val Thr Lys Ile Cys Asp Gln Asp Gly Asn Trp Phe
            100                 105                 110

Arg His Pro Ala Ser Asn Arg Thr Trp Thr Asn Tyr Thr Gln Cys Asn
        115                 120                 125

Val Asn Thr His Glu Lys Val Lys Thr Ala Leu Asn Leu Phe Tyr Leu
```

-continued

```
    130                 135                 140

Thr Ile Ile Gly His Gly Leu Ser Ile Ala Ser Leu Leu Ile Ser Leu
145                 150                 155                 160

Gly Ile Phe Phe Tyr Phe Lys Ser Leu Ser Cys Gln Arg Ile Thr Leu
                165                 170                 175

His Lys Asn Leu Phe Phe Ser Phe Val Cys Asn Ser Val Val Thr Ile
            180                 185                 190

Ile His Leu Thr Ala Val Ala Asn Asn Gln Ala Leu Val Ala Thr Asn
        195                 200                 205

Pro Val Ser Cys Lys Val Ser Gln Phe Ile His Leu Tyr Leu Met Gly
    210                 215                 220

Cys Asn Tyr Phe Trp Met Leu Cys Glu Gly Ile Tyr Leu His Thr Leu
225                 230                 235                 240

Ile Val Val Ala Val Phe Ala Glu Lys Gln His Leu Met Trp Tyr Tyr
                245                 250                 255

Phe Leu Gly Trp Gly Phe Pro Leu Ile Pro Ala Cys Ile His Ala Ile
            260                 265                 270

Ala Arg Ser Leu Tyr Tyr Asn Asp Asn Cys Trp Ile Ser Ser Asp Thr
        275                 280                 285

His Leu Leu Tyr Ile Ile His Gly Pro Ile Cys Ala Ala Leu Leu Val
    290                 295                 300

Asn Leu Phe Phe Leu Leu Asn Ile Val Arg Val Leu Ile Thr Lys Leu
305                 310                 315                 320

Lys Val Thr His Gln Ala Glu Ser Asn Leu Tyr Met Lys Ala Val Arg
                325                 330                 335

Ala Thr Leu Ile Leu Val Pro Leu Leu Gly Ile Glu Phe Val Leu Ile
            340                 345                 350

Pro Trp Arg Pro Glu Gly Lys Ile Ala Glu Glu Val Tyr Asp Tyr Ile
        355                 360                 365

Met His Ile Leu Met His Phe Gln Gly Leu Leu Val Ser Thr Ile Phe
    370                 375                 380

Cys Phe Phe Asn Gly Glu Val Gln Ala Ile Leu Arg Arg Asn Trp Asn
385                 390                 395                 400

Gln Tyr Lys Ile Gln Phe Gly Asn Ser Phe Ser Asn Ser Glu Ala Leu
                405                 410                 415

Arg Ser Ala Ser Tyr Thr Val Ser Thr Ile Ser Asp Gly Pro Gly Tyr
            420                 425                 430

Ser His Asp Cys Pro Ser Glu His Leu Asn Gly Lys Ser Ile His Asp
        435                 440                 445

Ile Glu Asn Val Leu Leu Lys Pro Glu Asn Leu Tyr Asn
    450                 455                 460


<210> SEQ ID NO 11
<211> LENGTH: 444
<212> TYPE: PRT
<213> ORGANISM: Homo sapiens

<400> SEQUENCE: 11

Met Gly Gly His Pro Gln Leu Arg Leu Val Lys Ala Leu Leu Leu Leu
 1               5                  10                  15

Gly Leu Asn Pro Val Ser Ala Ser Leu Gln Asp Gln His Cys Glu Ser
            20                  25                  30

Leu Ser Leu Ala Ser Asn Ile Ser Gly Leu Gln Cys Asn Ala Ser Val
        35                  40                  45
```

-continued

```
Asp Leu Ile Gly Thr Cys Trp Pro Arg Ser Pro Ala Gly Gln Leu Val
    50                  55                  60

Val Arg Pro Cys Pro Ala Phe Phe Tyr Gly Val Arg Tyr Asn Thr Thr
65                  70                  75                  80

Asn Asn Gly Tyr Arg Glu Cys Leu Ala Asn Gly Ser Trp Ala Ala Arg
                85                  90                  95

Val Asn Tyr Ser Glu Cys Gln Glu Ile Leu Asn Glu Glu Lys Lys Ser
            100                 105                 110

Lys Val His Tyr His Val Ala Val Ile Ile Asn Tyr Leu Gly His Cys
        115                 120                 125

Ile Ser Leu Val Ala Leu Leu Val Ala Phe Val Leu Phe Leu Arg Leu
    130                 135                 140

Arg Pro Gly Cys Thr His Trp Gly Asp Gln Ala Asp Gly Ala Leu Glu
145                 150                 155                 160

Val Gly Ala Pro Trp Ser Gly Ala Pro Phe Gln Val Arg Arg Ser Ile
                165                 170                 175

Arg Cys Leu Arg Asn Ile Ile His Trp Asn Leu Ile Ser Ala Phe Ile
            180                 185                 190

Leu Arg Asn Ala Thr Trp Phe Val Val Gln Leu Thr Met Ser Pro Glu
        195                 200                 205

Val His Gln Ser Asn Val Gly Trp Cys Arg Leu Val Thr Ala Ala Tyr
    210                 215                 220

Asn Tyr Phe His Val Thr Asn Phe Phe Trp Met Phe Gly Glu Gly Cys
225                 230                 235                 240

Tyr Leu His Thr Ala Ile Val Leu Thr Tyr Ser Thr Asp Arg Leu Arg
                245                 250                 255

Lys Trp Met Phe Ile Cys Ile Gly Trp Gly Val Pro Phe Pro Ile Ile
            260                 265                 270

Val Ala Trp Ala Ile Gly Lys Leu Tyr Tyr Asp Asn Glu Lys Cys Trp
        275                 280                 285

Phe Gly Lys Arg Pro Gly Val Tyr Thr Asp Tyr Ile Tyr Gln Gly Pro
    290                 295                 300

Met Ile Leu Val Leu Leu Ile Asn Phe Ile Phe Leu Phe Asn Ile Val
305                 310                 315                 320

Arg Ile Leu Met Thr Lys Leu Arg Ala Ser Thr Thr Ser Glu Thr Ile
                325                 330                 335

Gln Tyr Arg Lys Ala Val Lys Ala Thr Leu Val Leu Leu Pro Leu Leu
            340                 345                 350

Gly Ile Thr Tyr Met Leu Phe Phe Val Asn Pro Gly Glu Asp Glu Val
        355                 360                 365

Ser Arg Val Val Phe Ile Tyr Phe Asn Ser Phe Leu Glu Ser Phe Gln
    370                 375                 380

Gly Phe Phe Val Ser Val Phe Tyr Cys Phe Leu Asn Ser Glu Val Arg
385                 390                 395                 400

Ser Ala Ile Arg Lys Arg Trp His Arg Trp Gln Asp Lys His Ser Ile
                405                 410                 415

Arg Ala Arg Val Ala Arg Ala Met Ser Ile Pro Thr Ser Pro Thr Arg
            420                 425                 430

Val Ser Phe His Ser Ile Lys Gln Ser Thr Ala Val
        435                 440
```

<210> SEQ ID NO 12
<211> LENGTH: 411
<212> TYPE: PRT

-continued

<213> ORGANISM: Homo sapiens

<400> SEQUENCE: 12

```
Met Asp Ala Ala Leu Leu His Ser Leu Leu Glu Ala Asn Cys Ser Leu
 1               5                  10                  15

Ala Leu Ala Glu Glu Leu Leu Leu Asp Gly Trp Gly Pro Pro Leu Asp
            20                  25                  30

Pro Glu Gly Pro Tyr Ser Tyr Cys Asn Thr Thr Leu Asp Gln Ile Gly
        35                  40                  45

Thr Cys Trp Pro Arg Ser Ala Ala Gly Ala Leu Val Glu Arg Pro Cys
    50                  55                  60

Pro Glu Tyr Phe Asn Gly Val Lys Tyr Asn Thr Thr Arg Asn Ala Tyr
65                  70                  75                  80

Arg Glu Cys Leu Glu Asn Gly Thr Trp Ala Ser Lys Ile Asn Tyr Ser
                85                  90                  95

Gln Cys Glu Pro Ile Leu Asp Asp Lys Gln Arg Lys Tyr Asp Leu His
            100                 105                 110

Tyr Arg Ile Ala Leu Val Val Asn Tyr Leu Gly His Cys Val Ser Val
        115                 120                 125

Ala Ala Leu Val Ala Ala Phe Leu Leu Phe Leu Ala Leu Arg Ser Ile
    130                 135                 140

Arg Cys Leu Arg Asn Val Ile His Trp Asn Leu Ile Thr Thr Phe Ile
145                 150                 155                 160

Leu Arg Asn Val Met Trp Phe Leu Leu Gln Leu Val Asp His Glu Val
                165                 170                 175

His Glu Ser Asn Glu Val Trp Cys Arg Cys Ile Thr Thr Ile Phe Asn
            180                 185                 190

Tyr Phe Val Val Thr Asn Phe Phe Trp Met Phe Val Glu Gly Cys Tyr
        195                 200                 205

Leu His Thr Ala Ile Val Met Thr Tyr Ser Thr Glu Arg Leu Arg Lys
    210                 215                 220

Cys Leu Phe Leu Phe Ile Gly Trp Cys Ile Pro Phe Pro Ile Ile Val
225                 230                 235                 240

Ala Trp Ala Ile Gly Lys Leu Tyr Tyr Glu Asn Glu Gln Cys Trp Phe
                245                 250                 255

Gly Lys Glu Pro Gly Asp Leu Val Asp Tyr Ile Tyr Gln Gly Pro Ile
            260                 265                 270

Ile Leu Val Leu Leu Ile Asn Phe Val Phe Leu Phe Asn Ile Val Arg
        275                 280                 285

Ile Leu Met Thr Lys Leu Arg Ala Ser Thr Thr Ser Glu Thr Ile Gln
    290                 295                 300

Tyr Arg Lys Ala Val Lys Ala Thr Leu Val Leu Leu Pro Leu Leu Gly
305                 310                 315                 320

Ile Thr Tyr Met Leu Phe Phe Val Asn Pro Gly Glu Asp Asp Leu Ser
                325                 330                 335

Gln Ile Met Phe Ile Tyr Phe Asn Ser Phe Leu Gln Ser Phe Gln Gly
            340                 345                 350

Phe Phe Val Ser Val Phe Tyr Cys Phe Phe Asn Gly Glu Val Arg Ser
        355                 360                 365

Ala Val Arg Lys Arg Trp His Arg Trp Gln Asp His His Ser Leu Arg
    370                 375                 380

Val Pro Met Ala Arg Ala Met Ser Ile Pro Thr Ser Pro Thr Arg Ile
385                 390                 395                 400
```

-continued

```
Ser Phe His Ser Ile Lys Gln Thr Ala Ala Val
                405                 410


<210> SEQ ID NO 13
<211> LENGTH: 490
<212> TYPE: PRT
<213> ORGANISM: Homo sapiens

<400> SEQUENCE: 13

Met Arg Phe Thr Phe Thr Ser Arg Cys Leu Ala Leu Phe Leu Leu Leu
 1               5                  10                  15

Asn His Pro Thr Pro Ile Leu Pro Ala Phe Ser Asn Gln Thr Tyr Pro
            20                  25                  30

Thr Ile Glu Pro Lys Pro Phe Leu Tyr Val Val Gly Arg Lys Lys Met
        35                  40                  45

Met Asp Ala Gln Tyr Lys Cys Tyr Asp Arg Met Gln Gln Leu Pro Ala
    50                  55                  60

Tyr Gln Gly Glu Gly Pro Tyr Cys Asn Arg Thr Trp Asp Gly Trp Leu
65                  70                  75                  80

Cys Trp Asp Asp Thr Pro Ala Gly Val Leu Ser Tyr Gln Phe Cys Pro
                85                  90                  95

Asp Tyr Phe Pro Asp Phe Asp Pro Ser Glu Lys Val Thr Lys Tyr Cys
            100                 105                 110

Asp Glu Lys Gly Val Trp Phe Lys His Pro Glu Asn Asn Arg Thr Trp
        115                 120                 125

Ser Asn Tyr Thr Met Cys Asn Ala Phe Thr Pro Glu Lys Leu Lys Asn
    130                 135                 140

Ala Tyr Val Leu Tyr Tyr Leu Ala Ile Val Gly His Ser Leu Ser Ile
145                 150                 155                 160

Phe Thr Leu Val Ile Ser Leu Gly Ile Phe Val Phe Phe Arg Lys Leu
                165                 170                 175

Thr Thr Ile Phe Pro Leu Asn Trp Lys Tyr Arg Lys Ala Leu Ser Leu
            180                 185                 190

Gly Cys Gln Arg Val Thr Leu His Lys Asn Met Phe Leu Thr Tyr Ile
        195                 200                 205

Leu Asn Ser Met Ile Ile Ile Ile His Leu Val Glu Val Val Pro Asn
    210                 215                 220

Gly Glu Leu Val Arg Arg Asp Pro Val Ser Cys Lys Ile Leu His Phe
225                 230                 235                 240

Phe His Gln Tyr Met Met Ala Cys Asn Tyr Phe Trp Met Leu Cys Glu
                245                 250                 255

Gly Ile Tyr Leu His Thr Leu Ile Val Val Ala Val Phe Thr Glu Lys
            260                 265                 270

Gln Arg Leu Arg Trp Tyr Tyr Leu Leu Gly Trp Gly Phe Pro Leu Val
        275                 280                 285

Pro Thr Thr Ile His Ala Ile Thr Arg Ala Val Tyr Phe Asn Asp Asn
    290                 295                 300

Cys Trp Leu Ser Val Glu Thr His Leu Leu Tyr Ile Ile His Gly Pro
305                 310                 315                 320

Val Met Ala Ala Leu Val Val Asn Phe Phe Phe Leu Leu Asn Ile Val
                325                 330                 335

Arg Val Leu Val Thr Lys Met Arg Glu Thr His Glu Ala Glu Ser His
            340                 345                 350

Met Tyr Leu Lys Ala Val Lys Ala Thr Met Ile Leu Val Pro Leu Leu
        355                 360                 365
```

-continued

```
Gly Ile Gln Phe Val Val Phe Pro Trp Arg Pro Ser Asn Lys Met Leu
    370                 375                 380

Gly Lys Ile Tyr Asp Tyr Val Met His Ser Leu Ile His Phe Gln Gly
385                 390                 395                 400

Phe Phe Val Ala Thr Ile Tyr Cys Phe Cys Asn Asn Glu Val Gln Thr
                405                 410                 415

Thr Val Lys Arg Gln Trp Ala Gln Phe Lys Ile Gln Trp Asn Gln Arg
            420                 425                 430

Trp Gly Arg Arg Pro Ser Asn Arg Ser Ala Arg Ala Ala Ala Ala Ala
        435                 440                 445

Ala Glu Ala Gly Asp Ile Pro Ile Tyr Ile Cys His Gln Glu Pro Arg
    450                 455                 460

Asn Glu Pro Ala Asn Asn Gln Gly Glu Glu Ser Ala Glu Ile Ile Pro
465                 470                 475                 480

Leu Asn Ile Ile Glu Gln Glu Ser Ser Ala
                485                 490


<210> SEQ ID NO 14
<211> LENGTH: 886
<212> TYPE: PRT
<213> ORGANISM: Homo sapiens

<400> SEQUENCE: 14

Met Arg Gly Phe Asn Leu Leu Leu Phe Trp Gly Cys Cys Val Met His
 1               5                  10                  15

Ser Trp Glu Gly His Ile Arg Pro Thr Arg Lys Pro Asn Thr Lys Gly
            20                  25                  30

Asn Asn Cys Arg Asp Ser Thr Leu Cys Pro Ala Tyr Ala Thr Cys Thr
        35                  40                  45

Asn Thr Val Asp Ser Tyr Tyr Cys Thr Cys Lys Gln Gly Phe Leu Ser
    50                  55                  60

Ser Asn Gly Gln Asn His Phe Lys Asp Pro Gly Val Arg Cys Lys Asp
65                  70                  75                  80

Ile Asp Glu Cys Ser Gln Ser Pro Gln Pro Cys Gly Pro Asn Ser Ser
                85                  90                  95

Cys Lys Asn Leu Ser Gly Arg Tyr Lys Cys Ser Cys Leu Asp Gly Phe
            100                 105                 110

Ser Ser Pro Thr Gly Asn Asp Trp Val Pro Gly Lys Pro Gly Asn Phe
        115                 120                 125

Ser Cys Thr Asp Ile Asn Glu Cys Leu Thr Ser Arg Val Cys Pro Glu
    130                 135                 140

His Ser Asp Cys Val Asn Ser Met Gly Ser Tyr Ser Cys Ser Cys Gln
145                 150                 155                 160

Val Gly Phe Ile Ser Arg Asn Ser Thr Cys Glu Asp Val Asn Glu Cys
                165                 170                 175

Ala Asp Pro Arg Ala Cys Pro Glu His Ala Thr Cys Asn Asn Thr Val
            180                 185                 190

Gly Asn Tyr Ser Cys Phe Cys Asn Pro Gly Phe Glu Ser Ser Ser Gly
        195                 200                 205

His Leu Ser Cys Gln Gly Leu Lys Ala Ser Cys Glu Asp Ile Asp Glu
    210                 215                 220

Cys Thr Glu Met Cys Pro Ile Asn Ser Thr Cys Thr Asn Thr Pro Gly
225                 230                 235                 240

Ser Tyr Phe Cys Thr Cys His Pro Gly Phe Ala Pro Ser Ser Gly Gln
```

-continued

```
                245                 250                 255

Leu Asn Phe Thr Asp Gln Gly Val Glu Cys Arg Asp Ile Asp Glu Cys
            260                 265                 270

Arg Gln Asp Pro Ser Thr Cys Gly Pro Asn Ser Ile Cys Thr Asn Ala
        275                 280                 285

Leu Gly Ser Tyr Ser Cys Gly Cys Ile Val Gly Phe His Pro Asn Pro
    290                 295                 300

Glu Gly Ser Gln Lys Asp Gly Asn Phe Ser Cys Gln Arg Val Leu Phe
305                 310                 315                 320

Lys Cys Lys Glu Asp Val Ile Pro Asp Asn Lys Gln Ile Gln Gln Cys
                325                 330                 335

Gln Glu Gly Thr Ala Val Lys Pro Ala Tyr Val Ser Phe Cys Ala Gln
            340                 345                 350

Ile Asn Asn Ile Phe Ser Val Leu Asp Lys Val Cys Glu Asn Lys Thr
        355                 360                 365

Thr Val Val Ser Leu Lys Asn Thr Thr Glu Ser Phe Val Pro Val Leu
    370                 375                 380

Lys Gln Ile Ser Met Trp Thr Lys Phe Thr Lys Glu Glu Thr Ser Ser
385                 390                 395                 400

Leu Ala Thr Val Phe Leu Glu Ser Val Glu Ser Met Thr Leu Ala Ser
                405                 410                 415

Phe Trp Lys Pro Ser Ala Asn Val Thr Pro Ala Val Arg Ala Glu Tyr
            420                 425                 430

Leu Asp Ile Glu Ser Lys Val Ile Asn Lys Glu Cys Ser Glu Glu Asn
        435                 440                 445

Val Thr Leu Asp Leu Val Ala Lys Gly Asp Lys Met Lys Ile Gly Cys
    450                 455                 460

Ser Thr Ile Glu Glu Ser Glu Ser Thr Glu Thr Thr Gly Val Ala Phe
465                 470                 475                 480

Val Ser Phe Val Gly Met Glu Ser Val Leu Asn Glu Arg Phe Phe Gln
                485                 490                 495

Asp His Gln Ala Pro Leu Thr Thr Ser Glu Ile Lys Leu Lys Met Asn
            500                 505                 510

Ser Arg Val Val Gly Gly Ile Met Thr Gly Glu Lys Lys Asp Gly Phe
        515                 520                 525

Ser Asp Pro Ile Ile Tyr Thr Leu Glu Asn Val Gln Pro Lys Gln Lys
    530                 535                 540

Phe Glu Arg Pro Ile Cys Val Ser Trp Ser Thr Asp Val Lys Gly Gly
545                 550                 555                 560

Arg Trp Thr Ser Phe Gly Cys Val Ile Leu Glu Ala Ser Glu Thr Tyr
                565                 570                 575

Thr Ile Cys Ser Cys Asn Gln Met Ala Asn Leu Ala Val Ile Met Ala
            580                 585                 590

Ser Gly Glu Leu Thr Met Asp Phe Ser Leu Tyr Ile Ile Ser His Val
        595                 600                 605

Gly Ile Ile Ile Ser Leu Val Cys Leu Val Leu Ala Ile Ala Thr Phe
    610                 615                 620

Leu Leu Cys Arg Ser Ile Arg Asn His Asn Thr Tyr Leu His Leu His
625                 630                 635                 640

Leu Cys Val Cys Leu Leu Leu Ala Lys Thr Leu Phe Leu Ala Gly Ile
                645                 650                 655

His Lys Thr Asp Asn Lys Thr Gly Cys Ala Ile Ile Ala Gly Phe Leu
            660                 665                 670
```

-continued

```
His Tyr Leu Phe Leu Ala Cys Phe Phe Trp Met Leu Val Glu Ala Val
        675                 680                 685

Ile Leu Phe Leu Met Val Arg Asn Leu Lys Val Val Asn Tyr Phe Ser
    690                 695                 700

Ser Arg Asn Ile Lys Met Leu His Ile Cys Ala Phe Gly Tyr Gly Leu
705                 710                 715                 720

Pro Met Leu Val Val Val Ile Ser Ala Ser Val Gln Pro Gln Gly Tyr
                725                 730                 735

Gly Met His Asn Arg Cys Trp Leu Asn Thr Glu Thr Gly Phe Ile Trp
            740                 745                 750

Ser Phe Leu Gly Pro Val Cys Thr Val Ile Val Ile Asn Ser Leu Leu
        755                 760                 765

Leu Thr Trp Thr Leu Trp Ile Leu Arg Gln Arg Leu Ser Ser Val Asn
    770                 775                 780

Ala Glu Val Ser Thr Leu Lys Asp Thr Arg Leu Leu Thr Phe Lys Ala
785                 790                 795                 800

Phe Ala Gln Leu Phe Ile Leu Gly Cys Ser Trp Val Leu Gly Ile Phe
                805                 810                 815

Gln Ile Gly Pro Val Ala Gly Val Met Ala Tyr Leu Phe Thr Ile Ile
            820                 825                 830

Asn Ser Leu Gln Gly Ala Phe Ile Phe Leu Ile His Cys Leu Leu Asn
        835                 840                 845

Gly Gln Val Arg Glu Glu Tyr Lys Arg Trp Ile Thr Gly Lys Thr Lys
    850                 855                 860

Pro Ser Ser Gln Ser Gln Thr Ser Arg Ile Leu Leu Ser Ser Met Pro
865                 870                 875                 880

Ser Ala Ser Lys Thr Gly
                885


<210> SEQ ID NO 15
<211> LENGTH: 466
<212> TYPE: PRT
<213> ORGANISM: Homo sapiens

<400> SEQUENCE: 15

Met Thr Thr Ser Pro Ile Leu Gln Leu Leu Leu Arg Leu Ser Leu Cys
 1               5                  10                  15

Gly Leu Leu Leu Gln Arg Ala Glu Thr Gly Ser Lys Gly Gln Thr Ala
            20                  25                  30

Gly Glu Leu Tyr Gln Arg Trp Glu Arg Tyr Arg Arg Glu Cys Gln Glu
        35                  40                  45

Thr Leu Ala Ala Ala Glu Pro Pro Ser Gly Leu Ala Cys Asn Gly Ser
    50                  55                  60

Phe Asp Met Tyr Val Cys Trp Asp Tyr Ala Ala Pro Asn Ala Thr Ala
65                  70                  75                  80

Arg Ala Ser Cys Pro Trp Tyr Leu Pro Trp His His His Val Ala Ala
                85                  90                  95

Gly Phe Val Leu Arg Gln Cys Gly Ser Asp Gly Gln Trp Gly Leu Trp
            100                 105                 110

Arg Asp His Thr Gln Cys Glu Asn Pro Glu Lys Asn Glu Ala Phe Leu
        115                 120                 125

Asp Gln Arg Leu Ile Leu Glu Arg Leu Gln Val Met Tyr Thr Val Gly
    130                 135                 140

Tyr Ser Leu Ser Leu Ala Thr Leu Leu Leu Ala Leu Leu Ile Leu Ser
```

-continued

```
145                 150                 155                 160

Leu Phe Arg Arg Leu His Cys Thr Arg Asn Tyr Ile His Ile Asn Leu
                165                 170                 175

Phe Thr Ser Phe Met Leu Arg Ala Ala Ala Ile Leu Ser Arg Asp Arg
            180                 185                 190

Leu Leu Pro Arg Pro Gly Pro Tyr Leu Gly Asp Gln Ala Leu Ala Leu
        195                 200                 205

Trp Asn Gln Ala Leu Ala Ala Cys Arg Thr Ala Gln Ile Val Thr Gln
    210                 215                 220

Tyr Cys Val Gly Ala Asn Tyr Thr Trp Leu Leu Val Glu Gly Val Tyr
225                 230                 235                 240

Leu His Ser Leu Leu Val Leu Val Gly Gly Ser Glu Glu Gly His Phe
                245                 250                 255

Arg Tyr Tyr Leu Leu Leu Gly Trp Gly Ala Pro Ala Leu Phe Val Ile
            260                 265                 270

Pro Trp Val Ile Val Arg Tyr Leu Tyr Glu Asn Thr Gln Cys Trp Glu
        275                 280                 285

Arg Asn Glu Val Lys Ala Ile Trp Trp Ile Ile Arg Thr Pro Ile Leu
    290                 295                 300

Met Thr Ile Leu Ile Asn Phe Leu Ile Phe Ile Arg Ile Leu Gly Ile
305                 310                 315                 320

Leu Leu Ser Lys Leu Arg Thr Arg Gln Met Arg Cys Arg Asp Tyr Arg
                325                 330                 335

Leu Arg Leu Ala Arg Ser Thr Leu Thr Leu Val Pro Leu Leu Gly Val
            340                 345                 350

His Glu Val Val Phe Ala Pro Val Thr Glu Glu Gln Ala Arg Gly Ala
        355                 360                 365

Leu Arg Phe Ala Lys Leu Gly Phe Glu Ile Phe Leu Ser Ser Phe Gln
    370                 375                 380

Gly Phe Leu Val Ser Val Leu Tyr Cys Phe Ile Asn Lys Glu Val Gln
385                 390                 395                 400

Ser Glu Ile Arg Arg Gly Trp His His Cys Arg Leu Arg Arg Ser Leu
                405                 410                 415

Gly Glu Glu Gln Arg Gln Leu Pro Glu Arg Ala Phe Arg Ala Leu Pro
            420                 425                 430

Ser Gly Ser Gly Pro Gly Glu Val Pro Thr Ser Arg Gly Leu Ser Ser
        435                 440                 445

Gly Thr Leu Pro Gly Pro Gly Asn Glu Ala Ser Arg Glu Leu Glu Ser
    450                 455                 460

Tyr Cys
465


<210> SEQ ID NO 16
<211> LENGTH: 463
<212> TYPE: PRT
<213> ORGANISM: Homo sapiens

<400> SEQUENCE: 16

Met Ala Gly Ala Pro Gly Pro Leu Arg Leu Ala Leu Leu Leu Leu Gly
 1               5                  10                  15

Met Val Gly Arg Ala Gly Pro Arg Pro Gln Gly Ala Thr Val Ser Leu
            20                  25                  30

Trp Glu Thr Val Gln Lys Trp Arg Glu Tyr Arg Arg Gln Cys Gln Arg
        35                  40                  45
```

-continued

```
Ser Leu Thr Glu Asp Pro Pro Pro Ala Thr Asp Leu Phe Cys Asn Arg
    50                  55                  60

Thr Phe Asp Glu Tyr Ala Cys Trp Pro Asp Gly Glu Pro Gly Ser Phe
65                  70                  75                  80

Val Asn Val Ser Cys Pro Trp Tyr Leu Pro Trp Ala Ser Ser Val Pro
                85                  90                  95

Gln Gly His Val Tyr Arg Phe Cys Thr Ala Glu Gly Leu Trp Leu Gln
            100                 105                 110

Lys Asp Asn Ser Ser Leu Pro Trp Arg Asp Leu Ser Glu Cys Glu Glu
        115                 120                 125

Ser Lys Arg Gly Glu Arg Ser Ser Pro Glu Glu Gln Leu Leu Phe Leu
    130                 135                 140

Tyr Ile Ile Tyr Thr Val Gly Tyr Ala Leu Ser Phe Ser Ala Leu Val
145                 150                 155                 160

Ile Ala Ser Ala Ile Leu Leu Gly Phe Arg His Leu His Cys Thr Arg
                165                 170                 175

Asn Tyr Ile His Leu Asn Leu Phe Ala Ser Phe Ile Leu Arg Ala Leu
            180                 185                 190

Ser Val Phe Ile Lys Asp Ala Ala Leu Lys Trp Met Tyr Ser Thr Ala
        195                 200                 205

Ala Gln Gln His Gln Trp Asp Gly Leu Leu Ser Tyr Gln Asp Ser Leu
    210                 215                 220

Ser Cys Arg Leu Val Phe Leu Leu Met Gln Tyr Cys Val Ala Ala Asn
225                 230                 235                 240

Tyr Tyr Trp Leu Leu Val Glu Gly Val Tyr Leu Tyr Thr Leu Leu Ala
                245                 250                 255

Phe Ser Val Phe Ser Glu Gln Trp Ile Phe Arg Leu Tyr Val Ser Ile
            260                 265                 270

Gly Trp Gly Val Pro Leu Leu Phe Val Val Pro Trp Gly Ile Val Lys
        275                 280                 285

Tyr Leu Tyr Glu Asp Glu Gly Cys Trp Thr Arg Asn Ser Asn Met Asn
    290                 295                 300

Tyr Trp Leu Ile Ile Arg Leu Pro Ile Leu Phe Ala Ile Gly Val Asn
305                 310                 315                 320

Phe Leu Ile Phe Val Arg Val Ile Cys Ile Val Val Ser Lys Leu Lys
                325                 330                 335

Ala Asn Leu Met Cys Lys Thr Asp Ile Lys Cys Arg Leu Ala Lys Ser
            340                 345                 350

Thr Leu Thr Leu Ile Pro Leu Leu Gly Thr His Glu Val Ile Phe Ala
        355                 360                 365

Phe Val Met Asp Glu His Ala Arg Gly Thr Leu Arg Phe Ile Lys Leu
    370                 375                 380

Phe Thr Glu Leu Ser Phe Thr Ser Phe Gln Gly Leu Met Val Ala Ile
385                 390                 395                 400

Leu Tyr Cys Phe Val Asn Asn Glu Val Gln Leu Glu Phe Arg Lys Ser
                405                 410                 415

Trp Glu Arg Trp Arg Leu Glu His Leu His Ile Gln Arg Asp Ser Ser
            420                 425                 430

Met Lys Pro Leu Lys Cys Pro Thr Ser Ser Leu Ser Ser Gly Ala Thr
        435                 440                 445

Ala Gly Ser Ser Met Tyr Thr Ala Thr Cys Gln Ala Ser Cys Ser
    450                 455                 460
```

-continued

<210> SEQ ID NO 17
<211> LENGTH: 477
<212> TYPE: PRT
<213> ORGANISM: Homo sapiens

<400> SEQUENCE: 17

```
Met Pro Pro Cys Gln Pro Gln Arg Pro Leu Leu Leu Leu Leu Leu Leu
 1               5                  10                  15

Leu Ala Cys Gln Pro Gln Val Pro Ser Ala Gln Val Met Asp Phe Leu
            20                  25                  30

Phe Glu Lys Trp Lys Leu Tyr Gly Asp Gln Cys His His Asn Leu Ser
        35                  40                  45

Leu Leu Pro Pro Pro Thr Glu Leu Val Cys Asn Arg Thr Phe Asp Lys
    50                  55                  60

Tyr Ser Cys Trp Pro Asp Thr Pro Ala Asn Thr Thr Ala Asn Ile Ser
65                  70                  75                  80

Cys Pro Trp Tyr Leu Pro Trp His His Lys Val Gln His Arg Phe Val
                85                  90                  95

Phe Lys Arg Cys Gly Pro Asp Gly Gln Trp Val Arg Gly Pro Arg Gly
            100                 105                 110

Gln Pro Trp Arg Asp Ala Ser Gln Cys Gln Met Asp Gly Glu Glu Ile
        115                 120                 125

Glu Val Gln Lys Glu Val Ala Lys Met Tyr Ser Ser Phe Gln Val Met
    130                 135                 140

Tyr Thr Val Gly Tyr Ser Leu Ser Leu Gly Ala Leu Leu Leu Ala Leu
145                 150                 155                 160

Ala Ile Leu Gly Gly Leu Ser Lys Leu His Cys Thr Arg Asn Ala Ile
                165                 170                 175

His Ala Asn Leu Phe Ala Ser Phe Val Leu Lys Ala Ser Ser Val Leu
            180                 185                 190

Val Ile Asp Gly Leu Leu Arg Thr Arg Tyr Ser Gln Lys Ile Gly Asp
        195                 200                 205

Asp Leu Ser Val Ser Thr Trp Leu Ser Asp Gly Ala Val Ala Gly Cys
    210                 215                 220

Arg Val Ala Ala Val Phe Met Gln Tyr Gly Ile Val Ala Asn Tyr Cys
225                 230                 235                 240

Trp Leu Leu Val Glu Gly Leu Tyr Leu His Asn Leu Leu Gly Leu Ala
                245                 250                 255

Thr Leu Pro Glu Arg Ser Phe Phe Ser Leu Tyr Leu Gly Ile Gly Trp
            260                 265                 270

Gly Ala Pro Met Leu Phe Val Val Pro Trp Ala Val Val Lys Cys Leu
        275                 280                 285

Phe Glu Asn Val Gln Cys Trp Thr Ser Asn Asp Asn Met Gly Phe Trp
    290                 295                 300

Trp Ile Leu Arg Phe Pro Val Phe Leu Ala Ile Leu Ile Asn Phe Phe
305                 310                 315                 320

Ile Phe Val Arg Ile Val Gln Leu Leu Val Ala Lys Leu Arg Ala Arg
                325                 330                 335

Gln Met His His Thr Asp Tyr Lys Phe Arg Leu Ala Lys Ser Thr Leu
            340                 345                 350

Thr Leu Ile Pro Leu Leu Gly Val His Glu Val Val Phe Ala Phe Val
        355                 360                 365

Thr Asp Glu His Ala Gln Gly Thr Leu Arg Ser Ala Lys Leu Phe Phe
    370                 375                 380
```

-continued

```
Asp Leu Phe Leu Ser Ser Phe Gln Gly Leu Leu Val Ala Val Leu Tyr
385                 390                 395                 400

Cys Phe Leu Asn Lys Glu Val Gln Ser Glu Leu Arg Arg Arg Trp His
                405                 410                 415

Arg Trp Arg Leu Gly Lys Val Leu Trp Glu Glu Arg Asn Thr Ser Asn
            420                 425                 430

His Arg Ala Ser Ser Ser Pro Gly His Gly Pro Pro Ser Lys Glu Leu
        435                 440                 445

Gln Phe Gly Arg Gly Gly Gly Ser Gln Asp Ser Ser Ala Glu Thr Pro
    450                 455                 460

Leu Ala Gly Gly Leu Pro Arg Leu Ala Glu Ser Pro Phe
465                 470                 475


<210> SEQ ID NO 18
<211> LENGTH: 423
<212> TYPE: PRT
<213> ORGANISM: Homo sapiens

<400> SEQUENCE: 18

Met Asp Arg Arg Met Trp Gly Ala His Val Phe Cys Val Leu Ser Pro
 1               5                  10                  15

Leu Pro Thr Val Leu Gly His Met His Pro Glu Cys Asp Phe Ile Thr
            20                  25                  30

Gln Leu Arg Glu Asp Glu Ser Ala Cys Leu Gln Ala Ala Glu Glu Met
        35                  40                  45

Pro Asn Thr Thr Leu Gly Cys Pro Ala Thr Trp Asp Gly Leu Leu Cys
    50                  55                  60

Trp Pro Thr Ala Gly Ser Gly Glu Trp Val Thr Leu Pro Cys Pro Asp
65                  70                  75                  80

Phe Phe Ser His Phe Ser Ser Glu Ser Gly Ala Val Lys Arg Asp Cys
                85                  90                  95

Thr Ile Thr Gly Trp Ser Glu Pro Phe Pro Pro Tyr Pro Val Ala Cys
            100                 105                 110

Pro Val Pro Leu Glu Leu Leu Ala Glu Glu Glu Ser Tyr Phe Ser Thr
        115                 120                 125

Val Lys Ile Ile Tyr Thr Val Gly His Ser Ile Ser Ile Val Ala Leu
    130                 135                 140

Phe Val Ala Ile Thr Ile Leu Val Ala Leu Arg Arg Leu His Cys Pro
145                 150                 155                 160

Arg Asn Tyr Val His Thr Gln Leu Phe Thr Thr Phe Ile Leu Lys Ala
                165                 170                 175

Gly Ala Val Phe Leu Lys Asp Ala Ala Leu Phe His Ser Asp Asp Thr
            180                 185                 190

Asp His Cys Ser Phe Ser Thr Val Leu Cys Lys Val Ser Val Ala Ala
        195                 200                 205

Ser His Phe Ala Thr Met Thr Asn Phe Ser Trp Leu Leu Ala Glu Ala
    210                 215                 220

Val Tyr Leu Asn Cys Leu Leu Ala Ser Thr Ser Pro Ser Ser Arg Arg
225                 230                 235                 240

Ala Phe Trp Trp Leu Val Leu Ala Gly Trp Gly Leu Pro Val Leu Phe
                245                 250                 255

Thr Gly Thr Trp Val Ser Cys Lys Leu Ala Phe Glu Asp Ile Ala Cys
            260                 265                 270

Trp Asp Leu Asp Asp Thr Ser Pro Tyr Trp Trp Ile Ile Lys Gly Pro
        275                 280                 285
```

```
Ile Val Leu Ser Val Gly Val Asn Phe Gly Leu Phe Leu Asn Ile Ile
    290                 295                 300

Arg Ile Leu Val Arg Lys Leu Glu Pro Ala Gln Gly Ser Leu His Thr
305                 310                 315                 320

Gln Ser Gln Tyr Trp Arg Leu Ser Lys Ser Thr Leu Phe Leu Ile Pro
                325                 330                 335

Leu Phe Gly Ile His Tyr Ile Ile Phe Asn Phe Leu Pro Asp Asn Ala
            340                 345                 350

Gly Leu Gly Ile Arg Leu Pro Leu Glu Leu Gly Leu Gly Ser Phe Gln
        355                 360                 365

Gly Phe Ile Val Ala Ile Leu Tyr Cys Phe Leu Asn Gln Glu Val Arg
    370                 375                 380

Thr Glu Ile Ser Arg Lys Trp His Gly His Asp Pro Glu Leu Leu Pro
385                 390                 395                 400

Ala Trp Arg Thr Arg Ala Lys Trp Thr Thr Pro Ser Arg Ser Ala Ala
                405                 410                 415

Lys Val Leu Thr Ser Met Cys
            420


<210> SEQ ID NO 19
<211> LENGTH: 468
<212> TYPE: PRT
<213> ORGANISM: Homo sapiens

<400> SEQUENCE: 19

Met Ala Gly Val Val His Val Ser Leu Ala Ala Leu Leu Leu Leu Pro
 1               5                  10                  15

Met Ala Pro Ala Met His Ser Asp Cys Ile Phe Lys Lys Glu Gln Ala
            20                  25                  30

Met Cys Leu Glu Lys Ile Gln Arg Ala Asn Glu Leu Met Gly Phe Asn
        35                  40                  45

Asp Ser Ser Pro Gly Cys Pro Gly Met Trp Asp Asn Ile Thr Cys Trp
    50                  55                  60

Lys Pro Ala His Val Gly Glu Met Val Leu Val Ser Cys Pro Glu Leu
65                  70                  75                  80

Phe Arg Ile Phe Asn Pro Asp Gln Val Trp Glu Thr Glu Thr Ile Gly
                85                  90                  95

Glu Ser Asp Phe Gly Asp Ser Asn Ser Leu Asp Leu Ser Asp Met Gly
            100                 105                 110

Val Val Ser Arg Asn Cys Thr Glu Asp Gly Trp Ser Glu Pro Phe Pro
        115                 120                 125

His Tyr Phe Asp Ala Cys Gly Phe Asp Glu Tyr Glu Ser Glu Thr Gly
    130                 135                 140

Asp Gln Asp Tyr Tyr Tyr Leu Ser Val Lys Ala Leu Tyr Thr Val Gly
145                 150                 155                 160

Tyr Ser Thr Ser Leu Val Thr Leu Thr Thr Ala Met Val Ile Leu Cys
                165                 170                 175

Arg Phe Arg Lys Leu His Cys Thr Arg Asn Phe Ile His Met Asn Leu
            180                 185                 190

Phe Val Ser Phe Met Leu Arg Ala Ile Ser Val Phe Ile Lys Asp Trp
        195                 200                 205

Ile Leu Tyr Ala Glu Gln Asp Ser Asn His Cys Phe Ile Ser Thr Val
    210                 215                 220

Glu Cys Lys Ala Val Met Val Phe Phe His Tyr Cys Val Val Ser Asn
```

-continued

```
225                 230                 235                 240

Tyr Phe Trp Leu Phe Ile Glu Gly Leu Tyr Leu Phe Thr Leu Leu Val
                245                 250                 255

Glu Thr Phe Phe Pro Glu Arg Arg Tyr Phe Tyr Trp Tyr Thr Ile Ile
            260                 265                 270

Gly Trp Gly Thr Pro Thr Val Cys Val Thr Val Trp Ala Thr Leu Arg
        275                 280                 285

Leu Tyr Phe Asp Asp Thr Gly Cys Trp Asp Met Asn Asp Ser Thr Ala
    290                 295                 300

Leu Trp Trp Val Ile Lys Gly Pro Val Val Gly Ser Ile Met Val Asn
305                 310                 315                 320

Phe Val Leu Phe Ile Gly Ile Ile Val Ile Leu Val Gln Lys Leu Gln
                325                 330                 335

Ser Pro Asp Met Gly Gly Asn Glu Ser Ser Ile Tyr Leu Arg Leu Ala
            340                 345                 350

Arg Ser Thr Leu Leu Leu Ile Pro Leu Phe Gly Ile His Tyr Thr Val
        355                 360                 365

Phe Ala Phe Ser Pro Glu Asn Val Ser Lys Arg Glu Arg Leu Val Phe
    370                 375                 380

Glu Leu Gly Leu Gly Ser Phe Gln Gly Phe Val Val Ala Val Leu Tyr
385                 390                 395                 400

Cys Phe Leu Asn Gly Glu Val Gln Ala Glu Ile Lys Arg Lys Trp Arg
                405                 410                 415

Ser Trp Lys Val Asn Arg Tyr Phe Ala Val Asp Phe Lys His Arg His
            420                 425                 430

Pro Ser Leu Ala Ser Ser Gly Val Asn Gly Gly Thr Gln Leu Ser Ile
        435                 440                 445

Leu Ser Lys Ser Ser Ser Gln Ile Arg Met Ser Gly Leu Pro Ala Asp
    450                 455                 460

Asn Leu Ala Thr
465


<210> SEQ ID NO 20
<211> LENGTH: 550
<212> TYPE: PRT
<213> ORGANISM: Homo sapiens

<400> SEQUENCE: 20

Met Ala Gly Leu Gly Ala Ser Leu His Val Trp Gly Trp Leu Met Leu
 1               5                  10                  15

Gly Ser Cys Leu Leu Ala Arg Ala Gln Leu Asp Ser Asp Gly Thr Ile
            20                  25                  30

Thr Ile Glu Glu Gln Ile Val Leu Val Leu Lys Ala Lys Val Gln Cys
        35                  40                  45

Glu Leu Asn Ile Thr Ala Gln Leu Gln Glu Gly Glu Gly Asn Cys Phe
    50                  55                  60

Pro Glu Trp Asp Gly Leu Ile Cys Trp Pro Arg Gly Thr Val Gly Lys
65                  70                  75                  80

Ile Ser Ala Val Pro Cys Pro Pro Tyr Ile Tyr Asp Phe Asn His Lys
                85                  90                  95

Gly Val Ala Phe Arg His Cys Asn Pro Asn Gly Thr Trp Asp Phe Met
            100                 105                 110

His Ser Leu Asn Lys Thr Trp Ala Asn Tyr Ser Asp Cys Leu Arg Phe
        115                 120                 125
```

-continued

```
Leu Gln Pro Asp Ile Ser Ile Gly Lys Gln Glu Phe Phe Glu Arg Leu
    130                 135                 140

Tyr Val Met Tyr Thr Val Gly Tyr Ser Ile Ser Phe Gly Ser Leu Ala
145                 150                 155                 160

Val Ala Ile Leu Ile Ile Gly Tyr Phe Arg Arg Leu His Cys Thr Arg
                165                 170                 175

Asn Tyr Ile His Met His Leu Phe Val Ser Phe Met Leu Arg Ala Thr
            180                 185                 190

Ser Ile Phe Val Lys Asp Arg Val Val His Ala His Ile Gly Val Lys
        195                 200                 205

Glu Leu Glu Ser Leu Ile Met Gln Asp Asp Pro Gln Asn Ser Ile Glu
    210                 215                 220

Ala Thr Ser Val Asp Lys Ser Gln Tyr Ile Gly Cys Lys Ile Ala Val
225                 230                 235                 240

Val Met Phe Ile Tyr Phe Leu Ala Thr Asn Tyr Tyr Trp Ile Leu Val
                245                 250                 255

Glu Gly Leu Tyr Leu His Asn Leu Ile Phe Val Ala Phe Phe Ser Asp
            260                 265                 270

Thr Lys Tyr Leu Trp Gly Phe Ile Leu Ile Gly Trp Gly Phe Pro Ala
        275                 280                 285

Ala Phe Val Ala Ala Trp Ala Val Ala Arg Ala Thr Leu Ala Asp Ala
    290                 295                 300

Arg Cys Trp Glu Leu Ser Ala Gly Asp Ile Lys Trp Ile Tyr Gln Ala
305                 310                 315                 320

Pro Ile Leu Ala Ala Ile Gly Leu Asn Phe Ile Leu Phe Leu Asn Thr
                325                 330                 335

Val Arg Val Leu Ala Thr Lys Ile Trp Glu Thr Asn Ala Val Gly His
            340                 345                 350

Asp Thr Arg Lys Gln Tyr Arg Lys Leu Ala Lys Ser Thr Leu Val Leu
        355                 360                 365

Val Leu Val Phe Gly Val His Tyr Ile Val Phe Val Cys Leu Pro His
    370                 375                 380

Ser Phe Thr Gly Leu Gly Trp Glu Ile Arg Met His Cys Glu Leu Phe
385                 390                 395                 400

Phe Asn Ser Phe Gln Gly Phe Phe Val Ser Ile Ile Tyr Cys Tyr Cys
                405                 410                 415

Asn Gly Glu Val Gln Ala Glu Val Lys Lys Met Trp Ser Arg Trp Asn
            420                 425                 430

Leu Ser Val Asp Trp Lys Arg Thr Pro Pro Cys Gly Ser Arg Arg Cys
        435                 440                 445

Gly Ser Val Leu Thr Thr Val Thr His Ser Thr Ser Ser Gln Ser Gln
    450                 455                 460

Val Ala Ala Ser Thr Arg Met Val Leu Ile Ser Gly Lys Ala Ala Lys
465                 470                 475                 480

Ile Ala Ser Arg Gln Pro Asp Ser His Ile Thr Leu Pro Gly Tyr Val
                485                 490                 495

Trp Ser Asn Ser Glu Gln Asp Cys Leu Pro His Ser Phe His Glu Glu
            500                 505                 510

Thr Lys Glu Asp Ser Gly Arg Gln Gly Asp Asp Ile Leu Met Glu Lys
        515                 520                 525

Pro Ser Arg Pro Met Glu Ser Asn Pro Asp Thr Glu Gly Cys Gln Gly
    530                 535                 540

Glu Thr Glu Asp Val Leu
```

-continued 545 550

<210> SEQ ID NO 21
<211> LENGTH: 593
<212> TYPE: PRT
<213> ORGANISM: Homo sapiens

<400> SEQUENCE: 21

Met Gly Thr Ala Arg Ile Ala Pro Gly Leu Ala Leu Leu Leu Cys Cys
1 5 10 15

Pro Val Leu Ser Ser Ala Tyr Ala Leu Val Asp Ala Asp Asp Val Met
20 25 30

Thr Lys Glu Glu Gln Ile Phe Leu Leu His Arg Ala Gln Ala Gln Cys
35 40 45

Glu Lys Arg Leu Lys Glu Val Leu Gln Arg Pro Ala Ser Ile Met Glu
50 55 60

Ser Asp Lys Gly Trp Thr Ser Ala Ser Thr Ser Gly Lys Pro Arg Lys
65 70 75 80

Asp Lys Ala Ser Gly Lys Leu Tyr Pro Glu Ser Glu Glu Asp Lys Glu
85 90 95

Ala Pro Thr Gly Ser Arg Tyr Arg Gly Arg Pro Cys Leu Pro Glu Trp
100 105 110

Asp His Ile Leu Cys Trp Pro Leu Gly Ala Pro Gly Glu Val Val Ala
115 120 125

Val Pro Cys Pro Asp Tyr Ile Tyr Asp Phe Asn His Lys Gly His Ala
130 135 140

Tyr Arg Arg Cys Asp Arg Asn Gly Ser Trp Glu Leu Val Pro Gly His
145 150 155 160

Asn Arg Thr Trp Ala Asn Tyr Ser Glu Cys Val Lys Phe Leu Thr Asn
165 170 175

Glu Thr Arg Glu Arg Glu Val Phe Asp Arg Leu Gly Met Ile Tyr Thr
180 185 190

Val Gly Tyr Ser Val Ser Leu Ala Ser Leu Thr Val Ala Val Leu Ile
195 200 205

Leu Ala Tyr Phe Arg Arg Leu His Cys Thr Arg Asn Tyr Ile His Met
210 215 220

His Leu Phe Leu Ser Phe Met Leu Arg Ala Val Ser Ile Phe Val Lys
225 230 235 240

Asp Ala Val Leu Tyr Ser Gly Ala Thr Leu Asp Glu Ala Glu Arg Leu
245 250 255

Thr Glu Glu Glu Leu Arg Ala Ile Ala Gln Ala Pro Pro Pro Pro Ala
260 265 270

Thr Ala Ala Ala Gly Tyr Ala Gly Cys Arg Val Ala Val Thr Phe Phe
275 280 285

Leu Tyr Phe Leu Ala Thr Asn Tyr Tyr Trp Ile Leu Val Glu Gly Leu
290 295 300

Tyr Leu His Ser Leu Ile Phe Met Ala Phe Phe Ser Glu Lys Lys Tyr
305 310 315 320

Leu Trp Gly Phe Thr Val Phe Gly Trp Gly Leu Pro Ala Val Phe Val
325 330 335

Ala Val Trp Val Ser Val Arg Ala Thr Leu Ala Asn Thr Gly Cys Trp
340 345 350

Asp Leu Ser Ser Gly Asn Lys Lys Trp Ile Ile Gln Val Pro Ile Leu
355 360 365

-continued

```
Ala Ser Ile Val Leu Asn Phe Ile Leu Phe Ile Asn Ile Val Arg Val
    370                 375                 380

Leu Ala Thr Lys Leu Arg Glu Thr Asn Ala Gly Arg Cys Asp Thr Arg
385                 390                 395                 400

Gln Gln Tyr Arg Lys Leu Leu Lys Ser Thr Leu Val Leu Met Pro Leu
                405                 410                 415

Phe Gly Val His Tyr Ile Val Phe Met Ala Thr Pro Tyr Thr Glu Val
            420                 425                 430

Ser Gly Thr Leu Trp Gln Val Gln Met His Tyr Glu Met Leu Phe Asn
        435                 440                 445

Ser Phe Gln Gly Phe Phe Val Ala Ile Ile Tyr Cys Phe Cys Asn Gly
    450                 455                 460

Glu Val Gln Ala Glu Ile Lys Lys Ser Trp Ser Arg Trp Thr Leu Ala
465                 470                 475                 480

Leu Asp Phe Lys Arg Lys Ala Arg Ser Gly Ser Ser Ser Tyr Ser Tyr
                485                 490                 495

Gly Pro Met Val Ser His Thr Ser Val Thr Asn Val Gly Pro Arg Val
            500                 505                 510

Gly Leu Gly Leu Pro Leu Ser Pro Arg Leu Leu Pro Thr Ala Thr Thr
        515                 520                 525

Asn Gly His Pro Gln Leu Pro Gly His Ala Lys Pro Gly Thr Pro Ala
    530                 535                 540

Leu Glu Thr Leu Glu Thr Thr Pro Pro Ala Met Ala Ala Pro Lys Asp
545                 550                 555                 560

Asp Gly Phe Leu Asn Gly Ser Cys Ser Gly Leu Asp Glu Glu Ala Ser
                565                 570                 575

Gly Pro Glu Arg Pro Pro Ala Leu Leu Gln Glu Glu Trp Glu Thr Val
            580                 585                 590

Met


<210> SEQ ID NO 22
<211> LENGTH: 440
<212> TYPE: PRT
<213> ORGANISM: Homo sapiens

<400> SEQUENCE: 22

Met Arg Pro His Leu Ser Pro Pro Leu Gln Gln Leu Leu Leu Pro Val
 1               5                  10                  15

Leu Leu Ala Cys Ala Ala His Ser Thr Gly Ala Leu Pro Arg Leu Cys
            20                  25                  30

Asp Val Leu Gln Val Leu Trp Glu Glu Gln Asp Gln Cys Leu Gln Glu
        35                  40                  45

Leu Ser Arg Glu Gln Thr Gly Asp Leu Gly Thr Glu Gln Pro Val Pro
    50                  55                  60

Gly Cys Glu Gly Met Trp Asp Asn Ile Ser Cys Trp Pro Ser Ser Val
65                  70                  75                  80

Pro Gly Arg Met Val Glu Val Glu Cys Pro Arg Phe Leu Arg Met Leu
                85                  90                  95

Thr Ser Arg Asn Gly Ser Leu Phe Arg Asn Cys Thr Gln Asp Gly Trp
            100                 105                 110

Ser Glu Thr Phe Pro Arg Pro Asn Leu Ala Cys Gly Val Asn Val Asn
        115                 120                 125

Asp Ser Ser Asn Glu Lys Arg His Ser Tyr Leu Leu Lys Leu Lys Val
    130                 135                 140
```

-continued

```
Met Tyr Thr Val Gly Tyr Ser Ser Ser Leu Val Met Leu Leu Val Ala
145                 150                 155                 160

Leu Gly Ile Leu Cys Ala Phe Arg Arg Leu His Cys Thr Arg Asn Tyr
                165                 170                 175

Ile His Met His Leu Phe Val Ser Phe Ile Leu Arg Ala Leu Ser Asn
            180                 185                 190

Phe Ile Lys Asp Ala Val Leu Phe Ser Ser Asp Asp Val Thr Tyr Cys
        195                 200                 205

Asp Ala His Arg Ala Gly Cys Lys Leu Val Met Val Leu Phe Gln Tyr
    210                 215                 220

Cys Ile Met Ala Asn Tyr Ser Trp Leu Leu Val Glu Gly Leu Tyr Leu
225                 230                 235                 240

His Thr Leu Leu Ala Ile Ser Phe Phe Ser Glu Arg Lys Tyr Leu Gln
                245                 250                 255

Gly Phe Val Ala Phe Gly Trp Gly Ser Pro Ala Ile Phe Val Ala Leu
            260                 265                 270

Trp Ala Ile Ala Arg His Phe Leu Glu Asp Val Gly Cys Trp Asp Ile
        275                 280                 285

Asn Ala Asn Ala Ser Ile Trp Trp Ile Ile Arg Gly Pro Val Ile Leu
    290                 295                 300

Ser Ile Leu Ile Asn Phe Ile Leu Phe Ile Asn Ile Leu Arg Ile Leu
305                 310                 315                 320

Met Arg Lys Leu Arg Thr Gln Glu Thr Arg Gly Asn Glu Val Ser His
                325                 330                 335

Tyr Lys Arg Leu Ala Arg Ser Thr Leu Leu Leu Ile Pro Leu Phe Gly
            340                 345                 350

Ile His Tyr Ile Val Phe Ala Phe Ser Pro Glu Asp Ala Met Glu Ile
        355                 360                 365

Gln Leu Phe Phe Glu Leu Ala Leu Gly Ser Phe Gln Gly Leu Val Val
    370                 375                 380

Ala Val Leu Tyr Cys Phe Leu Asn Gly Glu Val Gln Leu Glu Val Gln
385                 390                 395                 400

Lys Lys Trp Gln Gln Trp His Leu Arg Glu Phe Pro Leu His Pro Val
                405                 410                 415

Ala Ser Phe Ser Asn Ser Thr Lys Ala Ser His Leu Glu Gln Ser Gln
            420                 425                 430

Gly Thr Cys Arg Thr Ser Ile Ile
        435                 440


<210> SEQ ID NO 23
<211> LENGTH: 457
<212> TYPE: PRT
<213> ORGANISM: Homo sapiens

<400> SEQUENCE: 23

Met Arg Pro Pro Ser Pro Leu Pro Ala Arg Trp Leu Cys Val Leu Ala
 1               5                  10                  15

Gly Ala Leu Ala Trp Ala Leu Gly Pro Ala Gly Gly Gln Ala Ala Arg
            20                  25                  30

Leu Gln Glu Glu Cys Asp Tyr Val Gln Met Ile Glu Val Gln His Lys
        35                  40                  45

Gln Cys Leu Glu Glu Ala Gln Leu Glu Asn Glu Thr Ile Gly Cys Ser
    50                  55                  60

Lys Met Trp Asp Asn Leu Thr Cys Trp Pro Ala Thr Pro Arg Gly Gln
65                  70                  75                  80
```

-continued

```
Val Val Val Leu Ala Cys Pro Leu Ile Phe Lys Leu Phe Ser Ser Ile
                85                  90                  95

Gln Gly Arg Asn Val Ser Arg Ser Cys Thr Asp Glu Gly Trp Thr His
            100                 105                 110

Leu Glu Pro Gly Pro Tyr Pro Ile Ala Cys Gly Leu Asp Asp Lys Ala
        115                 120                 125

Ala Ser Leu Asp Glu Gln Gln Thr Met Phe Tyr Gly Ser Val Lys Thr
    130                 135                 140

Gly Tyr Thr Ile Gly Tyr Gly Leu Ser Leu Ala Thr Leu Leu Val Ala
145                 150                 155                 160

Thr Ala Ile Leu Ser Leu Phe Arg Lys Leu His Cys Thr Arg Asn Tyr
                165                 170                 175

Ile His Met His Leu Phe Ile Ser Phe Ile Leu Arg Ala Ala Ala Val
            180                 185                 190

Phe Ile Lys Asp Leu Ala Leu Phe Asp Ser Gly Glu Ser Asp Gln Cys
        195                 200                 205

Ser Glu Gly Ser Val Gly Cys Lys Ala Ala Met Val Phe Phe Gln Tyr
    210                 215                 220

Cys Val Met Ala Asn Phe Phe Trp Leu Leu Val Glu Gly Leu Tyr Leu
225                 230                 235                 240

Tyr Thr Leu Leu Ala Val Ser Phe Phe Ser Glu Arg Lys Tyr Phe Trp
                245                 250                 255

Gly Tyr Ile Leu Ile Gly Trp Gly Val Pro Ser Thr Phe Thr Met Val
            260                 265                 270

Trp Thr Ile Ala Arg Ile His Phe Glu Asp Tyr Gly Cys Trp Asp Thr
        275                 280                 285

Ile Asn Ser Ser Leu Trp Trp Ile Ile Lys Gly Pro Ile Leu Thr Ser
    290                 295                 300

Ile Leu Val Asn Phe Ile Leu Phe Ile Cys Ile Ile Arg Ile Leu Leu
305                 310                 315                 320

Gln Lys Leu Arg Pro Pro Asp Ile Arg Lys Ser Asp Ser Ser Pro Tyr
                325                 330                 335

Ser Arg Leu Ala Arg Ser Thr Leu Leu Leu Ile Pro Leu Phe Gly Val
            340                 345                 350

His Tyr Ile Met Phe Ala Phe Phe Pro Asp Asn Phe Lys Pro Glu Val
        355                 360                 365

Lys Met Val Phe Glu Leu Val Val Gly Ser Phe Gln Gly Phe Val Val
    370                 375                 380

Ala Ile Leu Tyr Cys Phe Leu Asn Gly Glu Val Gln Ala Glu Leu Arg
385                 390                 395                 400

Arg Lys Trp Arg Arg Trp His Leu Gln Gly Val Leu Gly Trp Asn Pro
                405                 410                 415

Lys Tyr Arg His Pro Ser Gly Gly Ser Asn Gly Ala Thr Cys Ser Thr
            420                 425                 430

Gln Val Ser Met Leu Thr Arg Val Ser Pro Gly Ala Arg Arg Ser Ser
        435                 440                 445

Ser Phe Gln Ala Glu Val Ser Leu Val
    450                 455
```

<210> SEQ ID NO 24
<211> LENGTH: 438
<212> TYPE: PRT
<213> ORGANISM: Homo sapiens -continued

<400> SEQUENCE: 24

```
Met Arg Thr Leu Leu Pro Pro Ala Leu Leu Thr Cys Trp Leu Leu Ala
 1               5                  10                  15

Pro Val Asn Ser Ile His Pro Glu Cys Arg Phe His Leu Glu Ile Gln
            20                  25                  30

Glu Glu Glu Thr Lys Cys Ala Glu Leu Leu Arg Ser Gln Thr Glu Lys
        35                  40                  45

His Lys Ala Cys Ser Gly Val Trp Asp Asn Ile Thr Cys Trp Arg Pro
    50                  55                  60

Ala Asn Val Gly Glu Thr Val Thr Val Pro Cys Pro Lys Val Phe Ser
65                  70                  75                  80

Asn Phe Tyr Ser Lys Ala Gly Asn Ile Ser Lys Asn Cys Thr Ser Asp
                85                  90                  95

Gly Trp Ser Glu Thr Phe Pro Asp Phe Val Asp Ala Cys Gly Tyr Ser
            100                 105                 110

Asp Pro Glu Asp Glu Ser Lys Ile Thr Phe Tyr Ile Leu Val Lys Ala
        115                 120                 125

Ile Tyr Thr Leu Gly Tyr Ser Val Ser Leu Met Ser Leu Ala Thr Gly
    130                 135                 140

Ser Ile Ile Leu Cys Leu Phe Arg Lys Leu His Cys Thr Arg Asn Tyr
145                 150                 155                 160

Ile His Leu Asn Leu Phe Leu Ser Phe Ile Leu Arg Ala Ile Ser Val
                165                 170                 175

Leu Val Lys Asp Asp Val Leu Tyr Ser Ser Ser Gly Thr Leu His Cys
            180                 185                 190

Pro Asp Gln Pro Ser Ser Trp Val Gly Cys Lys Leu Ser Leu Val Phe
        195                 200                 205

Leu Gln Tyr Cys Ile Met Ala Asn Phe Phe Trp Leu Leu Val Glu Gly
    210                 215                 220

Leu Tyr Leu His Thr Leu Leu Val Ala Met Leu Pro Pro Arg Arg Cys
225                 230                 235                 240

Phe Leu Ala Tyr Leu Leu Ile Gly Trp Gly Leu Pro Thr Val Cys Ile
                245                 250                 255

Gly Ala Trp Thr Ala Ala Arg Leu Tyr Leu Glu Asp Thr Gly Cys Trp
            260                 265                 270

Asp Thr Asn Asp His Ser Val Pro Trp Trp Val Ile Arg Ile Pro Ile
        275                 280                 285

Leu Ile Ser Ile Ile Val Asn Phe Val Leu Phe Ile Ser Ile Ile Arg
    290                 295                 300

Ile Leu Leu Gln Lys Leu Thr Ser Pro Asp Val Gly Gly Asn Asp Gln
305                 310                 315                 320

Ser Gln Tyr Lys Arg Leu Ala Lys Ser Thr Leu Leu Leu Ile Pro Leu
                325                 330                 335

Phe Gly Val His Tyr Met Val Phe Ala Val Phe Pro Ile Ser Ile Ser
            340                 345                 350

Ser Lys Tyr Gln Ile Leu Phe Glu Leu Cys Leu Gly Ser Phe Gln Gly
        355                 360                 365

Leu Val Val Ala Val Leu Tyr Cys Phe Leu Asn Ser Glu Val Gln Cys
    370                 375                 380

Glu Leu Lys Arg Lys Trp Arg Ser Arg Cys Pro Thr Pro Ser Ala Ser
385                 390                 395                 400

Arg Asp Tyr Arg Val Cys Gly Ser Ser Phe Ser Arg Asn Gly Ser Glu
                405                 410                 415
```

-continued

```
Gly Ala Leu Gln Phe His Arg Gly Ser Arg Ala Gln Ser Phe Leu Gln
            420                 425                 430

Thr Glu Thr Ser Val Ile
        435
```